(12) United States Patent
Clary et al.

(10) Patent No.: US 7,863,332 B2
(45) Date of Patent: Jan. 4, 2011

(54) BIAROMATIC COMPOUND ACTIVATORS OF PPARγ RECEPTORS AND COSMETIC/PHARMACEUTICAL COMPOSITIONS COMPRISED THEREOF

(75) Inventors: Laurence Clary, La Colle sur Loup (FR); Jean-Guy Boiteau, Saint Aunes (FR); Corinne Millois Barbuis, Saint Raphael (FR)

(73) Assignee: Galderma Research & Development, Biot (FR)

( * ) Notice: Subject to any disclaimer, the term of this patent is extended or adjusted under 35 U.S.C. 154(b) by 0 days.

(21) Appl. No.: 11/707,123

(22) Filed: Feb. 16, 2007

(65) Prior Publication Data

US 2007/0213336 A1 Sep. 13, 2007

Related U.S. Application Data

(63) Continuation of application No. PCT/EP2005/009990, filed on Aug. 12, 2005.

(60) Provisional application No. 60/607,781, filed on Sep. 8, 2004.

(30) Foreign Application Priority Data

Aug. 17, 2004 (FR) .................................... 04 08933

(51) Int. Cl.
*A61K 31/17* (2006.01)
*A61K 31/24* (2006.01)
*C07C 275/28* (2006.01)
*C07C 275/40* (2006.01)
*C07C 275/42* (2006.01)
*C07C 229/42* (2006.01)
*C07C 229/44* (2006.01)
*C07C 335/16* (2006.01)
*C07C 335/20* (2006.01)

(52) U.S. Cl. ....................... 514/598; 514/539; 514/562; 514/564; 514/586; 514/597; 560/9; 560/34; 562/426; 562/439; 564/26; 564/50

(58) Field of Classification Search .................. 564/52, 564/26, 50; 514/598, 539, 562, 564, 586, 514/597; 560/9, 34; 562/426, 439
See application file for complete search history.

(56) References Cited

U.S. PATENT DOCUMENTS

| 6,908,939 | B2 * | 6/2005 | Bernardon et al. | 514/369 |
|---|---|---|---|---|
| 6,927,228 | B2 * | 8/2005 | Bernardon et al. | 514/369 |
| 7,122,564 | B2 * | 10/2006 | Bernardon et al. | 514/357 |
| 7,125,869 | B2 * | 10/2006 | Clary et al. | 514/234.8 |
| 7,285,568 | B2 * | 10/2007 | Clary et al. | 514/378 |
| 2005/0256116 | A1 * | 11/2005 | Clary et al. | 514/232.5 |
| 2007/0112070 | A1 * | 5/2007 | Aubert et al. | 514/534 |
| 2007/0207175 | A1 * | 9/2007 | Clary et al. | 424/401 |
| 2007/0213336 | A1 * | 9/2007 | Clary et al. | 514/249 |
| 2008/0004274 | A1 * | 1/2008 | Diaz et al. | 514/235.2 |
| 2008/0027077 | A1 * | 1/2008 | Boiteau et al. | 514/256 |

FOREIGN PATENT DOCUMENTS

| FR | 2833949 A1 * | 6/2003 |
|---|---|---|
| FR | 2847251 A1 * | 5/2004 |
| FR | 2847580 A1 * | 5/2004 |
| FR | 2848553 A1 * | 6/2004 |
| WO | WO 01/16120 A1 | 3/2001 |
| WO | WO 02/12210 A1 | 2/2002 |
| WO | WO 03/055867 A1 | 7/2003 |
| WO | WO 2004048351 A2 * | 6/2004 |

OTHER PUBLICATIONS

XP-002358643; Beilstein Registry No. 9360111; 2 pages.
XP-002358644; Beilstein Registry No. 9358578; 2 pages.
XP-002358645; Beilstein Registry No. 9171527; 2 pages.
Ramachandran et al., "Fine Tuning of PPAR Ligands for Type 2 Diabetes and Metabolic Syndrome," *Mini-Review in Medicinal Chemistry*, 2006, 6, 563-573, Bentham Science Publishers Ltd.

* cited by examiner

*Primary Examiner*—Peter G O'Sullivan
(74) *Attorney, Agent, or Firm*—Buchanan Ingersoll & Rooney PC

(57) ABSTRACT

Novel biaromatic compounds having the general formula (I):

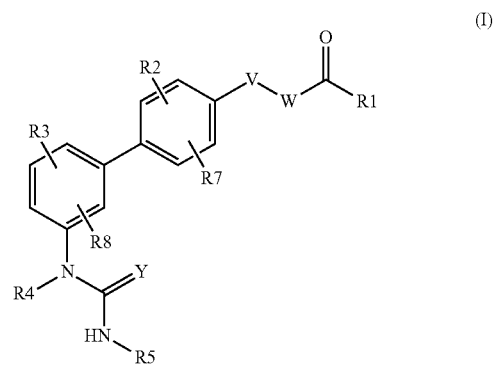

and cosmetic/pharmaceutical compositions comprised thereof are useful in human or veterinary medicine (in dermatology and also in the fields of cardiovascular diseases, of immune diseases and/or of diseases related to the metabolism of lipids) or, alternatively, in cosmetic compositions.

24 Claims, 3 Drawing Sheets

BIAROMATIC COMPOUND ACTIVATORS OF PPARγ RECEPTORS AND COSMETIC/PHARMACEUTICAL COMPOSITIONS COMPRISED THEREOF

CROSS-REFERENCE TO PRIORITY/PCT/PROVISIONAL APPLICATIONS

This application claims priority under 35 U.S.C. §119 of FR 04/08933, filed Aug. 17, 2004, and of Provisional Application No. 60/607,781, filed Sep. 8, 2004, and is a continuation of PCT/EP 2005/009990 filed Aug. 12, 2005 and designating the United States, published in the English language as WO 2006/018326 A1 on Feb. 23, 2006, each hereby expressly incorporated by reference in its entirety and each assigned to the assignee hereof.

CROSS-REFERENCE TO COMPANION APPLICATION

Copending U.S. patent application Ser. No. 11/707,125 filed concurrently herewith, hereby also expressly incorporated by reference and also assigned to the assignee hereof.

BACKGROUND OF THE INVENTION

1. Technical Field of the Invention

The present invention relates, as novel and useful industrial products, to a novel class of biaromatic compounds that activate the Peroxisome Proliferator-Activated Receptor type receptors of subtype γ (PPARγ). This invention also relates to processes for the preparation of same and to their formulation into pharmaceutical compositions useful in human or veterinary medicine, or, alternatively, into cosmetic compositions.

2. Description of Background and/or Related and/or Prior Art

The activity of receptors of PPAR type has been the subject of numerous studies. See, for example, the publication entitled "Differential Expression of Peroxisome Proliferator-Activated Receptor Subtypes During the Differentiation of Human Keratinocytes", Michel Rivier et al., *J. Invest. Dermatol.*, 111, 1998, pp. 1116-1121, in which is listed a large number of bibliographic references relating to PPAR type receptors. See also the report entitled "The PPARs: From orphan receptors to Drug Discovery", Timothy M. Willson, Peter J. Brown, Daniel D. Sternbach, and Brad R. Henke, *J. Med. Chem.*, 2000, Vol. 43, pp. 527-550.

The PPAR receptors activate transcription by binding to DNA sequence elements known as the peroxisome proliferator response elements (PPRE), in the form of a heterodimer with the retinoid X receptors (known as RXRs).

Three subtypes of human PPAR have been identified and described: PPARα, PPARγ and PPARδ (or NUC1).

PPARα is mainly expressed in the liver, whereas PPARδ is ubiquitous.

Of the three subtypes, PPARγ is the one that has been the most extensively studied. All the references suggest a critical role of PPARγ in the regulation of differentiation of adipocytes, where it is strongly expressed. It also plays a key role in systemic lipid homeostasis.

It has especially been described in WO 96/33724 that PPARγ-selective compounds, such as a prostaglandin-J2 or -D2, are potential active agents for the treatment of obesity and diabetes.

Moreover, in WO 02/12210 and WO 03/055867 the assignee hereof describes the formulation of biaromatic compounds that activate PPARγ type receptors into a pharmaceutical composition, the composition being useful for treating skin disorders associated with an anomaly of epidermal cell differentiation.

Need continues to exist for novel compounds that have good activity and advantageous pharmaceutical properties.

SUMMARY OF THE INVENTION

A novel family of propanoic compounds has now been developed that have the advantage of being 10 to 100 times more active than the compounds identified in the preceding WO 02/12210 and WO 03/055867, with regard to PPAR gamma receptors. Moreover, in addition to their better activity, certain of the compounds according to the present invention are obtained in solid form. The synthesis thereof and the purification thereof thus are easier.

Too, the use of compounds in solid form makes it possible to avoid the drawbacks of oils in the context of pharmaceutical development on account of the residual solvents which may be present therein.

Thus, the present invention features biaromatic compounds having the following general formula (I):

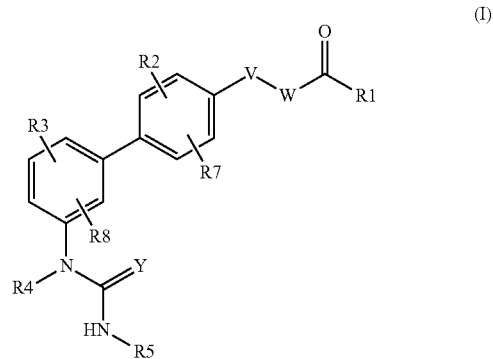

in which:

R1 is a hydroxyl radical, a radical —OR6 or a hydroxylamine radical;

R6 is as defined below,

R2 and R3, which may be identical or different, are each a hydrogen atom, a halogen atom, an alkyl radical having from 1 to 12 carbon atoms, a hydroxyl radical, an alkoxy radical, a polyether radical, an aralkyl radical, an aryl radical, an amino radical that may be substituted by one or two radicals, which may be identical or different, selected from among an alkyl radical having from 1 to 12 carbon atoms and an aralkyl radical;

R4 is a hydrogen atom or a lower alkyl radical having from 1 to 4 carbon atoms;

R5 is an alkyl radical having from 1 to 12 carbon atoms, an aryl radical, an aralkyl radical, a heteroaryl radical or a heterocyclic radical;

R6 is an alkyl, aryl or aralkyl radical;

R7 and R8, which may be identical or different, are each a hydrogen atom, a halogen atom, an alkyl radical having from 1 to 12 carbon atoms, a hydroxyl radical, an alkoxy radical, a polyether radical, an aralkyl radical, an aryl radical, an amino radical that may be substituted by one or two radicals, which may be identical or different, selected from among an alkyl radical having from 1 to 12 carbon atoms or an aralkyl radical;

Y is an oxygen or sulfur atom;

V—W is a single or double carbon-carbon bond, i.e., a sequence CH$_2$—CH$_2$ or CH=CH and the salts thereof.

Figure 1:
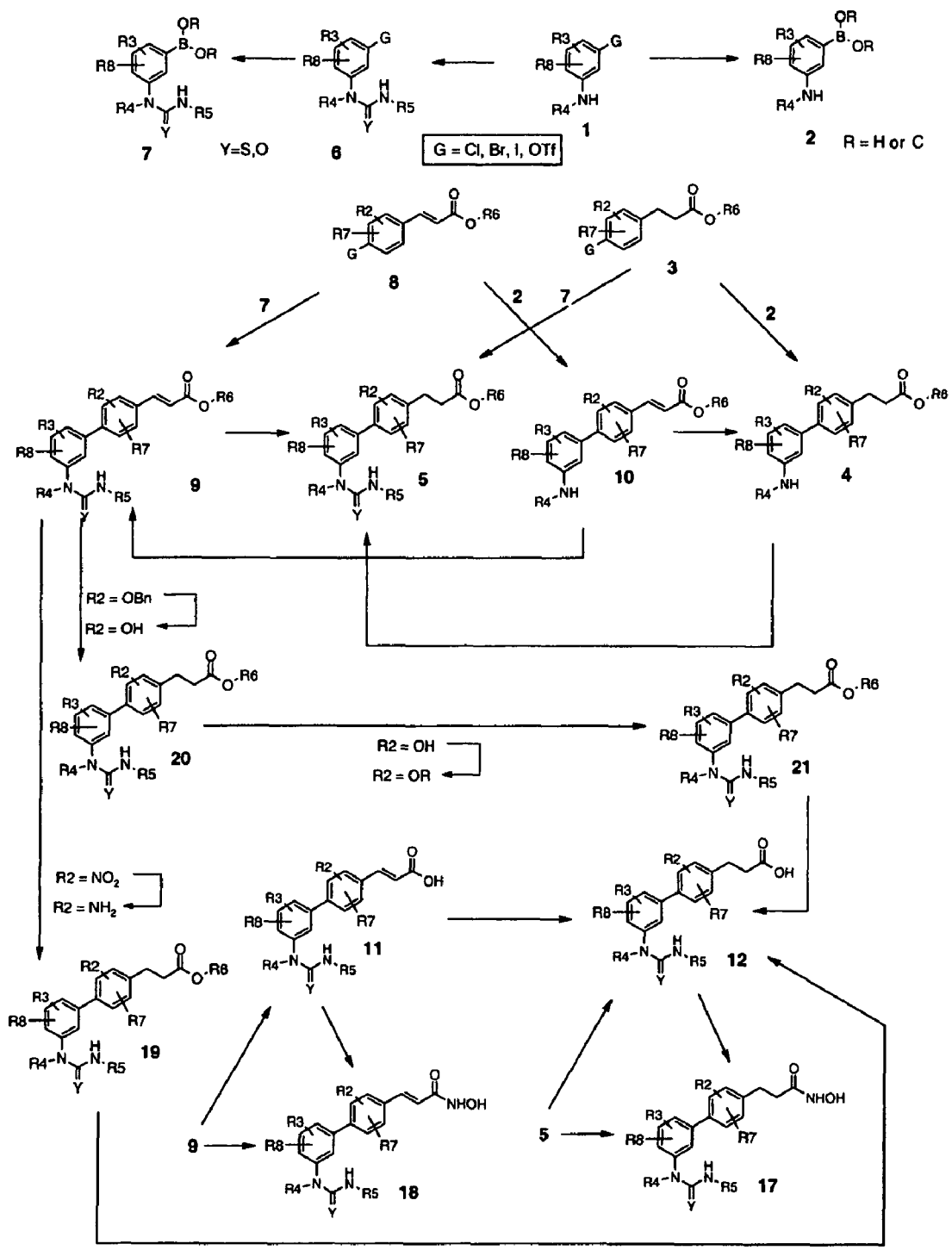
FIGS. 1-3 show a variety of reaction schemes for the ultimate preparation of the biaromatic compounds according to the invention.

DETAILED DESCRIPTION OF BEST MODE AND SPECIFIC/PREFERRED EMBODIMENTS OF THE INVENTION

In particular, when the compounds according to the invention are in the form of salts, they are salts of an alkali metal, in particular a sodium or potassium salt, or an alkaline-earth metal salt, or salts of organic amines, more particularly of amino acids such as arginine or lysine.

When the compounds according to the invention have an amine function and are in the form of salts of this amine, these are salts of a mineral acid, for instance hydrochloric acid, sulfuric acid or hydrobromic acid, or salts of an organic acid, for instance acetic acid, triflic acid, tartaric acid, oxalic acid, citric acid or nitric acid.

According to the present invention, the term "alkyl radical having from 1 to 12 carbon atoms" means a linear, branched or cyclic, saturated or unsaturated carbon-based chain that may be interrupted with a hetero atom and that may be substituted with one or more radicals selected from among a halogen atom, a hydroxyl radical, an alkoxy radical and a heterocyclic radical, and preferably the alkyl radicals are methyl, ethyl, propyl, isopropyl, butyl, tert-butyl, isoamyl, amyl, hexyl, heptyl, octyl, decyl, cyclohexyl, methylcyclohexyl, methylcyclobutyl, methylcyclopentyl or methylcyclohexyl radicals.

The term "lower alkyl radical having from 1 to 4 carbon atoms" will preferably be a methyl, ethyl, propyl, methylcyclopropyl, isopropyl, tert-butyl or n-butyl radical.

The term "aryl radical" means a phenyl, biphenyl, cinnamyl or naphthyl radical that may be substituted by a halogen atom, a CF$_3$ radical, an alkyl radical having from 1 to 12 carbon atoms, an alkoxy radical, a nitro function, a polyether radical, an aryl radical, a benzoyl radical, an alkyl ester group, a carboxylic acid, a hydroxyl radical optionally protected with an acetyl or benzoyl group or an amino radical optionally protected with an acetyl or benzoyl group or optionally substituted by at least one alkyl radical having from 1 to 12 carbon atoms, an aralkoxy radical, a phenoxy radical or an amide radical H$_2$NCO.

The term "aralkyl radical" means an alkyl radical having from 1 to 12 carbon atoms substituted by an aryl radical or by a heteroaryl radical.

The term "hydroxylamine radical" means the sequence —NHOH.

The term "halogen atom" means a fluorine, chlorine, bromine or iodine atom.

According to the present invention, the term "hydroxyl radical" means the —OH radical.

The term "alkoxy radical" means an oxygen atom substituted by an alkyl radical having from 1 to 12 carbon atoms, and the alkoxy radicals are preferably methoxy, ethoxy, isopropyloxy, n-propyloxy, tert-butoxy, n-butoxy, n-pentyloxy, n-hexyloxy, cyclopropylmethoxy, cyclobutylmethoxy, cyclopentylmethoxy or cyclohexylmethoxy radicals.

The term "aralkoxy radical" means an oxygen atom substituted with an aralkyl radical.

The term "polyether radical" means a radical having from 1 to 7 carbon atoms interrupted by at least one oxygen atom, and preferably radicals such as methoxyethoxy, ethoxyethoxy or methoxyethoxyethoxy radicals.

The term "heteroaryl radical" means an aryl radical interrupted by one or more hetero atoms, such as a pyridyl, furyl, thienyl, isoxazolyl, oxadiazolyl, oxazolyl, isothiazolyl, quinazolinyl, benzothiadiazolyl, benzimidazole, indolyl or benzofuran radical, optionally substituted by at least one halogen, an alkyl radical having from 1 to 12 carbon atoms, an alkoxy radical, an aryl radical, a nitro function, a polyether radical, a heteroaryl radical, a benzoyl radical, an alkyl ester group, a carboxylic acid, a hydroxyl optionally protected with an acetyl or benzoyl group or an amino radical optionally protected with an acetyl or benzoyl group or optionally substituted by at least one alkyl radical having from 1 to 12 carbon atoms.

The term "heterocyclic radical" preferably means a morpholino, pyrrolidino, piperidino, piperazino, 2-oxopiperid-1-yl or 2-oxopyrrolidin-1-yl radical, optionally substituted by at least one alkyl radical having from 1 to 12 carbon atoms, an alkoxy radical, an aryl radical, a nitro function, a polyether radical, a heteroaryl radical, a benzoyl radical, an alkyl ester group, a carboxylic acid, a hydroxyl optionally protected with an acetyl or benzoyl group or an amino radical optionally protected with an acetyl or benzoyl group or optionally substituted by at least one alkyl radical having from 1 to 12 carbon atoms.

The term "alkyl ester radical" means a carboxylate function substituted by an alkyl radical having from 1 to 6 carbon atoms.

Exemplary compounds of formula (I) according to the present invention, whether alone or as a mixture, include:

1. (E)-3-[3'-(3-heptyl-1-methylureido)biphenyl-4-yl]acrylic acid,
2. 3-[3'-(3-heptyl-1-methylureido)biphenyl-4-yl]propanoic acid,
3. 3-[3-fluoro-3'-(3-heptyl-1-methylureido)biphenyl-4-yl]propanoic acid,
4. 3-(3'-{3-[2-(4-fluorophenyl)ethyl]-1-methylureido}biphenyl-4-yl)propanoic acid,
5. 3-[3'-(1-methyl-3-pentylureido)biphenyl-4-yl]propanoic acid,
6. 3-[3'-(3-heptyl-1-methylureido)biphenyl-4-yl]-N-hydroxypropionamide,
7. 3-[3'-(1-methyl-3-naphthalen-2-ylureido)biphenyl-4-yl]propanoic acid,
8. 3-[3'-(3-heptyl-1-methylthioureido)biphenyl-4-yl]propanoic acid,
9. (E)-3-[2-fluoro-3'-(3-heptyl-1-methylureido)biphenyl-4-yl]acrylic acid,
10. 3-[2-fluoro-3'-(3-heptyl-1-methylureido)biphenyl-4-yl]propanoic acid,
11. 3-[3'-(3-hexyl-1-methylureido)biphenyl-4-yl]propanoic acid,
12. 3-[3'-(3-octyl-1-methylureido)biphenyl-4-yl]propanoic acid,
13. 3-{3'-[3-(4-benzyloxyphenyl)-1-methylureido]biphenyl-4-yl}propanoic acid,
14. 3-{3'-[3-(4-butylphenyl)-1-methylureido]biphenyl-4-yl}propanoic acid,
15. 3-[3'-(3-heptyl-1-methylureido)-2-(2-methoxyethoxy)biphenyl-4-yl]propanoic acid,
16. 3-[3'-(3-heptyl-1-methylureido)-2-(3-methylbutoxy)biphenyl-4-yl]propanoic acid, 17. 3-[2-(3-chloropropoxy)-3'-(3-heptyl-1-methylureido)biphenyl-4-yl]propanoic acid,
18. 3-[3'-(3-heptyl-1-methylureido)-2-methoxybiphenyl-4-yl]propanoic acid,
19. 3-[3'-(3-heptyl-1-methylureido)-2-methylbiphenyl-4-yl]propanoic acid,
20. 3-[3'-[1-methyl-3-(3-phenylpropyl)ureido]piphenyl-4-yl]propanoic acid,
21. (E)-3-[5'-(3-heptyl-1-methylureido)-2'-methylbiphenyl-4-yl]acrylic acid,
22. 3-[5'-(3-heptyl-1-methylureido)-2'-methylbiphenyl-4-yl]propanoic acid,
23. (E)-3-[3-fluoro-3'-(3-heptyl-1-methylureido)biphenyl-4-yl]acrylic acid,
24. (E)-3-[2-benzyloxy-3'-(3-heptyl-1-methylureido)biphenyl-4-yl]acrylic acid,
25. 3-[3'-(3-heptyl-1-methylureido)-2-propoxybiphenyl-4-yl]propanoic acid,
26. 3-[2-butoxy-3'-(3-heptyl-1-methylureido)biphenyl-4-yl]propanoic acid,
27. (E)-3-[3'-(1-ethyl-3-heptylureido)biphenyl-4-yl]acrylic acid,
28. (E)-3-[3'-(3-heptyl-1-propylureido)biphenyl-4-yl]acrylic acid,
29. (E)-3-[3,5-difluoro-3'-(3-heptyl-1-methylureido)biphenyl-4-yl]acrylic acid,
30. 3-[3'-(1-ethyl-3-heptylureido)biphenyl-4-yl]propanoic acid,
31. 3-[3'-(3-heptyl-1-propylureido)biphenyl-4-yl]propanoic acid,
32. 3-[3,5-difluoro-3'-(3-heptyl-1-methylureido)biphenyl-4-yl]propanoic acid,
33. 3-{3'-[3-(4-butoxyphenyl)-1-methylureido]biphenyl-4-yl}propanoic acid,
34. 3-{3'-[3-(4-butoxyphenyl)-1-ethylureido]biphenyl-4-yl}propanoic acid,
35. 3-[2-cyclopropylmethoxy-3'-(3-heptyl-1-methylureido)biphenyl-4-yl]propanoic acid,
36. 3-[2-ethoxy-3'-(3-heptyl-1-methylureido)biphenyl-4-yl]propanoic acid,
37. 3-[3'-(3-heptyl-1-methylureido)-2-(3,3,3-trifluoropropoxy)biphenyl-4-yl]propanoic acid,
38. 3-[3'-(3-heptyl-1-methylureido)-2-(4,4,4-trifluorobutoxy)biphenyl-4-yl]propanoic acid,
39. 3-[3'-(3-heptyl-1-methylureido)-2-(3-hydroxypropoxy)biphenyl-4-yl]propanoic acid,
40. 3-[3'-(3-heptyl-1-methylureido)-2-(4-hydroxybutoxy)biphenyl-4-yl]propanoic acid,
41. 3-[2-butoxy-3'-(1-methyl-3-pentylureido)biphenyl-4-yl]propanoic acid,
42. 3-[2-benzyloxy-3'-(3-heptyl-1-methylureido)biphenyl-4-yl]propanoic acid,
43. 3-[2-(3-fluorobenzyloxy)-3'-(3-heptyl-1-methylureido)biphenyl-4-yl]propanoic acid,
44. 3-[2-(4-fluorobenzyloxy)-3'-(3-heptyl-1-methylureido)biphenyl-4-yl]propanoic acid,
45. 3-[3'-(3-heptyl-1-methylureido)-2-pentyloxybiphenyl-4-yl]propanoic acid,
46. 3-[3'-(1-methyl-3-pentylureido)-2-pentyloxybiphenyl-4-yl]propanoic acid,
47. 3-[2-(2-ethoxyethoxy)-3'-(3-heptyl-1-methylureido)biphenyl-4-yl]propanoic acid,
48. 3-[2-butoxy-3'-(1-methyl-3-phenylureido)biphenyl-4-yl]propanoic acid,
49. 3-[2-(2-ethoxyethoxy)-3'-(1-methyl-3-pentylureido)biphenyl-4-yl]propanoic acid,
50. 3-[2-(2-diethylaminoethoxy)-3'-(3-heptyl-1-methylureido)biphenyl-4-yl]propanoic acid hydrochloride,
51. 3-[3'-(3-heptyl-1-methylureido)-2-(2-morpholin-4-ylethoxy)biphenyl-4-yl]propanoic acid,
52. 3-[2-amino-3'-(1-methyl-3-pentylureido)biphenyl-4-yl]propanoic acid,
53. 3-[2-butylamino-3'-(1-methyl-3-pentylureido)biphenyl-4-yl]propanoic acid hydrochloride,
54. 3-[2-benzylamino-3'-(1-methyl-3-pentylureido)biphenyl-4-yl]propanoic acid hydrochloride,
55. 3-[2-diethylamino-3'-(1-methyl-3-pentylureido)biphenyl-4-yl]propanoic acid hydrochloride,
56. 3-[3'-(1-methyl-3-pentylureido)-2-propylaminobiphenyl-4-yl]propanoic acid hydrochloride,
57. 3-[2-(4-fluorobenzylamino)-3'-(1-methyl-3-pentylureido)biphenyl-4-yl]propanoic acid hydrochloride,
58. 3-[2-butylamino-3'-(3-heptyl-1-methylureido)biphenyl-4-yl]propanoic acid hydrochloride,
59. 3-[2-benzylamino-3'-(3-heptyl-1-methylureido)biphenyl-4-yl]propanoic acid hydrochloride,
60. 3-[2-diethylamino-3'-(3-heptyl-1-methylureido)biphenyl-4-yl]propanoic acid hydrochloride,
61. 3-[3'-(3-heptyl-1-methylureido)-2-propylaminobiphenyl-4-yl]propanoic acid hydrochloride,
62. 3-[2-(4-fluorobenzylamino)-3'-(3-heptyl-1-methylureido)biphenyl-4-yl]propanoic acid hydrochloride,
63. 3-[3'-(1-methyl-3-pentylureido)biphenyl-4-yl]acrylic acid,
64. 3-[3'-(3-pentyl-1-propylureido)biphenyl-4-yl]acrylic acid,
65. 3-[4'-fluoro-3'-(1-methyl-3-pentylureido)biphenyl-4-yl]propanoic acid,
66. ethyl 3-[3'-(1-methyl-3-pentylureido)biphenyl-4-yl]acrylate,
67. 3-[3'-(1-methyl-3-naphthalen-2-ylureido)biphenyl-4-yl]acrylic acid,
68. 3-{3'-[3-(4-fluorophenyl)-1-methylureido]biphenyl-4-yl}acrylic acid,
69. 3-(3'-{3-[2-(4-fluorophenyl)ethyl]-1-methylureido}biphenyl-4-yl)acrylic acid,
70. 3-[3'-(3-benzyl-1-methylureido)biphenyl-4-yl]propanoic acid,
71. 3-[3'-(3-cyclopropylmethyl-1-methylureido)biphenyl-4-yl]propanoic acid,
72. 3-[3'-(3-cyclohexyl-1-methylureido)biphenyl-4-yl]propanoic acid,
73. 3-[3'-(3-cyclohexyl-1-methylureido)biphenyl-4-yl]acrylic acid,
74. 3-[3'-(3-cyclopropylmethyl-1-methylureido)biphenyl-4-yl]acrylic acid,
75. ethyl 4-{3-[4'-(2-carboxyethyl)biphenyl-3-yl]-3-methylureido}piperidine-1-carboxylate,
76. 3-[3'-(1-methyl-3-pyrid-3-ylureido)biphenyl-4-yl]acrylic acid,
77. 3-[3'-(1-methyl-3-pyrid-3-ylureido)biphenyl-4-yl]propanoic acid,
78. 3-{3'-[3-(6-methoxypyrid-3-yl)-1-methylureido]biphenyl-4-yl}acrylic acid,
79. 3-[3'-(1-methyl-3-propylureido)biphenyl-4-yl]acrylic acid,
80. 3-[3'-(3-hexyl-1-methylthioureido)biphenyl-4-yl]propanoic acid,
81. 3-[3'-(3-hexyl-1-methylthioureido)biphenyl-4-yl]acrylic acid,
82. methyl 3-[3'-(3-Heptyl-1-methylthioureido)biphenyl-4-yl]acrylate, 83. 3-[2-methyl-3'-(1-methyl-3-pentylureido)biphenyl-4-yl]propanoic acid,
84. 3-[3-hydroxy-3'-(1-methyl-3-pentylureido)biphenyl-4-yl]propanoic acid,
85. 3-[3-methoxymethoxy-3'-(1-methyl-3-pentylureido)biphenyl-4-yl]propanoic acid,
86. 3-[3'-(1-methyl-3-pentylureido)-2-trifluoromethylbiphenyl-4-yl]propanoic acid,
87. 3-[3'-(3-heptyl-1-methylureido)-3-methoxybiphenyl-4-yl]propanoic acid,
88. 3-{3'-[1-methyl-3-(4-propylphenyl)ureido]biphenyl-4-yl}propanoic acid,
89. 3-{3'-[1-methyl-3-(4-propylphenyl)ureido]biphenyl-4-yl}acrylic acid,
90. phenyl 3-{3'-[1-methyl-3-(4-propylphenyl)ureido]biphenyl-4-yl}acrylate,
91. benzyl 3-{3'-[1-methyl-3-(4-propylphenyl)ureido]biphenyl-4-yl}acrylate,
92. 3-[3'-(3-pentylureido)biphenyl-4-yl]acrylic acid,
93. N-hydroxy-3-{3'-[1-methyl-3-(3-phenylpropyl)ureido]biphenyl-4-yl}propionamide,
94. 3-[3'-(3-heptyl-1-methylureido)-2-hydroxybiphenyl-4-yl]propanoic acid,
95. 3-[2-cyclohexylmethoxy-3'-(3-heptyl-1-methylureido)biphenyl-4-yl]propionic acid,
96. 3-[2-cyclopentylmethoxy-3'-(3-heptyl-1-methylureido)biphenyl-4-yl]propionic acid,
97. 3-[2-cyclobutylmethoxy-3'-(3-heptyl-1-methylureido)biphenyl-4-yl]-N-hydroxypropionamide,
98. 3-[3'-(3-heptyl-1-methylureido)-2-(3-trifluoromethylbenzyloxy)biphenyl-4-yl]propanoic acid,
99. 3-[3'-(3-heptyl-1-methylureido)-2-(4-trifluoromethylbenzyloxy)biphenyl-4-yl]propanoic acid,
100. 3-[2-(3-carbamoylbenzyloxy)-3'-(3-heptyl-1-methylureido)biphenyl-4-yl]propanoic acid,
101. 3-[3'-(3-heptyl-1-methylureido)-2-(2-piperazin-1-ylethoxy)biphenyl-4-yl]propanoic acid,
102. 3-[3'-(3-heptyl-1-methylureido)-2-(2-pyrrolidin-1-ylethoxy)biphenyl-4-yl]propanoic acid,
103. 3-(2-(3-methoxybenzyloxy)-3'-{3-[2-(3-methoxyphenyl)ethyl]-1-methylureido}biphenyl-4-yl)propanoic acid,
104. 3-(2-(4-tert-butylbenzyloxy)-3'-{1-methyl-3-[2-(3-phenoxyphenyl)ethyl]-ureido}biphenyl-4-yl)propanoic acid,
105. 3-{2-(3,5-dimethoxybenzyloxy)-3'-[1-methyl-3-(3-phenoxyphenyl)ureido]biphenyl-4-yl}propanoic acid,
106. 3-[3'-[1-methyl-3-(4-phenoxyphenyl)ureido]-2-(3-trifluoromethylbenzyloxy)biphenyl-4-yl]propanoic acid,
107. 3-(2-(3-isopropoxybenzyloxy)-3'-{3-[2-(4-methoxyphenyl)ethyl]-1-methylureido}biphenyl-4-yl)propanoic acid,
108. 3-(2'-(3-methoxybenzyloxy)-5'-{3-[2-(3-methoxyphenyl)ethyl]-1-methylureido}biphenyl-4-yl)propanoic acid,
109. 3-[2'-cyclohexylmethoxy-5'-(1-methyl-3-pentylureido)biphenyl-4-yl]propanoic acid,
110. 3-[4'-ethoxy-3'-(1-methyl-3-pentylureido)-2-propoxybiphenyl-4-yl]propanoic acid,
111. 3-[3,5-dimethoxy-3'-(1-methyl-3-pentylureido)biphenyl-4-yl]propanoic acid,
112. 3-(3,5-diethoxy-3'-{3-[2-(3-methoxyphenyl)ethyl]-1-methylureido}biphenyl-4-yl)propanoic acid,
113. 3-(3'-{3-[2-(4-methoxyphenyl)ethyl]-1-methylureido}-3-propoxybiphenyl-4-yl)propanoic acid,
114. 3-[3-cyclopropylmethoxy-3'-(1-methyl-3-pentylureido)biphenyl-4-yl]propanoic acid,
115. 3-[3-ethoxy-4'-fluoro-3'-(1-methyl-3-pentylureido)biphenyl-4-yl]propanoic acid,
116. 3-[3'-(1-methyl-3-pentylureido)-3-(4,4,4-trifluorobutoxy)biphenyl-4-yl]propanoic acid,
117. 3-[3-benzyloxy-3'-(1-methyl-3-pentylureido)biphenyl-4-yl]propanoic acid,
118. 3-[3'-{3-[2-(4-methoxyphenyl)ethyl]-1-methylureido}-3-(3-trifluoromethylbenzyloxy)biphenyl-4-yl]propanoic acid,
119. 3-(3'-{3-[2-(3-methoxyphenyl)ethyl]-1-methylureido}-3,5-dipropylbiphenyl-4-yl)propanoic acid,
120. 3-[3-(2,2-dimethylpropyl)-3'-(1-methyl-3-pentylureido)biphenyl-4-yl]propanoic acid,
121. 3-[3,5-dimethyl-3'-(1-methyl-3-pentylureido)biphenyl-4-yl]propanoic acid,
122. 3-[4''-methoxy-3-(1-methyl-3-pentylureido)[1,1';3',1'']terphenyl-4'-yl]propanoic acid,
123. 3-[3''-methoxy-3-(1-methyl-3-pentylureido)[1,1';2',1'']terphenyl-4'-yl]propanoic acid,
124. 3-(3-{3-[2-(3-methoxyphenyl)ethyl]-1-methylureido}-3''-trifluoromethyl[1,1';2',1'']terphenyl-4'-yl)propanoic acid,
125. 3-{3'-(3-butyl-1-methylureido)-2-[2-(3-isopropoxyphenyl)ethyl]biphenyl-4-yl}propanoic acid,
126. 3-{3'-(1-methyl-3-pentylureido)-2-[(pyrid-3-ylmethyl)amino]biphenyl-4-yl}propanoic acid,
127. 3-[3-(2-methoxyethylamino)-3'-(1-methyl-3-pentylureido)biphenyl-4-yl]propanoic acid,
128. methyl 3-[3,5-diethyl-3'-(1-methyl-3-pentylureido)biphenyl-4-yl]propanoate,
129. methyl 3-[3'-[1-methyl-3-(3-phenoxyphenyl)ureido]-2-(3-trifluoromethylbenzyloxy)biphenyl-4-yl]propanoate,
130. methyl 3-[3'-[3-(2-biphenyl-4-ylethyl)-1-methylureido]-2-(3-methoxybenzyloxy)biphenyl-4-yl]propanoate,
131. ethyl 3-[3'-{3-[2-(3-methoxyphenyl)ethyl]-1-methylureido}-2-(4,4,4-trifluorobutoxy)biphenyl-4-yl]propanoate.

The compounds of formula (I) that are more particularly preferred are those that satisfy at least one of the following conditions:
R1 is a hydroxyl or hydroxylamine radical;
R2 and R7 are each an alkoxy or aryloxy radical, an alkylamino radical or a polyether radical;
R3 and R8 are each a hydrogen atom;
R4 is a lower alkyl radical having from 1 to 4 carbon atoms;
R5 is an alkyl radical having from 3 to 8 carbon atoms;
Y is an oxygen atom;
the bond V—W is a single or double C—C bond.

In particular, more preferred are the compounds of general formula (I) that satisfy all of the following conditions:
R1 is a hydroxyl or hydroxylamine radical;
R2 and R7 are each an alkoxy or aryloxy radical, an alkylamino radical or a polyether radical;
R3 and R8 are each a hydrogen atom;
R4 is a lower alkyl radical having from 1 to 4 carbon atoms;
R5 is an alkyl radical having from 3 to 8 carbon atoms;
Y is an oxygen atom;
the bond V—W is a single or double C—C bond.

Figure 2:
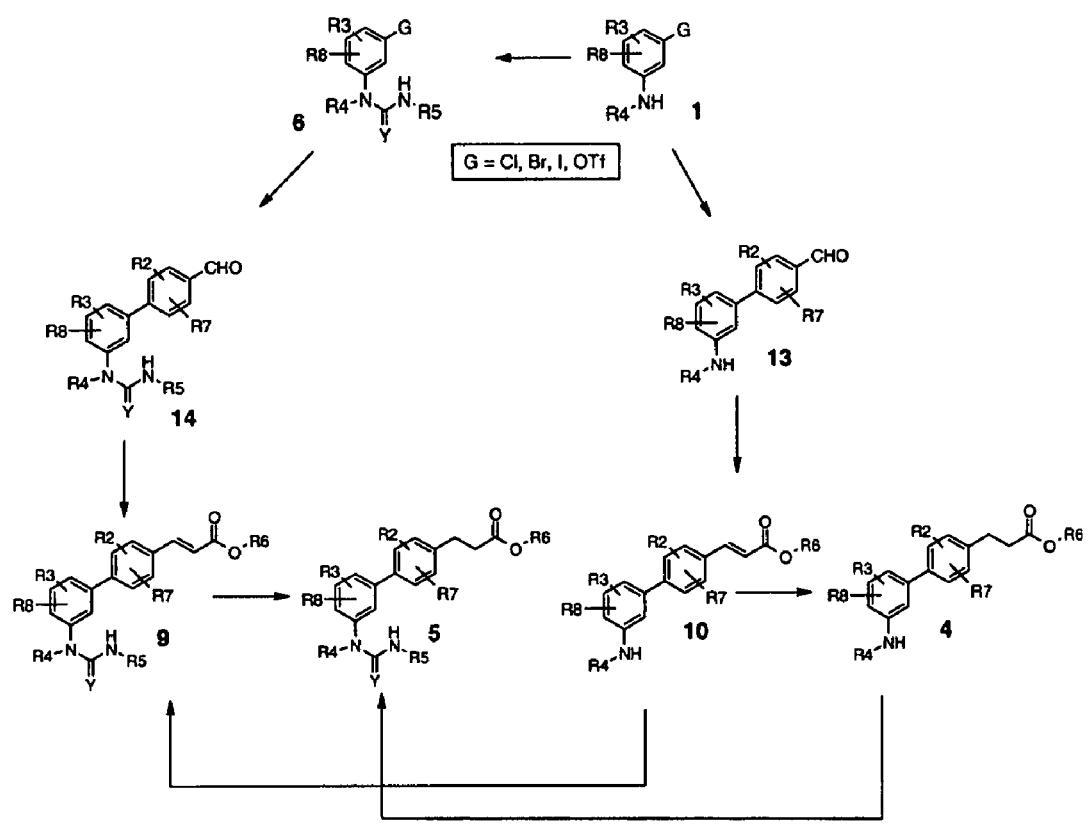
Figure 3:
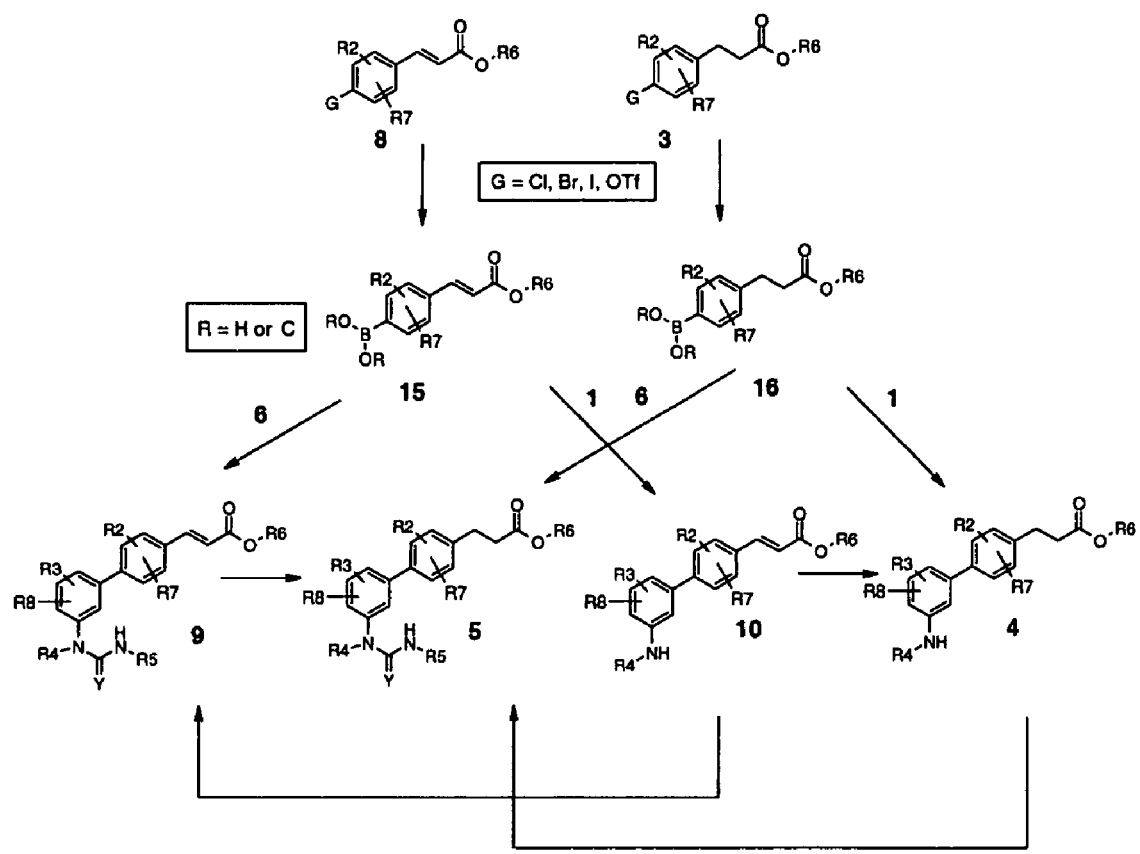

The present invention also features processes for preparing the compounds of formula (I), in particular according to the reaction schemes shown in FIGS. 1, 2 and 3.

FIG. 1:

The boronic acid 2 may be obtained from compound 1 under standard conditions, for example by reaction with tert-butyllithium, followed by an addition to trimethyl borate.

A Suzuki type palladium coupling from the boronic acid 2 and compound 3 (selected from an aryl bromide, iodide, chloride or triflate) makes it possible to obtain the compound having the aryl-aryl sequence 4.

A Suzuki type palladium coupling from the boronic acid 2 and compound 8 (selected from an aryl bromide, iodide, chloride or triflate) makes it possible to obtain the compound having the aryl-aryl sequence 10.

Compound 4 may be coupled with isocyanates or isothiocyanates under standard conditions to give compound 5.

Compound 10 may be coupled with isocyanates or isothiocyanates under standard conditions to give compound 9.

When it is desired to obtain a compound with R1 being a hydroxyl radical (compound 12), the acid function may be obtained from compound 5 either:

by saponification, if R6 is an alkyl chain, with a base such as sodium hydroxide; or by hydrogenolysis if R6 is a benzyl; or by deprotection with palladium if R6 is an allyl chain.

Compound 1 may also be coupled directly with an isocyanate or an isothiocyanate under standard conditions to give compound 6.

The boronate 7 may be obtained by treating compound 6 with pinacol diborane, for example in the presence of a palladium-based catalyst, for instance diphenylphosphinoferrocenepalladium dichloride.

A Suzuki type palladium coupling from the boronate 7 and compound 8 (selected from an aryl bromide, iodide, chloride or triflate) makes it possible to obtain the compound having the aryl-aryl sequence 9.

A Suzuki type palladium coupling from the boronate 7 and compound 3 (selected from an aryl bromide, iodide, chloride or triflate) makes it possible to obtain the compound having the aryl-aryl sequence 5.

Compound 5 may be obtained by hydrogenation of compound 9 under standard hydrogenation conditions, for instance: hydrogen catalyzed with palladium-on-charcoal.

When R2 is a benzyloxy, compound 20 may be obtained from 9 under standard hydrogenation conditions, for instance: hydrogen catalyzed with palladium-on-charcoal.

Compound 21 may be obtained from 20 by alkylation of the phenol, for example using a base such as potassium carbonate in the presence of an alkyl halide.

The acid function of compound 12 may be obtained from 21 by saponification if R6 is an alkyl chain, with a base, for instance sodium hydroxide.

When R2 is a nitro, compound 9 may be converted into the amine 19 by hydrogenation, for example in the presence of palladium-on-charcoal and hydrogen.

Compound 19 may then react with aldehydes in the presence of sodium borohydride to form alkylamino or dialkylamino compounds, which may then be saponified into the corresponding acids thereof 12, for example using sodium hydroxide.

Compound 4 may be obtained by hydrogenation of compound 10 under standard hydrogenation conditions, for instance: hydrogen catalyzed with palladium-on-charcoal.

The acid function of compound 11 may be obtained from 9: by saponification if R6 is an alkyl chain, with a base such as sodium hydroxide; or by deprotection with palladium if R6 is an allyl chain.

Compound 12 may be obtained by hydrogenation of compound 11 under standard hydrogenation conditions, for instance: hydrogen catalyzed with palladium-on-charcoal.

Compound 17 may be obtained from the acid 12 by treatment with oxalyl chloride, for example, followed by treatment with hydroxylamine.

Compound 18 may be obtained from the acid 11 by treatment with oxalyl chloride, for example, followed by treatment with hydroxylamine.

Compound 17 may be obtained from compound 5 by treatment with hydroxylamine.

Compound 18 may be obtained from compound 9 by treatment with hydroxylamine.

FIG. 2:

A Suzuki type palladium coupling from the 4-formylphenylboronic acids and compound 1 (selected from an aryl bromide, iodide, chloride or triflate) makes it possible to obtain the compound having the aryl-aryl sequence 13.

A Suzuki type palladium coupling from the 4-formylphenylboronic acids and compound 6 (selected from an aryl bromide, iodide, chloride or triflate) makes it possible to obtain the compound having the aryl-aryl sequence 14.

Compound 9 may be obtained via a Wittig reaction from compound 14 via the action of methyltriphenylphosphoranylidene acetate, for example.

Compound 10 may be obtained via a Wittig reaction from compound 13 via the action of methyltriphenylphosphoranylidene acetate, for example.

The remainder of the synthetic routes is as described for FIG. 1.

FIG. 3:

The boronate 15 may be obtained by treating compound 8 with pinacol diborane, for example in the presence of a palladium-based catalyst, for instance diphenylphosphinoferrocenepalladium dichloride.

The boronate 16 may be obtained by treating compound 3 with pinacol diborane, for example in the presence of a palladium-based catalyst, for instance diphenylphosphinoferrocenepalladium dichloride.

A Suzuki type palladium coupling from compound 15 and compound 6 (selected from an aryl bromide, iodide, chloride or triflate) makes it possible to obtain the compound having the aryl-aryl sequence 9.

A Suzuki type palladium coupling from compound 15 and compound 1 (selected from an aryl bromide, iodide, chloride or triflate) makes it possible to obtain the compound having the aryl-aryl sequence 10.

A Suzuki type palladium coupling from compound 16 and compound 1 (selected from an aryl bromide, iodide, chloride or triflate) makes it possible to obtain the compound having the aryl-aryl sequence 4.

A Suzuki type palladium coupling from compound 16 and compound 6 (selected from an aryl bromide, iodide, chloride or triflate) makes it possible to obtain the compound having the aryl-aryl sequence 5.

The remainder of the synthetic routes is as described for FIG. 1.

The compounds according to the invention have modulatory properties on PPAR type receptors. This activity on the PPARα, δ and γ receptors is measured in a transactivation test and quantified by means of the dissociation constant Kdapp (apparent), as described in Example 63.

The preferred compounds of the present invention have a dissociation constant of less than or equal to 5,000 nM and advantageously less than or equal to 1,000 nM.

Preferably, the compounds are specific PPARγ type receptor modulators, i.e., they have a ratio from the Kdapp for the PPARα or PPARδ receptors and the Kdapp for the PPARγ receptors, of greater than or equal to 10. Preferably, this PPARα/PPARγ or PPARδ/PPARγ ratio is greater than or equal to 50 and more advantageously greater than or equal to 100.

The present invention also features administration of the compounds of formula (I) as medicaments.

Thus, the compounds according to the invention are useful for regulating and/or restoring skin lipid metabolism.

The compounds according to the invention are particularly useful in the following fields of treatment, whether regime or regimen:

1) for treating dermatological complaints, conditions or afflictions associated with a keratinization disorder relating to cell differentiation and proliferation, especially for treating common acne, comedones, polymorphs, acne rosacea, nodulocystic acne, acne conglobata, senile acne, and secondary acnes such as solar acne, medication-related acne or occupational acne;

2) for treating other types of keratinization disorders, especially ichthyosis, ichthyosiform conditions, Darier's disease, palmoplantar keratoderma, leukoplakia and leukoplakiform conditions, and cutaneous or mucous (buccal) lichen;

3) for treating other dermatological complaints, conditions or affliction having an inflammatory immunoallergic component, with or without cell proliferation disorder, and especially all forms of psoriasis, whether cutaneous, mucous or ungual, and even psoriatic rheumatism, or cutaneous atopy, such as eczema, or respiratory atopy, or, alternatively, gingival hypertrophy;

4) for treating all dermal or epidermal proliferations, whether benign or malignant, and whether of viral origin or otherwise, such as common warts, flat warts and verruciform epidermodysplasia, oral or florid papillomatoses, T lymphoma, and proliferations that may be induced by ultraviolet radiation, especially in the case of basal cell and spinal cell epithelioma, and also any precancerous skin lesion such as keratoacanthomas;

5) for treating other dermatological disorders, conditions or afflictions, such as immune dermatoses, such as lupus erythematosus, immune bullous diseases and collagen diseases, such as scleroderma;

6) in the treatment of dermatological or general complaints or conditions having an immunological component;

7) in the treatment of skin disorders caused by exposure to UV radiation, and also for repairing or combating aging of the skin, whether photoinduced or chronological aging, or for reducing actinic pigmentations and keratosis, or any pathology associated with chronological or actinic aging, such as xerosis;

8) for combating sebaceous function disorders, such as the hyperseborrhoea of acne or simple seborrhoea;

9) for preventing or treating cicatrization disorders, or for preventing or repairing stretch marks;

10) in the treatment of pigmentation disorders, such as hyperpigmentation, melasma, hypopigmentation or vitiligo;

11) in the treatment of lipid metabolism complaints or conditions, such as obesity, hyperlipidaemia, or non-insulin-dependent diabetes;

12) in the treatment of inflammatory complaints or conditions, such as arthritis;

13) in the treatment or prevention of cancerous or precancerous conditions;

14) in the prevention or treatment of alopecia of various origins, especially alopecia caused by chemotherapy or radiation;

15) in the treatment of disorders of the immune system, such as asthma, type I sugar diabetes, multiple sclerosis or other selective dysfunctions of the immune system; and 16) in the treatment of complaints or conditions of the cardiovascular system, such as arteriosclerosis or hypertension.

This invention also features cosmetic/pharmaceutical compositions comprising, formulated into a physiologically acceptable medium, at least one compound of formula (I) as defined above.

The present invention also features administration of the compounds of formula (I) for treating the abovementioned complaints, conditions or afflictions in particular for regulating and/or restoring skin lipid metabolism.

The compositions according to the invention may be administered orally, enterally, parenterally, topically or ocularly. The pharmaceutical composition is preferably packaged in a form that is suitable for topical application.

Via the oral route, the composition, more particularly the pharmaceutical composition, may be in the form of tablets, gel capsules, dragees, syrups, suspensions, solutions, powders, granules, emulsions, lipid or polymeric microspheres, nanospheres or vesicles allowing a controlled release. Via the parenteral route, the composition may be in the form of solutions or suspensions for infusion or for injection.

The compounds according to the invention are generally administered at a daily dose of about 0.001 mg/kg to 100 mg/kg of body weight, in 1 to 3 dosage intakes.

The compounds are administered systemically, at a concentration generally of from 0.001% to 10% by weight and preferably from 0.01% to 1% by weight, relative to the weight of the composition.

Via the topical route, the pharmaceutical compositions according to the invention are more particularly useful for treating the skin and mucous membranes and may be in the form of ointments, creams, milks, pomades, powders, impregnated pads, solutions, gels, sprays, lotions or suspensions. They may also be in the form of lipid or polymeric microspheres, nanospheres or vesicles or polymer patches and hydrogels allowing a controlled release. The topical compositions may be in anhydrous form, in aqueous form or in the form of an emulsion.

The compounds are administered topically at a concentration generally of from 0.001% to 10% by weight and preferably from 0.01% to 1% by weight, relative to the total weight of the composition.

The compounds of formula (I) according to the invention also find an application in cosmetics, in particular in body and hair hygiene and more particularly for regulating and/or restoring skin lipid metabolism.

A subject of the invention is thus also the cosmetic use of a composition comprising, in a physiologically acceptable support, at least one of the compounds of formula (I) for body or hair hygiene.

The cosmetic compositions according to the invention containing, in a cosmetically acceptable support, at least one compound of formula (I) or an optical or geometrical isomer thereof or a salt thereof, may especially be in the form of a cream, a milk, a lotion, a gel, lipid or polymeric microspheres, nanospheres or vesicles, a soap or a shampoo.

The concentration of compound of formula (I) in the cosmetic compositions is from 0.001% to 3% by weight relative to the total weight of the composition.

The compositions as described above may of course also contain inert or even pharmacodynamically active additives or combinations of these additives, and especially: wetting agents, depigmenting agents such as hydroquinone, azelaic acid, caffeic acid or kojic acid; emollients; moisturizers, for instance glycerol, PEG-400, thiamorpholinone and derivatives thereof, or, alternatively, urea; anti-seborrhoeic or anti-acne agents, such as S-carboxymethylcysteine or S-benzylcysteamine, and salts or derivatives thereof, or benzoyl peroxide; anti-fungal agents such as ketoconazole or 4,5-polymethylene-3-isothiazolidones; anti-bacterial agents, carotenoids and especially β-carotene; anti-psoriatic agents such as anthralin and derivatives thereof; eicosa-5,8,11,14-tetraynoic and eicosa-5,8,11-triynoic acids, esters and amides thereof, and, finally, retinoids. The compounds of formula (I) may also be combined with D vitamins or derivatives thereof, with corticosteroids, with free-radical scavengers, α-hydroxy or α-keto acids or derivatives thereof, or, alternatively, with ion-channel blockers.

These compositions may also contain flavor enhancers, preservatives such as para-hydroxybenzoic acid esters, stabilizers, moisture regulators, pH regulators, osmotic pressure modifiers, emulsifiers, UV-A and UV-B screening agents, and anti-oxidants such as α-tocopheryl, butylhydroxyanisole or butylhydroxytoluene.

Of course, one skilled in this art will take care to select the optional compound(s) to be added to these compositions such that the advantageous properties intrinsically associated with the present invention are not, or are not substantially, adversely affected by the envisaged addition.

In order to further illustrate the present invention and the advantages thereof, the following examples of specific active compounds are given, as are the results of the biological activities of such compounds and specific formulations thereof, it being understood that same are intended only as illustrative and in nowise limitative. In said examples to follow, all parts and percentages are given by weight, unless otherwise indicated.

Example 1

Synthesis of (E)-3-[3'-(3-heptyl-1-methylureido)biphenyl-4-yl]acrylic acid

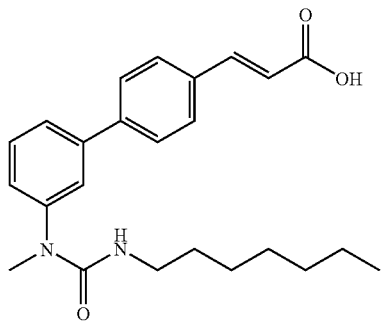

a. Preparation of tert-butyl (3-bromophenyl)carbamate

To a mixture of 94 g (549 mmol) of 3-bromoaniline in 1 l of dichloromethane are added portionwise 120 g (549 mmol) of di-tert-butyl dicarbonate, at room temperature. After stirring for 18 hours, the reaction medium is poured into ice-cold water and then extracted with dichloromethane. The organic phase is separated out after settling of the phases, dried over magnesium sulfate and evaporated. 138 g of (3-tert-butyl bromophenyl)carbamate are obtained in a yield of 98%.

b. Preparation of tert-butyl (3-bromophenyl)-N-methylcarbamate

To a solution of 114 g (447 mmol) of tert-butyl (3-bromophenyl)carbamate in 800 ml of DMF are added portionwise 19 g (475 mmol) of sodium hydride (60% in oil) and the reaction medium is stirred until the evolution of gas has ceased. 29.3 ml (470 mmol) of methyl iodide are added dropwise and stirring is continued for 18 hours. The reaction medium is poured into ice-cold water and extracted with ethyl acetate. The organic phase is separated out after settling of the phases, dried over magnesium sulfate and evaporated. 115 g of tert-butyl (3-bromophenyl)-N-methylcarbamate are obtained in a yield of 95%.

c. Preparation of (3-bromophenyl)methylamine 5 mL of trifluoromethanesulfonic acid are added to a solution of 3.6 g (12.7 mmol) of (3-tert-butyl bromophenyl)-N-methylcarbamate in 15 mL of dichloromethane. The reaction medium is stirred for 1 hour at room temperature (r.t.). The reaction is stopped by addition of 50 mL of saturated sodium hydrogen carbonate solution and then extracted with ethyl acetate. The solvents are evaporated off and the residue is then chromatographed on silica gel. Eluent (1/1 heptane/ethyl acetate). 2.14 g of oil are obtained. Yield 90%.

d. Preparation of 1-(3-bromophenyl)-3-heptyl-1-methylurea 3.2 mL (20 mmol, 1.5 eq) of heptyl isocyanate are added to a solution of 2.5 g (13 mmol, 1 eq) of (3-bromophenyl)methylamine in 10 ml of tetrahydrofuran in the presence of 2 ml of triethylamine. The reaction mixture is stirred for 12 hours at r.t. The reaction is stopped by addition of 2 mL of water and then extracted with ethyl acetate. The organic phases are combined and dried over sodium sulfate. The solvents are evaporated off and the residue is then chromatographed on silica gel (70/30 heptane/ethyl acetate). 3.4 g of 1-(3-bromophenyl)-3-heptyl-1-methylurea in solid form are obtained. Yield=77% e. Preparation of 3-heptyl-1-methyl-1-[3-(4,4,5,5-tetramethyl[1,3,2]dioxaborolan-2-yl)phenyl]urea 4.0 g (15.5 mmol, 1.5 eq) of pinacol diborane are added to a mixture of 3.4 g (10 mmol, 1 eq) of 1-(3-bromophenyl)-3-heptyl-1-methylurea and 3.0 g (31 mmol, 3 eq) of potassium acetate, in the presence of 380 mg (0.5 mmol, 5 mol %) of diphenylphosphinoferrocenepalladium dichloride (PdCl$_2$dppf) in 15 ml of dimethylformamide. The mixture is stirred for 3 hours at 90° C. The reaction is stopped by addition of 50 mL of water and then extracted with ethyl acetate. The organic phases are combined and dried over sodium sulfate. The solvents are evaporated off and the residue is then chromatographed on silica gel (70/30 heptane/ethyl acetate). 2.5 g of 3-heptyl-1-methyl-1-[3-(4,4,5,5-tetramethyl[1,3,2]dioxaborolan-2-yl)phenyl]urea in oil form are obtained. Yield=64% f. Preparation of ethyl 3-[3'-(3-heptyl-1-methylureido)biphenyl-4-yl]acrylate 308 mg (0.26 mmol, 5 mol %) of tetrakis(triphenylphosphine)palladium are added to a solution of 2 g (5.34 mmol, 1.0 eq) of 3-heptyl-1-methyl-1-[3-(4,4,5,5-tetramethyl[1,3,2]dioxaborolan-2-yl)phenyl]urea and 1.6 g (6.4 mmol, 1.2 eq) of ethyl 4-bromocinnamate in 20 mL of an 8/2 mixture of dimethylformamide and of 2M potassium phosphate solution. The reaction mixture is stirred for 3 hours at 90° C. The reaction is stopped by addition of 50 mL of water and then extracted with ethyl acetate. The organic phases are combined and dried over sodium sulfate. The solvents are evaporated off and the residue is then chromatographed on silica gel (70/30 heptane/ethyl acetate). 1.69 g of ethyl 3-[3'-(3-heptyl-1-methylureido)biphenyl-4-yl]acrylate in oil form are obtained. Yield=75% g. Synthesis of 3-[3'-(3-heptyl-1-methylureido)biphenyl-4-yl]acrylic acid 1.6 g (40 mmol, 10 eq) of sodium hydroxide are added to a solution of 1.69 g (4.0 mmol, 1 eq) of ethyl 3-[3'-(3-heptyl-1-methylureido)biphenyl-4-yl]acrylate in 30 ml of 9/1 tetrahydrofuran/methanol. The reaction mixture is stirred for one hour at room temperature. The reaction is stopped by addition of 20 mL of water and 5 mL of acetic acid and then extracted with ethyl acetate. The organic phases are combined and dried over sodium sulfate. The solvents are evaporated off and the residue is then chromatographed on silica gel (70/30 heptane/ethyl acetate). The oil obtained is crystallized from Heptane/ethyl acetate. 1.29 g of 3-[3'-(3-heptyl-1-methylureido)biphenyl-4-yl]acrylic acid in the form of white crystals are obtained. (m.p.=125-126° C.) Yield=82%

$^1$H NMR (CDCl$_3$, 400 MHz): 0.86 (t, J=7.2 Hz, 3H); 1.24 (m, 8H); 1.44 (m, 2H); 3.20 (dt, J=6.0, 6.8 Hz, 2H); 3.35 (s, 3H); 4.42 (t, J=5.6 Hz, 1H); 6.54 (d, J=15.9 Hz, 1H); 7.29 (d, J=6.4 Hz, 1H); 7.55 (m, 3H); 7.65 (m, 4H); 7.84 (d, J=16 Hz, 1H).

Example 2

Synthesis of 3-[3'-(3-heptyl-1-methylureido)biphenyl-4-yl]propanoic acid

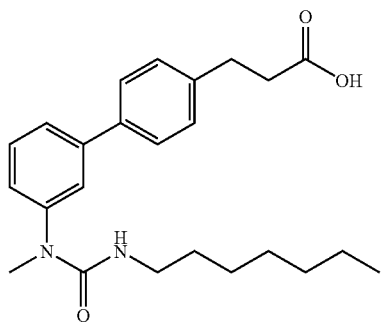

Synthesis of 3-[3'-(3-heptyl-1-methylureido)biphenyl-4-yl]propanoic acid

A solution of 900 mg (2.28 mmol) of 3-[3'-(3-heptyl-1-methylureido)biphenyl-4-yl]acrylic acid (prepared as in 1 g) in 20 ml of methanol is stirred for 4 hours at room temperature in the presence of 100 mg of 10% Pd/C under a hydrogen atmosphere. The palladium is filtered off and the solvents are evaporated off. The residue is crystallized from a dichloromethane/heptane mixture.

620 mg of 3-[3'-(3-heptyl-1-methylureido)biphenyl-4-yl]propanoic acid in the form of a white solid are obtained (m.p.=101° C.). Yield=68%

$^1$H NMR (CDCl$_3$, 400 MHz): 0.86 (t, J=7.2 Hz, 3H); 1.24 (m, 8H); 1.42 (m, 2H); 2.76 (m 2H); 3.04 (m 2H); 3.19 (m 2H); 3.33 (s, 3H); 4.42 (m, 1H); 7.22-7.35 (m, 3H); 7.48-7.54 (m, 5H).

Example 3

Synthesis of 3-[3-fluoro-3'-(3-heptyl-1-methylureido)biphenyl-4-yl]propanoic acid

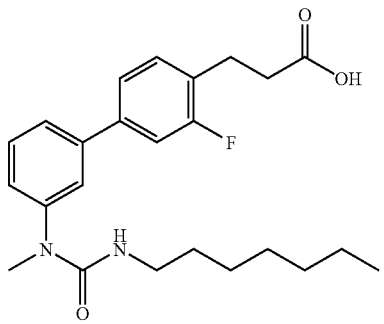

a. Preparation of methyl 3-(4-bromo-2-fluorophenyl)acrylate 2.17 g (6.5 mmol, 1.2 eq) of methyltriphenylphosphoranylidene acetate are added to a solution of 1.1 g (5.4 mmol, 1.0 eq) of 4-bromo-2-fluorobenzaldehyde in 10 ml of toluene. The reaction mixture is stirred for 1 hour at 80° C. The reaction is stopped by addition of 20 mL of water and then extracted with ethyl acetate. The organic phases are combined and dried over sodium sulfate. The solvents are evaporated off and the residue is then chromatographed on silica gel (80/20 heptane/ethyl acetate). 1.1 g of methyl 3-(4-bromo-2-fluorophenyl)acrylate in the form of a white solid are obtained. Yield=78% b. Preparation of methyl 3-[3-fluoro-3'-(3-heptyl-1-methylureido)biphenyl-4-yl]acrylate 44 mg (5 mol %) of tetrakis(triphenylphosphine)palladium are added to a solution of 200 mg (0.77 mmol, 1.0 eq) of methyl 3-(4-bromo-2-fluorophenyl)acrylate and 430 mg (1.15 mmol, 1.5 eq) of 3-heptyl-1-methyl-1-[3-(4,4,5,5-tetramethyl[1,3,2]dioxaborolan-2-yl)phenyl]urea (prepared as in 1e) in a mixture of dimethylformamide and 2M potassium phosphate solution (8/2). The reaction mixture is stirred for 2 hours at 90° C. The reaction is stopped by addition of 10 mL of water and then extracted with ethyl acetate. The organic phases are combined and dried over sodium sulfate. The solvents are evaporated off and the residue is then chromatographed on silica gel (70/30 heptane/ethyl acetate). 138 mg of methyl 3-[3-fluoro-3'-(3-heptyl-1-methylureido)biphenyl-4-yl]acrylate are obtained. Yield=42% c. Preparation of methyl 3-[3-fluoro-3'-(3-heptyl-1-methylureido)biphenyl-4-yl]propanoate A solution of 138 mg (0.32 mmol) of methyl 3-[3-fluoro-3'-(3-heptyl-1-methylureido)biphenyl-4-yl]acrylate in 3 ml of methanol is stirred for 4 hours at room temperature in the presence of 10 mg of 10% Pd/C under a hydrogen atmosphere. The palladium is filtered off and the solvents are evaporated off. The residue is chromatographed on silica gel (70/30 heptane/ethyl acetate). 130 mg of methyl 3-[3-fluoro-3'-(3-heptyl-1-methylureido)biphenyl-4-yl]propanoate are obtained. Yield=94% d. Synthesis of 3-[3-fluoro-3'-(3-heptyl-1-methylureido)biphenyl-4-yl]propanoic acid 100 mg (2.5 mmol, 8 eq) of sodium hydroxide are added to a solution of 130 mg (0.3 mmol, 1 eq) of methyl 3-[3-fluoro-3'-(3-heptyl-1-methylureido)biphenyl-4-yl]propanoate in 3 ml of 9/1 tetrahydrofuran/methanol. The reaction mixture is stirred for 3 hours at room temperature. The reaction is stopped by addition of 10 mL of water and 1 mL of acetic acid and then extracted with ethyl acetate. The organic phases are combined and dried over sodium sulfate. The solvents are evaporated off and the residue is then chromatographed on silica gel (70/30 heptane/ethyl acetate). The oil obtained is crystallized from heptane/dichloromethane. 55 mg of 3-[3-fluoro-3'-(3-heptyl-1-methylureido)biphenyl-4-yl]propanoic acid in the form of a white solid are obtained (m.p.=92-93° C.). Yield=43%

$^1$H NMR (CDCl$_3$, 400 MHz): 0.86 (t, J=7.0 Hz, 3H); 1.24 (m, 8H); 1.43 (m, 2H); 2.75 (t, J=7.6 Hz, 2H); 3.06 (t, J=7.6 Hz, 2H); 3.20 (dt, J=5.6, 7.2 Hz, 2H); 3.32 (s, 3H); 4.40 (t, J=5.6 Hz, 1H); 7.24-7.34 (m, 4H); 7.46-7.51 (m, 3H).

Example 4

Synthesis of 3-(3'-{3-[2-(4-fluorophenyl)ethyl]-1-methylureido}biphenyl-4-yl)propanoic acid

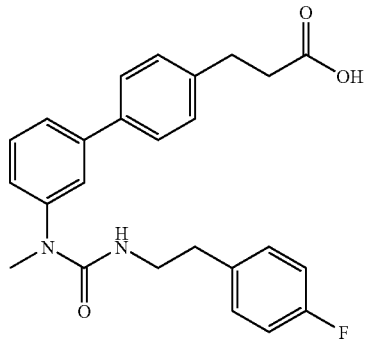

a. Preparation of N-methyl-3-aminophenylboronic acid 37.6 g (202 mmol, 1 eq) of (3-bromophenyl)methylamine (obtained as in 1c) are dissolved in 300 ml of tetrahydrofuran. The reaction mixture is cooled to −70° C., and 166 mL (242 mmol, 1.2 eq) of 1.5 M methyllithium are then added slowly while maintaining the temperature at −70° C. The reaction mixture is stirred for 1 hour at −70° C. 306 mL (444 mmol, 2.2 eq) of 1.46 M tert-butyllithium are added while maintaining the temperature at −70° C. The reaction mixture is stirred for 45 minutes at −70° C. 103.5 mL (808 mmol, 4 eq) of trimethyl borate are added at −65° C., and the reaction mixture is then warmed to room temperature. The reaction is stopped by addition of 1 L of 1N hydrochloric acid. The pH is adjusted to 5 and the reaction medium is then extracted with n-butanol. The organic phases are combined and dried over sodium sulfate. The solvents are evaporated off and the residue is then chromatographed on silica gel (70/30 heptane/ethyl acetate). 11.3 g of N-methyl-3-aminophenylboronic acid are obtained. Yield=40% b. Preparation of methyl 3-(4-hydroxyphenyl)propanoate 15 g (0.09 mol, 1 eq) of 3-(4-hydroxyphenyl)propanoic acid are dissolved in 50 ml of methanol and 4 drops of sulfuric acid are added. The reaction mixture is stirred for 16 hours at room temperature. The reaction is stopped by addition of 50 mL of saturated sodium hydrogen carbonate solution and then extracted with ethyl acetate. The organic phases are combined and dried over sodium sulfate. The solvents are evaporated off and the residue is then chromatographed on silica gel (70/30 heptane/ethyl acetate). 14.9 g of methyl 3-(4-hydroxyphenyl)propanoate are obtained. Yield=92% c. Preparation of methyl 3-(3'-methylaminobiphenyl-4-yl)propanoate 1.0 g (5.5 mmol, 1.0 eq) of methyl 3-(4-hydroxyphenyl)propanoate is dissolved in 8 mL of dichloromethane in the presence of 1 ml of triethylamine. 1.12 mL (6.6 mmol, 1.2 eq) of triflic anhydride are added at 0° C. The reaction mixture is stirred for 1 hour at 0° C. The reaction is stopped by addition of 50 mL of saturated sodium hydrogen carbonate solution and then extracted with ethyl acetate. The organic phases are combined and dried over sodium sulfate. The solvents are evaporated off and the residue is then filtered on silica gel (1/1 heptane/ethyl acetate). After evaporating off the solvents, the oil obtained is dissolved in 6 mL of an 8/2 mixture of dimethylformamide and of 2M potassium phosphate solution. 1.0 g (6.6 mmol, 1.2 eq) of N-methyl-3-aminophenylboronic acid are added, along with 317 mg of tetrakis(triphenylphosphine) palladium. The reaction mixture is stirred for 3 hours at 90° C. The reaction is stopped by addition of 50 mL of water and then extracted with ethyl acetate. The organic phases are combined and dried over sodium sulfate. The solvents are evaporated off and the residue is then chromatographed on silica gel (70/30 heptane/ethyl acetate). 0.92 g of methyl 3-(3'-methylaminobiphenyl-4-yl)propanoate is obtained. Yield=61% d. Preparation of methyl 3-(3'-{3-[2-(4-fluorophenyl)ethyl]-1-methylureido}biphenyl-4-yl)propanoate 340 µL (1.84 mmol, 2 eq) of 4-fluorophenethyl isocyanate are added to a solution of 250 mg (0.92 mmol, 1 eq) of methyl 3-(3'-methylaminobiphenyl-4-yl)propanoate in 8 mL of a 4/1 tetrahydrofuran/triethylamine mixture. The reaction mixture is stirred for 24 hours at room temperature. The reaction is stopped by addition of 10 mL of saturated ammonium chloride solution and then extracted with ethyl acetate. The organic phases are combined and dried over sodium sulfate. The solvents are evaporated off and the residue is then chromatographed on silica gel (70/30 heptane/ethyl acetate). 221 mg of methyl 3-(3'-{3-[2-(4-fluorophenyl)ethyl]-1-methylureido}biphenyl-4-yl)propanoate are obtained. Yield=55% e. Synthesis of 3-(3'-{3-[2-(4-fluorophenyl)ethyl]-1-methylureido}biphenyl-4-yl)propanoic acid 200 mg (5 mmol, 10 eq) of sodium hydroxide are added to a solution of 221 mg (0.51 mmol, 1 eq) of methyl 3-(3'-{3-[2-(4-fluorophenyl)ethyl]-1-methylureido}biphenyl-4-yl)

propanoate in 6 ml of an 8/2 tetrahydrofuran/methanol mixture. The reaction mixture is stirred for 3 hours at room temperature. The reaction is stopped by addition of 10 mL of water and 2 mL of acetic acid and then extracted with ethyl acetate. The organic phases are combined and dried over sodium sulfate. The solvents are evaporated off and the residue is then chromatographed on silica gel (70/30 heptane/ethyl acetate). 180 mg of 3-(3'-{3-[2-(4-fluorophenyl)ethyl]-1-methylureido}biphenyl-4-yl)propanoic acid are obtained (m.p.=146° C.). Yield=84%

$^1$H NMR (CDCl$_3$, 400 MHz): 2.73 (t, J=6.7 Hz, 2H); 2.76 (t, J=7.8 Hz, 2H); 3.05 (t, J=7.6 Hz, 2H); 3.31 (s, 3H); 3.43 (dt, J=6.6, 6.1 Hz, 2H); 4.39 (t, J=5.7 Hz, 1H); 6.83 (m, 2H); 7.03 (m, 2H); 7.11 (m, 1H); 7.35 (m, 3H); 7.45 (m, 4H).

Example 5

Synthesis of 3-[3'-(1-methyl-3-pentylureido)biphenyl-4-yl]propanoic acid

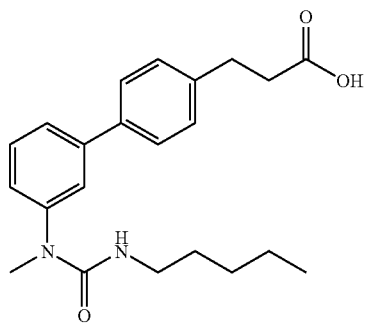

a. Preparation of methyl 3-[3'-(1-methyl-3-pentylureido)biphenyl-4-yl]propanoate 236 μL (1.84 mmol, 2 eq) of pentyl isocyanate are added to a solution of 250 mg (0.92 mmol, 1 eq) of methyl 3-(3'-methylaminobiphenyl-4-yl)propanoate (obtained as in 4c) in 5 mL of a 9/1 tetrahydrofuran/triethylamine mixture. The reaction mixture is stirred for 12 h at room temperature. The reaction is stopped by addition of 10 mL of water and then extracted with ethyl acetate. The organic phases are combined and dried over sodium sulfate. The solvents are evaporated off and the residue is then chromatographed on silica gel (70/30 heptane/ethyl acetate). 245 mg of methyl 3-[3'-(1-methyl-3-pentylureido)biphenyl-4-yl]propanoate are obtained. Yield=70% b. Synthesis of 3-[3'-(1-methyl-3-pentylureido)biphenyl-4-yl]propanoic acid 130 mg (3.2 mmol, 5 eq) of sodium hydroxide are added to a solution of 245 mg (0.64 mmol, 1 eq) of methyl 3-[3'-(1-methyl-3-pentylureido)biphenyl-4-yl]propanoate in 6 ml of a 9/1 tetrahydrofuran/methanol mixture. The reaction mixture is stirred for 2 hours at room temperature. The reaction is stopped by addition of 10 mL of water and 2 mL of acetic acid and then extracted with ethyl acetate. The organic phases are combined and dried over sodium sulfate. The solvents are evaporated off and the residue is then chromatographed on silica gel (70/30 heptane/ethyl acetate). The oil obtained is crystallized from pentane. 63 mg of solid are obtained (m.p.=100-102° C.). Yield=27%

$^1$H NMR (CDCl$_3$, 400 MHz): 0.86 (t, J=7.2 Hz, 3H); 1.25 (m, 4H); 1.42 (m, 2H); 2.75 (t, J=7.7 Hz, 2H); 3.04 (t, J=7.7 Hz, 2H); 3.18 (dt, J=4.3, 5.9 Hz, 2H); 3.32 (s, 3H); 4.42 (t, J=5.5 Hz, 1H); 7.22 (m, 1H); 7.33 (d, J=8.1 Hz, 2H); 7.47-7.54 (m, 5H).

Example 6

Synthesis of 3-[3'-(3-heptyl-1-methylureido)biphenyl-4-yl]-N-hydroxypropionamide

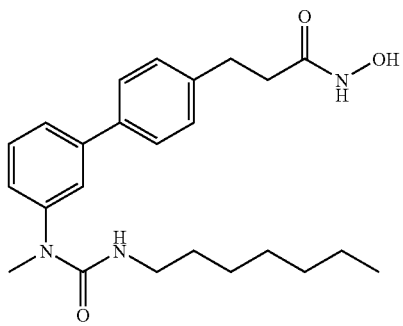

a. Preparation of methyl 3-[3'-(3-heptyl-1-methylureido)biphenyl-4-yl]propanoate 1.2 mL (7.43 mmol, 2 eq) of heptyl isocyanate are added to a solution of 1.0 g (3.7 mmol, 1 eq) of methyl 3-(3'-methylaminobiphenyl-4-yl)propanoate (obtained as in 4c) in 15 mL of a 4/1 tetrahydrofuran/triethylamine mixture. The reaction mixture is stirred for 12 hours at 40° C. The reaction is stopped by addition of 10 mL of water and then extracted with ethyl acetate. The organic phases are combined and dried over sodium sulfate. The solvents are evaporated off and the residue is then chromatographed on silica gel (70/30 heptane/ethyl acetate). 1.15 g of methyl 3-[3'-(1-methyl-3-heptylureido)biphenyl-4-yl]propanoate are obtained. Yield=76% b. Synthesis of 3-[3'-(3-heptyl-1-methylureido)biphenyl-4-yl]-N-hydroxypropionamide 320 mg (5.7 mmol, 11.4 eq) of potassium hydroxide dissolved in 1.7 ml of methanol are added to a solution of 251 mg (3.6 mmol, 7.2 eq) of hydroxylamine hydrochloride in 2.5 ml of methanol. The reaction mixture is stirred for one hour at room temperature (formation of a white precipitate).

The supernatant solution is taken up and added dropwise to a solution of 206 mg of methyl 3-[3'-(3-heptyl-1-methylureido)biphenyl-4-yl]propanoate in 2 ml of methanol. The reaction mixture is stirred for 24 hours at room temperature. The reaction medium is evaporated to dryness, taken up in water, neutralized to pH 6-7 with 1N acetic acid solution and extracted with ethyl acetate. The organic phases are combined, washed with water and dried over sodium sulfate. The solvent is evaporated off and the residue (242 mg) is chromatographed on silica gel (10 g CombiFlash column) eluted with 95/5 dichloromethane/methanol. 155 mg of the pinkish powder obtained are crystallized from ethyl acetate with the product obtained during a preceding synthesis performed under the same conditions.

142 mg of 3-[3'-(3-heptyl-1-methylureido)biphenyl-4-yl]-N-hydroxypropionamide in the form of white crystals are obtained (m.p.=100-101° C.). Yield=69%

¹H NMR (DMSO-d6, 400 MHz): 0.85 (t, 3H); 1.24 (m, 8H); 1.39 (m, 2H); 2.29 (t, 2H); 2.85 (t, 2H); 3.02 (q, 2H); 3.20 (s, 3H); 6.06 (t, 1H); 7.02 (d, 1H); 7.29 (d, 2H); 7.46 (m, 3H); 7.57 (d, 2H); 8.72 (s, 1H); 10.4 (s, 1H).

Example 7

Synthesis of 3-[3'-(1-methyl-3-naphthalen-2-ylureido)biphenyl-4-yl]propanoic acid

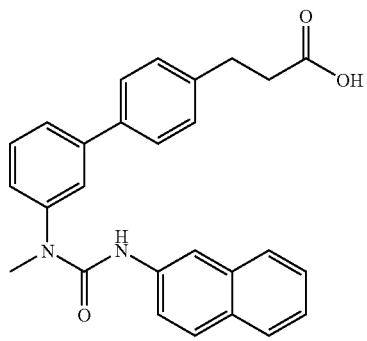

a. Preparation of methyl[3-(4,4,5,5-tetramethyl[1,3,2]dioxaborolan-2-yl)phenyl]amine 35 g (4 mol %) of diphenylphosphinoferrocene-palladium dichloride are added to a solution of 200 g (1.075 mol, 1 eq) of (3-bromophenyl)methylamine and 286.7 g (1.129 mol, 1.05 eq) of pinacol diborane in 2 L of dimethylformamide in the presence of 316.4 g (3.225 mol, 3 eq) of potassium acetate. The reaction medium is heated at 100° C. for 3 hours and then stirred at room temperature for 15 hours. The reaction medium is filtered through Celite and 2 L of ethyl acetate are then added to the filtrate. The organic medium is washed with water and then separated out by settling. The solvents are evaporated off and the black oil obtained is chromatographed on silica gel eluted with heptane/ethyl acetate (90/10). 183 g of methyl-[3-(4,4,5,5-tetramethyl[1,3,2]dioxaborolan-2-yl)phenyl]amine in the form of an orange-yellow oil are obtained. Yield=73% b. Preparation of ethyl (E)-3-(3'-methylaminobiphenyl-4-yl)acrylate

In a manner similar to that of Example (1f), by reaction of 2.2 g (8.6 mmol, 1 eq) of ethyl 4-bromocinnamate, 2.0 g (8.6 mmol, 1 eq) of methyl[3-(4,4,5,5-tetramethyl[1,3,2]dioxaborolan-2-yl)phenyl]amine and 500 mg of tetrakis(triphenylphosphine)palladium in 20 mL of a mixture of dimethylformamide and of 2M potassium phosphate solution (5/1), 1.7 g of ethyl (E)-3-(3'-methylaminobiphenyl-4-yl)acrylate are obtained in oil form. Yield=71% c. Preparation of ethyl 3-(3'-methylaminobiphenyl-4-yl)propanoate

A solution of 1.7 g (6.0 mmol) of ethyl (E)-3-(3'-methylaminobiphenyl-4-yl)acrylate in 25 ml of methanol is stirred for 12 hours at room temperature in the presence of 300 mg (18% by mass) of 10% palladium-on-charcoal under a hydrogen atmosphere. The palladium is filtered off and the solvent is evaporated off. 1.52 g of ethyl 3-(3'-methylaminobiphenyl-4-yl)propanoate are obtained. Yield=90% d. Preparation of ethyl 3-[3'-(1-methyl-3-naphthalen-2-ylureido)biphenyl-4-yl]propanoate 250 mg (1.43 mmol, 1.3 eq) of naphthyl isocyanate are added to a solution of 310 mg (1.1 mmol, 1 eq) of ethyl 3-(3'-methylaminobiphenyl-4-yl)propanoate in 3 mL of dichloromethane. The reaction mixture is heated at 45-50° C. for 20 hours. The reaction medium is evaporated to dryness and the residue is then crystallized from ethyl ether, filtered and dried. 452 mg of ethyl 3-[3'-(1-methyl-3-naphthalen-2-ylureido)biphenyl-4-yl]propanoate are obtained in the form of a white powder. Yield=91% e. Synthesis of 3-[3'-(1-methyl-3-naphthalen-2-ylureido)biphenyl-4-yl]propanoic acid 392 mg (9.8 mmol, 10 eq) of sodium hydroxide are added to a solution of 444 mg (0.98 mmol, 1 eq) of ethyl 3-[3'-(1-methyl-3-naphthalen-2-ylureido)biphenyl-4-yl]propanoate in 10 mL of ethanol. The reaction mixture is heated at 55° C. overnight. The reaction medium is evaporated to dryness, taken up in water, acidified with 1N hydrochloric acid solution and extracted with ethyl acetate. The organic phases are combined, washed with water and dried over sodium sulfate. The solvent is evaporated off and the residue is recrystallized from ethyl acetate, filtered and dried.

308 mg of 3-[3'-(1-methyl-3-naphthalen-2-ylureido)biphenyl-4-yl]propanoic acid in the form of an off-white powder are obtained (m.p.=170-171° C.). Yield=87%

¹H NMR (CDCl₃, 400 MHz): 2.61 (t, 2H); 2.97 (t, 2H); 3.39 (s, 3H); 6.55 (s, 1H); 7.29 (m, 5H); 7.31 (s, 1H); 7.51 (m, 5H); 7.67 (t, 3H); 7.91 (s, 1H).

Example 8

Synthesis of 3-[3'-(3-heptyl-1-methylthioureido)biphenyl-4-yl]propanoic acid

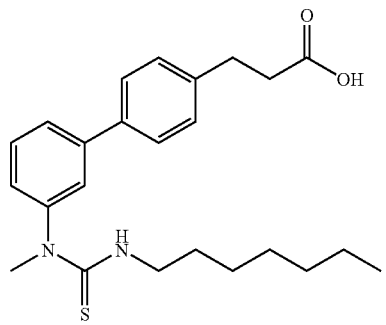

a. Preparation of ethyl 3-[3'-(3-heptyl-1-methylthioureido)biphenyl-4-yl]propanoate 525 µl (3.04 mmol, 3 eq) of heptyl isothiocyanate are added to 288 mg (1.02 mmol, 1 eq) of ethyl 3-(3'-methylaminobiphenyl-4-yl)propanoate (prepared in Example 7c). The reaction mixture is heated at 100° C. by microwave for 3 hours 30 minutes. The residue is chromatographed on silica gel (15 g FlashSmart Pack column) eluted with 90/10 heptane/ethyl acetate.

361 mg of ethyl 3-[3'-(3-heptyl-1-methylthioureido)biphenyl-4-yl]propanoate are obtained in the form of a yellowish oil. Yield=80% b. Synthesis of 3-[3'-(3-heptyl-1-methylthioureido)biphenyl-4-yl]propanoic acid 422 mg (10.5 mmol, 10 eq) of sodium hydroxide are added to a solution of 465 mg (1.05 mmol, 1 eq) of ethyl 3-[3'-(3-heptyl-1-methylthioureido)biphenyl-4-yl]propanoate in 10 mL of ethanol. The reaction mixture is heated at 50° C. for 2 hours. The reaction medium is evaporated to dryness, taken up in water, acidified with 2N hydrochloric acid solution and extracted with ethyl acetate. The organic phases are combined, washed with water and dried over sodium sulfate. The solvent is evaporated off and the paste obtained is crystallized from ethyl ether, filtered and dried.

398 mg of 3-[3'-(3-heptyl-1-methylthioureido)biphenyl-4-yl]propanoic acid in the form of off-white crystals are obtained (m.p.=95-96° C.). Yield=92%

$^1$H NMR (CDCl$_3$, 400 MHz): 0.85 (t, 3H); 1.24 (m, 8H); 1.48 (m, 2H); 2.75 (t, 2H); 3.04 (t, 2H); 3.57 (q, 2H); 3.72 (s, 3H); 5.42 (t, 1H); 7.20 (d, 1H); 7.34 (d, 2H); 7.46 (s, 1H); 7.56 (m, 3H); 7.62 (d, 1H).

Example 9

Synthesis of (E)-3-[2-fluoro-3'-(3-heptyl-1-methylureido)biphenyl-4-yl]acrylic acid

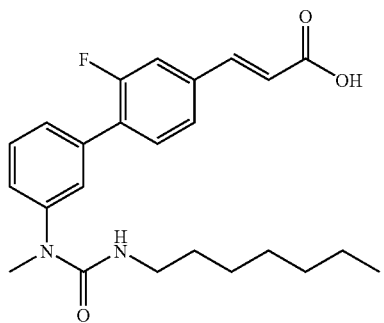

a. Preparation of methyl (E)-3-(3-fluoro-4-hydroxyphenyl)acrylate 13.1 g (0.039 mol, 2.2 eq) of methyl (triphenylphosphoranylidene)acetate are added to a solution of 2.5 g (0.0178 mol, 1 eq) of 3-fluoro-4-hydroxybenzaldehyde in 30 ml of toluene. The reaction mixture is heated at 80° C. for 2 hours. The reaction medium is hydrolyzed in water and extracted with ethyl acetate. The organic phases are combined, washed with water and dried over sodium sulfate. The solvent is evaporated off and the oil obtained is chromatographed on silica gel (70/30 heptane/ethyl acetate). 2.7 g of methyl (E)-3-(3-fluoro-4-hydroxyphenyl)acrylate are obtained in solid form. Yield=78% b. Preparation of methyl (E)-3-(3-fluoro-4-trifluoromethanesulfonyloxyphenyl)acrylate 1.40 mL (8.3 mmol, 1.1 eq) of triflic anhydride are added to a solution of 1.47 g (7.5 mmol, 1 eq) of methyl (E)-3-(3-fluoro-4-hydroxyphenyl)acrylate and 1.57 mL (9.0 mmol, 1.2 eq) of diisopropylethylamine in 10 mL of dichloromethane. The reaction mixture is stirred at room temperature overnight. The reaction medium is hydrolyzed in water, acidified with 1N hydrochloric acid solution and extracted with ethyl acetate. The organic phases are combined, washed with water and dried over sodium sulfate. The solvent is evaporated off and 2.51 g of methyl (E)-3-(3-fluoro-4-trifluoromethanesulfonyloxyphenyl)acrylate are obtained in the form of a brown oil. Yield=100% c. Preparation of methyl (E)-3-[2-fluoro-3'-(3-heptyl-1-methylureido)biphenyl-4-yl]acrylate 85 mg (0.38 mmol, 0.05 eq) of palladium acetate are added to a mixture of 2.50 g (7.6 mmol, 1 eq) of methyl (E)-3-(3-fluoro-4-trifluoromethanesulfonyloxyphenyl)acrylate, 3.71 g (9.9 mmol, 1.3 eq) of 3-heptyl-1-methyl-1-[3-(4,4,5,5-tetramethyl[1,3,2]dioxaborolan-2-yl)phenyl]urea (prepared as in Example 1e), 272 mg (0.78 mmol, 0.1 eq) of 2-(dicyclohexylphosphino)biphenyl and 5.5 mL of 2M potassium phosphate solution in 28 ml of dimethylformamide. The reaction mixture is heated at 90-95° C. overnight. The reaction medium is hydrolyzed in saturated ammonium chloride solution and extracted with ethyl acetate. The organic phases are combined, washed with water and dried over sodium sulfate. The solvent is evaporated off and the brown paste obtained (4.16 g) is chromatographed on silica gel (120 g CombiFlash column) eluted with 80/20 heptane/ethyl acetate. 706 mg (22%) of a "cis/trans" mixture are obtained. This solid is washed in an ethyl ether/heptane mixture, filtered and dried. 238 mg of methyl (E)-3-[2-fluoro-3'-(3-heptyl-1-methylureido)biphenyl-4-yl]acrylate in the form of a white solid are obtained. Yield=7% d. Synthesis of (E)-3-[2-fluoro-3'-(3-heptyl-1-methylureido)biphenyl-4-yl]acrylic acid 220 mg (5.5 mmol, 10 eq) of sodium hydroxide are added to a solution of 234 mg (0.55 mmol, 1 eq) of methyl 3-[2-fluoro-3'-(3-heptyl-1-methylureido)biphenyl-4-yl]acrylate in 6 mL of ethanol+2 ml of tetrahydrofuran. The reaction mixture is heated at 50° C. overnight. The reaction medium is evaporated to dryness, taken up in water, acidified with 1N hydrochloric acid solution and extracted with ethyl acetate. The organic phases are combined, washed with water and dried over sodium sulfate. The solvent is evaporated off and the yellowish paste obtained (240 mg) is chromatographed on silica gel (15 g FlashSmart Pack column) eluted with 96/4 dichloromethane/methanol, and the solid obtained is then taken up in heptane and then in ethyl ether, filtered and dried.

105 mg of (E)-3-[2-fluoro-3'-(3-heptyl-1-methylureido)biphenyl-4-yl]acrylic acid are obtained in the form of white crystals (m.p.=130-131° C.). Yield=79%

$^1$H NMR (CDCl$_3$, 400 MHz): 0.85 (t, 3H); 1.21 (m, 8H); 1.42 (m, 2H); 3.19 (q, 2H); 3.32 (s, 3H); 4.45 (t, 1H); 6.52 (d, J=16 Hz, 1H); 7.29 (d, 1H); 7.38 (d, 1H); 7.50 (m, 4H); 7.76 (d, J=16 Hz, 1H).

Example 10

Synthesis of 3-[2-fluoro-3'-(3-heptyl-1-methylureido)biphenyl-4-yl]propanoic acid

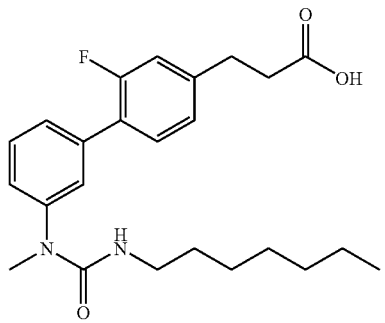

a. Preparation of ethyl 3-[2-fluoro-3'-(3-heptyl-1-methylureido)biphenyl-4-yl]propanoate 37 mg (10% by mass) of 10% palladium-on-charcoal are added to a solution of 365 mg (0.85 mmol, 1 eq) of methyl (E)-3-[2-fluoro-3'-(3-heptyl-1-methylureido)biphenyl-4-yl]acrylate (prepared in Example 9c) in 7 ml of methanol. The reaction mixture, under a pressure of 7 bar of hydrogen, is heated at 40° C. overnight. The reaction medium is filtered through Celite and then evaporated to dryness. The oil obtained (328 mg) is chromatographed on silica gel (15 g FlashSmart Pack column) eluted with 70/30 heptane/ethyl acetate.

246 mg of ethyl 3-[2-fluoro-3'-(3-heptyl-1-methylureido)biphenyl-4-yl]propanoate are obtained in the form of a yellow oil. Yield=68% b. Synthesis of 3-[2-fluoro-3'-(3-heptyl-1-methylureido)biphenyl-4-yl]propanoic acid 227 mg (5.7 mmol, 10 eq) of sodium hydroxide are added to a solution of 243 mg (0.56 mmol, 1 eq) of ethyl 3-[2-fluoro-3'-(3-heptyl-1-methylureido)biphenyl-4-yl]propanoate in 6 ml of methanol. The reaction mixture is heated at 50° C. for 4 hours 30 minutes. The reaction medium is evaporated to dryness, taken up in water, acidified with 2N hydrochloric acid solution and extracted with ethyl acetate. The organic phases are combined, washed with water and dried over sodium sulfate. The solvent is evaporated off and the paste obtained (258 mg) is crystallized from ethyl ether, filtered and dried.

150 mg of 3-[2-fluoro-3'-(3-heptyl-1-methylureido)biphenyl-4-yl]propanoic acid are obtained in the form of a white powder (m.p.=80-82° C.). Yield=64%

$^1$H NMR (CDCl$_3$, 400 MHz): 0.87 (t, 3H); 1.27 (m, 8H); 1.43 (m, 2H); 2.75 (t, 2H); 3.03 (t, 2H); 3.19 (q, 2H); 3.32 (s, 3H); 4.47 (t, 1H); 7.06 (d, 1H); 7.11 (d, 2H); 7.25 (d, 1H); 7.37 (t, 1H); 7.47 (m, 3H).

Example 11

Synthesis of 3-[3'-(3-hexyl-1-methylureido)biphenyl-4-yl]propanoic acid

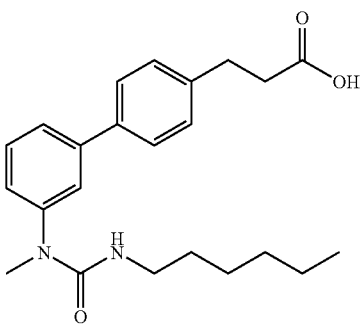

a. Preparation of ethyl 3-[3'-(3-hexyl-1-methylureido)biphenyl-4-yl]propanoate 380 μl (2.55 mmol, 1.5 eq) of hexyl isocyanate are added to 482 mg (1.7 mmol, 1 eq) of ethyl 3-(3'-methylaminobiphenyl-4-yl)propanoate (Example 7c). The reaction mixture is heated at 100° C. by microwave for 30 minutes. The residue is chromatographed on silica gel (50 g FlashSmart Pack column) eluted with 70/30 heptane/ethyl acetate.

470 mg of ethyl 3-[3'-(3-hexyl-1-methylureido)biphenyl-4-yl]propanoate are obtained in the form of a yellow oil. Yield=67% b. Synthesis of 3-[3'-(3-hexyl-1-methylureido)biphenyl-4-yl]propanoic acid 452 mg (11.3 mmol, 10 eq) of sodium hydroxide are added to a solution of 464 mg (1.13 mmol, 1 eq) of ethyl 3-[3'-(3-hexyl-1-methylureido)biphenyl-4-yl]propanoate in 10 mL of ethanol. The reaction mixture is heated at 50° C. for 6 hours. The reaction medium is evaporated to dryness, taken up in water, acidified with 1N hydrochloric acid solution and extracted with ethyl acetate. The organic phases are combined, washed with water and dried over sodium sulfate. The solvent is evaporated off and the orange oil that crystallizes is taken up in ethyl ether, filtered and dried.

357 mg of 3-[3'-(3-hexyl-1-methylureido)biphenyl-4-yl]propanoic acid are obtained in the form of a cream-colored powder (m.p.=119-120° C.). Yield=83%

$^1$H NMR (CDCl$_3$, 400 MHz): 0.85 (t, 3H); 1.24 (m, 6H); 1.42 (m, 2H); 2.75 (t, 2H); 3.04 (t, 2H); 3.18 (q, 2H); 3.32 (s, 3H); 4.43 (t, 1H); 7.22 (d, 1H); 7.33 (d, 2H); 7.50 (m, 5H).

Example 12

Synthesis of 3-[3'-(3-octyl-1-methylureido)biphenyl-4-yl]propanoic acid

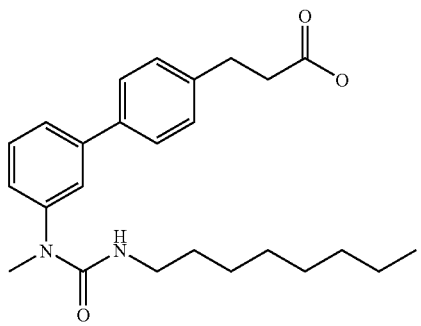

a. Preparation of ethyl 3-[3'-(3-octyl-1-methylureido)biphenyl-4-yl]propanoate 464 μl (2.55 mmol, 1.5 eq) of octyl isocyanate are added to 482 mg (1.7 mmol, 1 eq) of ethyl 3-(3'-methylaminobiphenyl-4-yl)propanoate (prepared in Example 7c). The reaction mixture is heated at 100° C. by microwave for 30 minutes. The residue is chromatographed on silica gel (50 g FlashSmart Pack column) eluted with 70/30 heptane/ethyl acetate. 755 mg of ethyl 3-[3'-(3-octyl-1-methylureido)biphenyl-4-yl]propanoate are obtained in the form of a yellowish oil. Yield=100% b. Synthesis of 3-[3'-(3-octyl-1-methylureido)biphenyl-4-yl]propanoic acid 684 mg (17.1 mmol, 10 eq) of sodium hydroxide are added to a solution of 750 mg (1.71 mmol, 1 eq) of ethyl 3-[3'-(3-octyl-1-methylureido)biphenyl-4-yl]propanoate in 15 mL of ethanol. The reaction mixture is heated at 50° C. for 6 hours. The reaction medium is evaporated to dryness, taken up in water, acidified with 1N hydrochloric acid solution and extracted with ethyl acetate. The organic phases are combined, washed with water and dried over sodium sulfate. The solvent is evaporated off and the orange oil obtained is chromatographed on silica gel (30 g FlashSmart Pack column) eluted with 30/70 heptane/ethyl acetate and then crystallized from ethyl ether, filtered and dried. 500 mg of 3-[3'-(3-octyl-1-methylureido)biphenyl-4-yl]propanoic acid are obtained in the form of a white powder (m.p.=86-88° C.). Yield=71%

$^1$H NMR (CDCl$_3$, 400 MHz): 0.87 (t, 3H); 1.24 (m, 10H); 1.42 (m, 2H); 2.75 (t, 2H); 3.04 (t, 2H); 3.18 (q, 2H); 3.32 (s, 3H); 4.43 (t, 1H); 7.22 (d, 1H); 7.33 (d, 2H); 7.47-7.54 (m, 5H).

Example 13

Synthesis of 3-{3'-[3-(4-benzyloxyphenyl)-1-methylureido]biphenyl-4-yl}propanoic acid

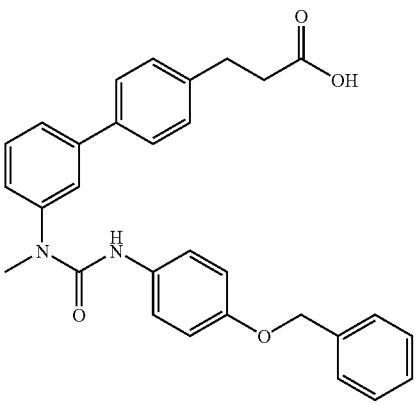

a. Preparation of ethyl 3-{3'-[3-(4-benzyloxyphenyl)-1-methylureido]biphenyl-4-yl}propanoate 345 mg (1.5 mmol, 1.5 eq) of 1-benzyloxy-4-isocyanatobenzene are added to 283 mg (1.0 mmol, 1 eq) of ethyl 3-(3'-methylaminobiphenyl-4-yl)propanoate (prepared in Example 7c). The reaction mixture is heated at 100° C. by microwave for 30 minutes. The residue is taken up in a heptane/ethyl ether mixture, filtered and dried.

522 mg of ethyl 3-{3'-[3-(4-benzyloxyphenyl)-1-methylureido]biphenyl-4-yl}propanoate are obtained in the form of a cream-colored powder. Yield=100% b. Synthesis of 3-{3'-[3-(4-benzyloxyphenyl)-1-methylureido]biphenyl-4-yl}propanoic acid 400 mg (10 mmol, 10 eq) of sodium hydroxide are added to a solution of 515 mg (1.0 mmol, 1 eq) of ethyl 3-{3'-[3-(4-benzyloxyphenyl)-1-methylureido]biphenyl-4-yl}propanoate in 20 mL of ethanol. The reaction mixture is heated at 50° C. for 5 hours. The reaction medium is evaporated to dryness, taken up in water, acidified with 1N hydrochloric acid solution and extracted with ethyl acetate. The organic phases are combined, washed with water and dried over sodium sulfate. The solvent is evaporated off and the solid obtained is taken up in ethyl ether and then in ethyl acetate, filtered and dried.

441 mg of 3-{3'-[3-(4-benzyloxyphenyl)-1-methylureido]biphenyl-4-yl}propanoic acid are obtained in the form of a light-beige powder (m.p.=173.5-175° C.). Yield=92%

$^1$H NMR (CDCl$_3$, 400 MHz): 2.64 (t, 2H); 3.00 (t, 2H); 3.37 (s, 3H); 5.00 (s, 2H); 6.29 (s, 1H); 6.85 (d, 2H); 7.20 (d, 2H); 7.30-7.40 (m, 8H); 7.50-7.56 (m, 5H).

Example 14

Synthesis of 3-{3'-[3-(4-butylphenyl)-1-methylureido]biphenyl-4-yl}propanoic acid

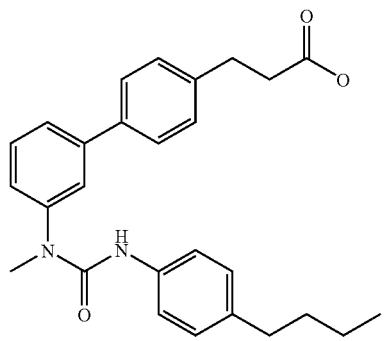

a. Preparation of ethyl 3-{3'-[3-(4-butylphenyl)-1-methylureido]biphenyl-4-yl}propanoate 345 mg (1.5 mmol, 1.5 eq) of 1-butyl-4-isocyanatobenzene are added to 283 mg (1.0 mmol, 1 eq) of ethyl 3-(3'-methylaminobiphenyl-4-yl)propanoate (prepared in Example 7c). The reaction mixture is heated at 100° C. by microwave for 30 minutes. The mixture is chromatographed on silica gel (15 g FlashSmart column) eluted with 80/20 heptane/ethyl acetate. 442 mg of ethyl 3-{3'-[3-(4-butylphenyl)-1-methylureido]biphenyl-4-yl}propanoate are obtained in the form of a yellow oil that crystallizes. Yield=96% b. Synthesis of 3-{3'-[3-(4-butylphenyl)-1-methylureido]biphenyl-4-yl}propanoic acid 380 mg (10 mmol, 10 eq) of sodium hydroxide are added to a solution of 436 mg (1.0 mmol, 1 eq) of ethyl 3-{3'-[3-(4-butylphenyl)-1-methylureido]biphenyl-4-yl}propanoate in 20 mL of ethanol. The reaction mixture is heated at 50° C. for 3 hours. The reaction medium is evaporated to dryness, taken up in water, acidified with 1N hydrochloric acid solution and extracted with ethyl acetate. The organic phases are combined, washed with water and dried over sodium sulfate. The solvent is evaporated off and 352 mg of 3-{3'-[3-(4-butylphenyl)-1-methylureido]biphenyl-4-yl}propanoic acid are obtained in the form of white crystals (m.p.=157-158° C.). Yield=86%

$^1$H NMR (CDCl$_3$, 400 MHz): 0.88 (t, 3H); 1.30 (m, 2H); 1.52 (m, 2H); 2.52 (t, 2H); 2.72 (t, 2H); 3.01 (t, 2H); 3.38 (s, 3H); 6.26 (s, 1H); 7.04 (d, 2H); 7.18 (d, 2H); 7.30 (m, 3H); 7.54 (m, 5H).

Example 15

Synthesis of 3-[3'-(3-heptyl-1-methylureido)-2-(2-methoxyethoxy)biphenyl-4-yl]propanoic acid

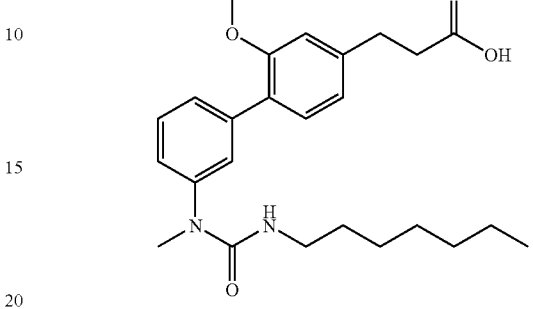

a. Preparation of methyl 3-benzyloxy-4-iodobenzoate 2.35 mL (19.78 mmol, 1.1 eq) of benzyl bromide are added to a solution of 5.0 g (17.98 mmol, 1 eq) of methyl 3-hydroxy-4-iodobenzoate in 30 ml of methyl ethyl ketone in the presence of 5.0 g (36.18 mmol, 2 eq) of potassium carbonate. The reaction mixture is heated at 60° C. for 5 hours and then hydrolyzed in water and extracted with ethyl acetate. 6.9 g of methyl 3-benzyloxy-4-iodobenzoate are obtained in oil form and are used in the following reaction without further purification.

b. Preparation of (3-benzyloxy-4-iodophenyl)methanol 1.18 g (54 mmol, 3 eq) of lithium borohydride are added to a solution of 6.9 g crude (17.98 mmol, 1 eq) of methyl 3-benzyloxy-4-iodobenzoate in 30 ml of THF. The reaction mixture is heated at 60° C. for 12 hours and then hydrolyzed in saturated ammonium chloride solution NH4Cl and extracted with ethyl acetate. 6.5 g of (3-benzyloxy-4-iodophenyl)methanol are obtained in oil form and are used in the following reaction without further purification.

c. Preparation of 3-benzyloxy-4-iodobenzaldehyde 7.8 g (90 mmol, 5 eq) of manganese oxide are added to a solution of 6.5 g (17.98 mmol, 1 eq) of (3-benzyloxy-4-iodophenyl)methanol in 50 mL of dichloromethane. The reaction medium is stirred for 12 hours at room temperature, and the solid is then filtered off and the solvent is evaporated off. The residual oil is chromatographed on silica gel (8/2 heptane/ethyl acetate). The oil obtained is crystallized from pentane. 3.25 g of 3-benzyloxy-4-iodobenzaldehyde are obtained. Yield=54% for the three steps c, d and e.

d. Preparation of methyl (E)-3-(3-benzyloxy-4-iodophenyl)acrylate 5.0 g (14.95 mmol, 1.5 eq) of methyl (triphenylphosphoranylidene)acetate are added to a solution of 3.25 g (9.6 mmol, 1 eq) of 3-benzyloxy-4-iodobenzaldehyde in 15 ml of toluene. The reaction mixture is heated at 90° C. for 1 hour. The solvent is evaporated off and the oil obtained is chromatographed on silica gel (8/2 heptane/ethyl acetate). After recrystallization from dichloromethane/heptane, 2.59 g of methyl (E)-3-(3-benzyloxy-4-iodophenyl)acrylate are obtained. Yield=68% e. Preparation of methyl (E)-3-[3'-(3-heptyl-1-methylureido)-2-hydroxybiphenyl-4-yl]acrylate A solution of 4.6 g (11.67 mmol, 1 eq) of methyl (E)-3-(3-benzyloxy-4-iodophenyl)acrylate, 4.8 g (12.83 mmol, 1.1 eq) of 3-heptyl-1-methyl-1-[3-(4,4,5,5-tetramethyl[1,3,2]dioxaborolan-2-yl)phenyl]urea (prepared as in Example 1e) in 18 ml of dimethylformamide+3 mL of 2M potassium phosphate solution, in the presence of 128 mg (5 mol %) of palladium acetate and 408 mg (10 mol %) of 2-(dicyclohexylphosphino) biphenyl is stirred at 80° C. for 5 hours. The reaction medium is hydrolyzed in water and then extracted with ethyl acetate. The organic phases are washed with saturated sodium chloride solution and dried over sodium sulfate. The solvents are evaporated off and the oil obtained is chromatographed on silica (7/3 heptane/ethyl acetate). 5.89 g of methyl (E)-3-[3'-(3-heptyl-1-methylureido)-2-hydroxybiphenyl-4-yl]acrylate are obtained in oil form. Yield=98% f. Preparation of methyl 3-[3'-(3-heptyl-1-methylureido)-2-hydroxybiphenyl-4-yl]propanoate A solution of 5.89 g (13.87 mmol, 1 eq) of methyl (E)-3-[3'-(3-heptyl-1-methylureido)-2-hydroxybiphenyl-4-yl]acrylate in 10 ml of methanol and 10 mL of ethyl acetate in the presence of 3 mL of acetic acid and 1.0 g (17% by mass) of 10% palladium-on-charcoal is stirred for 12 hours at room temperature under a hydrogen atmosphere. The palladium is filtered off through Celite and the solvents are evaporated off. The residue is chromatographed on silica gel (7/3 heptane/ethyl acetate) and crystallized from pentane. 3.0 g of methyl 3-[3'-(3-heptyl-1-methylureido)-2-hydroxybiphenyl-4-yl]propanoate are obtained in solid form. Yield=60% g. Preparation of methyl 3-[3'-(3-heptyl-1-methylureido)-2-(2-methoxyethoxy)biphenyl-4-yl]propanoate A solution of 200 mg (0.47 mmol, 1 eq) of methyl 3-[3'-(3-heptyl-1-methylureido)-2-hydroxybiphenyl-4-yl]propanoate, 200 mg (1.36 mmol, 3 eq) of 2-bromoethylmethyl ether and 390 mg (2.82 mmol, 6 eq) of potassium carbonate in the presence of 28 mg (0.188 mmol, 0.4 eq) of sodium iodide in 8 ml of methyl ethyl ketone is refluxed for 15 hours. The insoluble matter is filtered off and the solvent is evaporated off. The oil obtained is chromatographed on silica gel (10 g FlashSmart column) eluted with 40/60 heptane/ethyl acetate. 223 mg of methyl 3-[3'-(3-heptyl-1-methylureido)-2-(2-methoxyethoxy)biphenyl-4-yl]propanoate are obtained in the form of a yellowish oil. Yield=98% h. Synthesis of 3-[3'-(3-heptyl-1-methylureido)-2-(2-methoxyethoxy)biphenyl-4-yl]propanoic acid 278 mg (6.95 mmol, 10 eq) of sodium hydroxide are added to a solution of 337 mg (0.695 mmol, 1 eq) of methyl 3-[3'-(3-heptyl-1-methylureido)-2-(2-methoxyethoxy)biphenyl-4-yl]propanoate in 10 ml of methanol. The reaction mixture is heated at 50° C. for 2 hours. The reaction medium is evaporated to dryness, taken up in water, acidified with 2N hydrochloric acid solution and extracted with ethyl acetate. The organic phases are combined, washed with water and dried over magnesium sulfate. The solvent is evaporated off and the oil obtained is chromatographed on silica gel (10 g FlashSmart column) eluted with ethyl acetate. 274 mg of 3-[3'-(3-heptyl-1-methylureido)-2-(2-methoxyethoxy)biphenyl-4-yl] propanoic acid are obtained in the form of a whitish oil. Yield=84%

$^1$H NMR (CDCl$_3$, 400 MHz): 0.84 (t, 3H); 1.22-1.26 (m, 8H); 1.40 (m, 2H); 2.72 (t, 2H); 2.99 (t, 2H); 3.16 (q, 2H); 3.29 (s, 3H); 3.33 (s, 3H); 3.66 (m, 2H); 4.13 (m, 2H); 4.5 (t, 1H); 6.86 (s, 1H); 6.90 (d, 1H); 7.17 (d, 1H); 7.26 (d, 1H); 7.43 (t, 3H); 7.50 (d, 1H); 7.52 (s, 1H).

Example 16

Synthesis of 3-[3'-(3-heptyl-1-methylureido)-2-(3-methylbutoxy)biphenyl-4-yl]propanoic acid

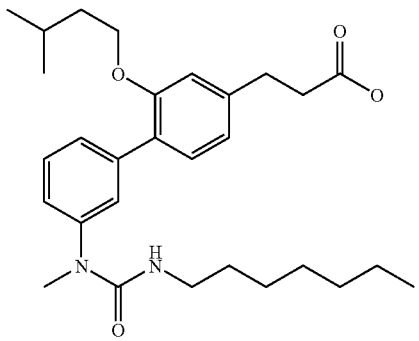

a. Preparation of methyl 3-[3'-(3-heptyl-1-methylureido)-2-(3-methylbutoxy)biphenyl-4-yl]propanoate A solution of 300 mg (0.703 mmol, 1 eq) of methyl 3-[3'-(3-heptyl-1-methylureido)-2-hydroxybiphenyl-4-yl]propanoate (prepared in Example 15f), 319 mg (2.11 mmol, 3 eq) of 1-bromo-3-methylbutane and 583 mg (4.22 mmol, 6 eq) of potassium carbonate in the presence of 42 mg (0.281 mmol, 0.4 eq) of sodium iodide in 10 ml of methyl ethyl ketone is refluxed for 21 hours. The insoluble matter is filtered off and the solvent is evaporated off. 400 mg of methyl 3-[3'-(3-heptyl-1-methylureido)-2-(3-methylbutoxy)biphenyl-4-yl] propanoate are obtained in the form of a yellowish oil. Quantitative yield.

b. Synthesis of 3-[3'-(3-heptyl-1-methylureido)-2-(3-methylbutoxy)biphenyl-4-yl]propanoic acid 281 mg (7.03 mmol, 10 eq) of sodium hydroxide are added to a solution of 400 mg (0.703 mmol, 1 eq) of methyl 3-[3'-(3-heptyl-1-methylureido)-2-(3-methylbutoxy)biphenyl-4-yl]propanoate in 10 ml of methanol. The reaction mixture is heated at 55° C. for 1 hour. The reaction medium is evaporated to dryness, taken up in water, acidified with 2N hydrochloric acid solution and extracted with ethyl acetate. The organic phases are combined, washed with water and dried over magnesium sulfate. The solvent is evaporated off and the oil obtained is chromatographed on silica gel (10 g FlashSmart column) eluted with 30/70 heptane/ethyl acetate. The product is crystallized from heptane and 284 mg of 3-[3'-(3-heptyl-1-methylureido)-2-(3-methylbutoxy)biphenyl-4-yl] propanoic acid are obtained in the form of white crystals (m.p.=60-62° C.). Yield=84%

¹H NMR (CDCl₃, 400 MHz): 0.84 (t, 3H); 0.86 (s, 3H); 0.89 (s, 3H); 1.21-1.27 (m, 8H); 1.39 (m, 2H); 1.60 (q, 2H); 1.70-1.75 (m, 1H); 2.73 (t, 2H); 3.00 (t, 2H); 3.16 (q, 2H); 3.29 (s, 3H); 3.99 (t, 2H); 4.41 (t, 1H); 6.85 (s, 1H); 6.89 (d, 1H); 7.17 (d, 1H); 7.24 (d, 1H); 7.40-7.45 (m, 3H).

Example 17

Synthesis of 3-[2-(3-chloropropoxy)-3'-(3-heptyl-1-methylureido)biphenyl-4-yl]propanoic acid

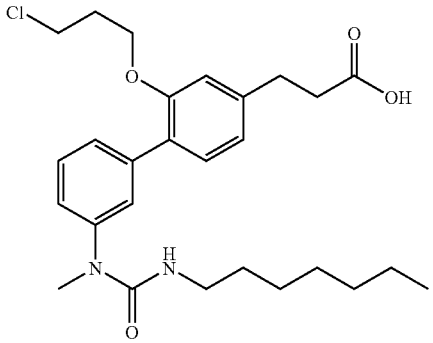

a. Preparation of methyl 3-[2-(3-chloropropoxy)-3'-(3-heptyl-1-methylureido)biphenyl-4-yl]propanoate A solution of 300 mg (0.703 mmol, 1 eq) of methyl 3-[3'-(3-heptyl-1-methylureido)-2-hydroxybiphenyl-4-yl]propanoate (prepared in Example 15f), 319 mg (2.11 mmol, 3 eq) of 1-chloro-3-iodopropane and 583 mg (4.22 mmol, 6 eq) of potassium carbonate in 10 ml of methyl ethyl ketone is refluxed for 7 hours. The insoluble matter is filtered off, the solvent is evaporated off and the oil obtained is chromatographed on silica gel (35 g FlashSmart column) eluted with 60/40 heptane/ethyl acetate. 394 mg of methyl 3-[2-(3-chloropropoxy)-3'-(3-heptyl-1-methylureido)biphenyl-4-yl]propanoate are obtained in the form of a yellowish oil. Quantitative yield.

b. Synthesis of 3-[2-(3-chloropropoxy)-3'-(3-heptyl-1-methylureido)biphenyl-4-yl]propanoic acid 31 mg (0.773 mmol, 1 eq) of sodium hydroxide are added to a solution of 389 mg (0.773 mmol, 1 eq) of methyl 3-[2-(3-chloropropoxy)-3'-(3-heptyl-1-methylureido)biphenyl-4-yl]propanoate in 10 ml of methanol. The reaction mixture is stirred at room temperature for 18 hours. The reaction medium is evaporated to dryness, taken up in water, acidified with 2N hydrochloric acid solution and extracted with ethyl acetate. The organic phases are combined, washed with water and dried over magnesium sulfate. The solvent is evaporated off and the oil obtained is chromatographed on silica gel (10 g FlashSmart column) eluted with 98/2 dichloromethane/methanol. The product is crystallized from heptane, the filtrate is evaporated and 21 mg of 3-[2-(3-chloropropoxy)-3'-(3-heptyl-1-methylureido)biphenyl-4-yl]propanoic acid are obtained in the form of a whitish oil. Yield=6%

¹H NMR (CDCl₃, 400 MHz): 0.84 (t, 3H); 1.22-1.27 (m, 8H); 1.40 (m, 2H); 1.98 (m, 2H); 2.73 (t, 2H); 3.00 (t, 2H); 3.15 (q, 2H); 3.29 (s, 3H); 3.45 (t, 2H); 4.07 (t, 2H); 4.43 (t, 1H); 6.87 (s, 1H); 6.89 (d, 1H); 7.17 (d, 1H); 7.24 (d, 1H); 7.40-7.46 (m, 3H).

Example 18

Synthesis of 3-[3'-(3-heptyl-1-methylureido)-2-methoxybiphenyl-4-yl]propanoic acid

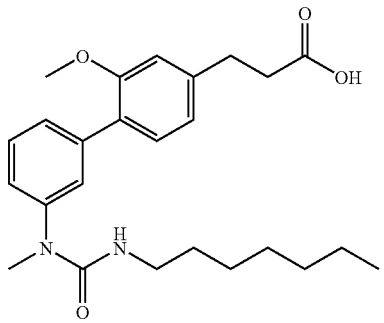

a. Preparation of 3-(methylamino)phenylboronic acid 166 mL (0.242 mol, 1.2 eq) of 1.6 M methyllithium in diethyl ether are added to a solution cooled to −70° C. of 37.6 g (0.202 mol, 1 eq) of 3-bromo-N-methylaniline (prepared in Example 7c) in 300 ml of tetrahydrofuran. The reaction medium is stirred at −70° C. for one hour and 306 mL (0.444 mol, 2.2 eq) of 1.5 M tert-butyllithium in diethyl ether are then added. The reaction medium is stirred at −70° C. for 45 minutes and 103.5 mL (0.808 mol, 4 eq) of trimethyl borate are then added. The reaction medium is stirred at room temperature for one hour and then hydrolyzed by addition of ice, acidified with 1 L of 2N hydrochloric acid and extracted with ethyl acetate. The organic phases are combined, washed with water and dried over magnesium sulfate. The solvent is evaporated off and 4.2 g (14%) of 3-(methylamino)phenylboronic acid are obtained. The aqueous phase is basified and extracted with ethyl acetate. The organic phases are combined, washed with water and dried over magnesium sulfate. The solvent is evaporated off and the residue is chromatographed on silica gel (8/2 heptane/ethyl acetate). 3.4 g (11%) of 3-(methylamino)phenylboronic acid are obtained.

b. Preparation of methyl (E)-3-(4-hydroxy-3-methoxyphenyl)acrylate 6.5 g (19.5 mmol, 3 eq) of methyl triphenylphosphoranylideneacetate are added to a solution of 1.0 g (6.5 mmol, 1 eq) of vanillin in 15 ml of toluene. The reaction mixture is stirred for 1 hour at 90° C. The solvent is evaporated off and the residual oil is then chromatographed on silica gel (8/2 heptane/ethyl acetate). 1.12 g of methyl (E)-3-(4-hydroxy-3-methoxyphenyl)acrylate are obtained in oil form. Yield=83% c. Preparation of methyl (E)-3-(3-methoxy-4-trifluoromethoxyphenyl)acrylate 0.472 mL (2.88 mmol, 1.2 eq) of triflic anhydride are added to a solution at 0° C. of 500 mg (2.40 mmol, 1 eq) of methyl (E)-3-(4-hydroxy-3-methoxyphenyl)acrylate in 10 mL of dichloromethane in the presence of 1 ml of triethylamine. The reaction mixture is stirred for 1 hour at 0° C. The reaction medium is hydrolyzed in sodium hydrogen carbonate solution and then extracted with ethyl acetate. The organic phases are washed with saturated sodium chloride solution and dried over sodium sulfate. The solvent is evaporated off and the methyl (E)-3-(3-methoxy-4-trifluoromethoxyphenyl)acrylate obtained in oil form is used in the next step without further purification.

d. Preparation of methyl (E)-3-(2-methoxy-3'-methylaminobiphenyl-4-yl)acrylate 27 mg (5 mol %) of palladium acetate and 84 mg (10 mol %) of dicyclohexylbiphenylphosphine are added to a solution of methyl (E)-3-(3-methoxy-4-trifluoromethoxyphenyl)acrylate (2.40 mmol, 1 eq) obtained in the preceding step, 435 mg (2.88 mmol, 1.2 eq) of 3-(methylamino)phenylboronic acid (prepared in step 18a) in 4 ml of dimethylformamide+1 ml of 2M potassium phosphate solution. The mixture is heated at 90° C. for 3 hours. The reaction medium is hydrolyzed in water and then extracted with ethyl acetate. The organic phases are washed with saturated sodium chloride solution and dried over sodium sulfate. The solvent is evaporated off and the residual oil is then chromatographed on silica gel (7/3 heptane/ethyl acetate). 560 mg of methyl (E)-3-(2-methoxy-3'-methylaminobiphenyl-4-yl)acrylate are obtained in oil form. Yield=78% e. Preparation of methyl 3-(2-methoxy-3'-methylaminobiphenyl-4-yl)propanoate 100 mg (18% by mass) of 10% palladium-on-charcoal are added to a solution of 560 mg (1.88 mmol, 1 eq) of methyl (E)-3-(2-methoxy-3'-methylaminobiphenyl-4-yl)acrylate in 10 ml of methanol. The reaction mixture is stirred at room temperature under a hydrogen atmosphere for 4 hours. The reaction medium is filtered through Celite and then evaporated to dryness. 495 mg of methyl 3-(2-methoxy-3'-methylaminobiphenyl-4-yl)propanoate are obtained in oil form. Yield=88% f. Preparation of methyl 3-[3'-(3-heptyl-1-methylureido)-2-methoxybiphenyl-4-yl]propanoate 540 μL (3.3 mmol, 2 eq) of heptyl isocyanate are added to a solution of 495 mg (1.65 mmol, 1 eq) of methyl 3-(2-methoxy-3'-methylaminobiphenyl-4-yl)propanoate in 10 mL of an 8/2 tetrahydrofuran/triethylamine mixture. The reaction mixture is stirred for 12 hours at room temperature. The reaction medium is hydrolyzed in water and then extracted with ethyl acetate. The organic phases are combined and dried over sodium sulfate. The solvents are evaporated off and the residue is then chromatographed on silica gel (70/30 heptane/ethyl acetate). 525 mg of methyl 3-[3'-(3-heptyl-1-methylureido)-2-methoxybiphenyl-4-yl]propanoate are obtained in oil form. Yield=72% g. Synthesis of 3-[3'-(3-heptyl-1-methylureido)-2-methoxybiphenyl-4-yl]propanoic acid 200 mg (5.0 mmol, 4.2 eq) of sodium hydroxide are added to a solution of 525 mg (1.19 mmol, 1 eq) of methyl 3-[3'-(3-heptyl-1-methylureido)-2-methoxybiphenyl-4-yl]propanoate in 6 ml of a tetrahydrofuran/methanol mixture (8/2). The reaction mixture is stirred at room temperature for 3 hours. The reaction medium is hydrolyzed with water, acidified with acetic acid solution and extracted with ethyl acetate. The organic phases are combined, washed with sodium chloride solution and dried over sodium sulfate. The solvent is evaporated off and the residual oil is chromatographed on silica (7/3 to 1/1 heptane/ethyl acetate). The product is crystallized from pentane and 216 mg of 3-[3'-(3-heptyl-1-methylureido)-2-methoxybiphenyl-4-yl]propanoic acid are obtained in the form of a white powder (m.p.=100-101° C.). Yield=42%

$^1$H NMR (CDCl$_3$, 400 MHz): 0.87 (t, 3H); 1.25 (m, 8H); 1.44 (m, 2H); 2.76 (t, 2H); 3.04 (t, 2H); 3.18 (q, 2H); 3.32 (s, 3H); 3.84 (s, 3H); 4.53 (t, 1H); 6.88 (s, 1H); 6.92 (d, 1H); 7.19 (m, 1H); 7.25 (d, 1H); 7.43-7.46 (m, 3H).

Example 19

Synthesis of 3-[3'-(3-heptyl-1-methylureido)-2-methylbiphenyl-4-yl]propanoic acid

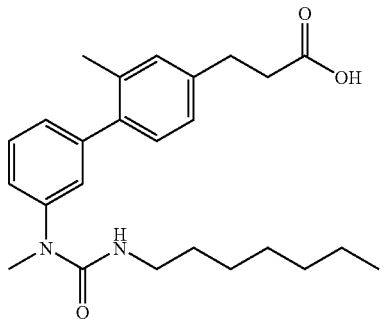

a. Preparation of (4-bromo-3-methylphenyl)methanol 284 mg (12.9 mmol, 3 eq) of lithium borohydride are added to a solution of 1.0 g (4.3 mmol, 1 eq) of methyl 3-methyl-4-bromobenzoate in 10 ml of tetrahydrofuran. The reaction mixture is stirred at 60° C. for 12 hours. The reaction medium is hydrolyzed with ammonium chloride solution and extracted with ethyl acetate. The organic phases are combined, washed with sodium chloride solution and dried over sodium sulfate. 900 mg of (4-bromo-3-methylphenyl)methanol are obtained in oil form and used in the following reaction without further purification.

b. Preparation of 4-bromo-3-methylbenzaldehyde 3.7 g (43 mmol, 10 eq) of manganese dioxide are added to a solution of 900 mg (4.3 mmol, 1 eq) of (4-bromo-3-methylphenyl)methanol in 8 mL of dichloromethane. The reaction mixture is stirred for 12 hours at room temperature. The solid is filtered off and the solvent is evaporated off. 900 mg of 4-bromo-3-methylbenzaldehyde are obtained in oil form and used in the following reaction without further purification.

c. Preparation of methyl (E)-3-(4-bromo-3-methyl phenyl)acrylate 2.1 g (6.45 mmol, 1.5 eq) of methyl triphenylphosphoranylideneacetate are added to a solution of 900 mg of 4-bromo-3-methylbenzaldehyde in 5 ml of toluene. The reaction mixture is heated at 90° C. for 1 hour. The solvent is evaporated off and the residual oil is chromatographed on silica gel (8/2 heptane/ethyl acetate). 610 mg of methyl (E)-3-(4-bromo-3-methylphenyl)acrylate are obtained in oil form. Yield=55% over steps a, b and c.

d. Preparation of methyl (E)-3-(2-methyl-3'-methylaminobiphenyl-4-yl)acrylate In a manner similar to that of Example (18d), by reaction of 44 mg (10 mol %) of palladium acetate, 136 mg (20 mol %) of dicyclohexylbiphenylphosphine, 500 mg (1.96 mmol, 1 eq) of methyl (E)-3-(4-bromo-3-methylphenyl)acrylate and 355 mg (2.35 mmol, 1.2 eq) of 3-(methylamino)phenylboronic acid (prepared in Example 18a) in 4 ml of dimethylformamide+1 ml of 2M potassium phosphate solution, 390 mg of methyl (E)-3-(2-methyl-3'-methylaminobiphenyl-4-yl)acrylate are obtained in oil form. Yield=70% e. Preparation of methyl 3-(2-methyl-3'-methylaminobiphenyl-4-yl)propanoate

In a manner similar to that of Example (18e), by reaction of 100 mg (25% by mass) of 10% palladium-on-charcoal and 390 mg (1.39 mmol, 1 eq) of methyl (E)-3-(2-methyl-3'-methylaminobiphenyl-4-yl)acrylate in 10 ml of methanol, 360 mg of methyl 3-(2-methyl-3'-methylaminobiphenyl-4-yl)propanoate are obtained in oil form. Yield=92% f. Preparation of methyl 3-[3'-(3-heptyl-1-methylureido)-2-methylbiphenyl-4-yl]propanoate In a manner similar to that of Example (18f), by reaction of 410 μL (2.54 mmol, 2 eq) of heptyl isocyanate and 360 mg (1.27 mmol, 1 eq) of methyl 3-(2-methyl-3'-methylaminobiphenyl-4-yl)propanoate in 8 mL of an 8/2 tetrahydrofuran/triethylamine mixture, 360 mg of methyl 3-[3'-(3-heptyl-1-methylureido)-2-methylbiphenyl-4-yl]propanoate are obtained in oil form. Yield=66% g. Synthesis of 3-[3'-(3-heptyl-1-methylureido)-2-methylbiphenyl-4-yl]propanoic acid 200 mg (5.0 mmol, 4.2 eq) of sodium hydroxide are added to a solution of 360 mg (0.85 mmol, 1 eq) of methyl 3-[3'-(3-heptyl-1-methylureido)-2-methylbiphenyl-4-yl]propanoate in 6 ml of a tetrahydrofuran/methanol mixture (8/2). The reaction mixture is stirred at room temperature for 3 hours. The reaction medium is hydrolyzed with water, acidified with acetic acid solution and extracted with ethyl acetate. The organic phases are combined, washed with sodium chloride solution and dried over sodium sulfate. The solvent is evaporated off and the residual oil is chromatographed on silica (7/3 to 1/1 heptane/ethyl acetate). 185 mg of 3-[3'-(3-heptyl-1-methylureido)-2-methylbiphenyl-4-yl]propanoic acid are obtained in oil form. Yield=53%

$^1$H NMR (CDCl$_3$, 400 MHz): 0.87 (t, 3H); 1.25 (m, 8H); 1.42 (m, 2H); 2.28 (s, 3H); 2.75 (t, 2H); 3.00 (t, 2H); 3.19 (q, 2H); 3.31 (s, 3H); 4.42 (t, 1H); 7.12-7.18 (m, 3H); 7.24 (m, 3H); 7.47 (t, 1H).

Example 20

Synthesis of 3-[3'-[1-methyl-3-(3-phenylpropyl)ureido]biphenyl-4-yl]propanoic acid

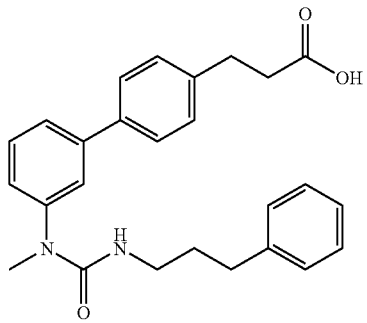

a. Preparation of ethyl 3-{3'-[1-methyl-3-(3-phenylpropyl)ureido]biphenyl-4-yl}propanoate 188 μL (1.2 mmol, 1.5 eq) 3-phenylpropyl isocyanate are added to a solution of 230 mg (0.81 mmol, 1 eq) of ethyl 3-(3'-methylaminobiphenyl-4-yl)propanoate (prepared in Example 7c) in 10 mL of an 8/2 dichloromethane/triethylamine mixture. The reaction medium is stirred at 40° C. for 12 hours and then hydrolyzed with water and extracted with ethyl acetate. The organic phases are combined, washed with sodium chloride solution and dried over sodium sulfate. The solvents are evaporated off and the residual oil is chromatographed on silica (7/3 heptane/ethyl acetate). 348 mg of ethyl 3-{3'-[1-methyl-3-(3-phenylpropyl)ureido]biphenyl-4-yl}propanoate are obtained in solid form. Yield=96% b. Synthesis of 3-[3'-(3-heptyl-1-methylureido)-2-methylbiphenyl-4-yl]propanoic acid 100 mg (2.5 mmol, 3.2 eq) of sodium hydroxide are added to a solution of 348 mg (0.78 mmol, 1 eq) of ethyl 3-{3'-[1-methyl-3-(3-phenylpropyl)ureido]biphenyl-4-yl}propanoate in 6 ml of a tetrahydrofuran/methanol mixture (8/2). The reaction mixture is stirred at room temperature for 12 hours. The reaction medium is hydrolyzed with water, acidified with acetic acid solution and extracted with ethyl acetate. The organic phases are combined, washed with sodium chloride solution and dried over sodium sulfate. The solvent is evaporated off and the residual oil is chromatographed on silica (7/3 to 1/1 heptane/ethyl acetate). 180 mg of 3-[3'-(3-heptyl-1-methylureido)-2-methylbiphenyl-4-yl]propanoic acid are obtained in the form of a tacky solid. Yield=55%

$^1$H NMR (CDCl$_3$, 400 MHz): 1.76-1.82 (m, 2H); 2.59 (t, 2H); 2.75 (t, 2H); 3.04 (t, 2H); 3.24 (q, 2H); 3.32 (s, 3H); 4.44 (t, 1H); 7.10-7.24 (m, 6H); 7.33 (d, 2H); 7.47-7.53 (m, 5H).

Example 21

Synthesis of (E)-3-[5'-(3-heptyl-1-methylureido)-2'-methylbiphenyl-4-yl]acrylic acid

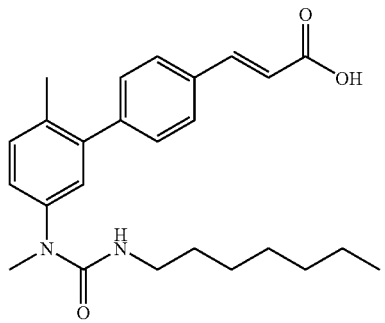

a. Preparation of tert-butyl (3-bromo-4-methylphenyl)carbamate 57.62 g (0.3 mol, 1 eq) of 3-bromo-4-methylaniline are added to a solution of 75.8 g (0.344 mol, 1.15 eq) of di-tert-butyl dicarbonate in 580 mL of 2N sodium hydroxide solution. The reaction medium is refluxed for one hour and stirred at room temperature for 4 hours. The reaction medium is filtered and the solid is washed with water until the filtrate is neutral, and then dried. 90.33 g of tert-butyl (3-bromo-4-methylphenyl)carbamate are obtained in solid form. Crude yield>100% b. Preparation of tert-butyl (3-bromo-4-methylphenyl)methyl carbamate 1.6 g (0.042 mol, 1.2 eq) of 60% sodium hydride are added to a solution of 10.0 g (0.035 mol, 1 eq) of tert-butyl (3-bromo-4-methylphenyl)carbamate in 150 ml of dimethylformamide. The reaction medium is stirred at room temperature for 2 hours and 6.2 mL (0.099 mol, 3 eq) of methyl iodide are then added. The reaction medium is stirred at room temperature for 20 hours and then hydrolyzed in water and extracted with ethyl acetate. The organic phases are combined, washed with water and dried over sodium sulfate. The solvent is evaporated off and 10.4 g of tert-butyl (3-bromo-4-methylphenyl)methyl carbamate are obtained. Yield=100% c. Preparation of (3-bromo-4-methylphenyl)methylamine

A solution of 10.4 g (0.035 mol, 1 eq) of tert-butyl (3-bromo-4-methylphenyl)methyl carbamate in 25 mL of dichloromethane in the presence of 13.5 mL (0.173 mol, 5 eq) of trifluoroacetic acid is stirred at room temperature for 30 hours. The reaction medium is hydrolyzed in water, basified to pH 8-9 with 1N sodium hydroxide solution and extracted with dichloromethane. The organic phases are combined and dried over sodium sulfate. The solvent is evaporated off and 6.39 g of (3-bromo-4-methylphenyl)methylamine are obtained. Yield=91% d. Preparation of Methyl[4-methyl-3-(4,4,5,5-tetramethyl[1,3,2]dioxaborolan-2-yl)phenyl]amine In a manner similar to that of Example (7a), by reaction of 3.2 g (0.016 mol, 1 eq) of (3-bromo-4-methylphenyl)methylamine, 4.06 g (0.016 mol, 1 eq) of pinacol diborane and 4.7 g (0.048 mol, 3 eq) of potassium acetate in the presence of 650 mg (5 mol %) of diphenylphosphinoferrocenepalladium dichloride in 20 ml of dimethylformamide, at 90° C. for 8 hours, 3.28 g of methyl[4-methyl-3-(4,4,5,5-tetramethyl[1,3,2]dioxaborolan-2-yl)phenyl]amine are obtained. Yield=83% e. Preparation of ethyl (E)-3-(2'-methyl-5'-methylaminobiphenyl-4-yl)acrylate In a manner similar to that of Example (18d), by reaction of 45 mg (5 mol %) of palladium acetate, 140 mg (10 mol %) of dicyclohexylbiphenylphosphine, 1.1 g (4.4 mmol, 1.1 eq) of ethyl 4-bromocinnamate and 1.0 g (4.0 mmol, 1 eq) of methyl [4-methyl-3-(4,4,5,5-tetramethyl[1,3,2]dioxaborolan-2-yl)phenyl]amine in 18 ml of dimethylformamide+3 ml of 2M potassium phosphate solution, 805 mg of ethyl (E)-3-(2'-methyl-5'-methylaminobiphenyl-4-yl)acrylate are obtained in oil form. Yield=68% f. Preparation of ethyl (E)-3-[5'-(3-heptyl-1-methylureido)-2'-methylbiphenyl-4-yl]acrylate 660 μL (4.0 mmol, 1.5 eq) of heptyl isocyanate are added to a solution of 805 mg (2.72 mmol, 1 eq) of ethyl (E)-3-(2'-methyl-5'-methylaminobiphenyl-4-yl)acrylate in 8 mL of a 7/1 dichloromethane/triethylamine mixture. The reaction medium is stirred at 50° C. for 12 hours and then hydrolyzed with water and extracted with ethyl acetate. The organic phases are combined, washed with sodium chloride solution and dried over sodium sulfate. The solvents are evaporated off and the residual oil is chromatographed on silica (7/3 heptane/ethyl acetate). 920 mg of ethyl (E)-3-[5'-(3-heptyl-1-methylureido)-2'-methylbiphenyl-4-yl]acrylate are obtained in oil form. Yield=77% g. Synthesis of (E)-3-[5'-(3-heptyl-1-methylureido)-2'-methylbiphenyl-4-yl]acrylic acid In a manner similar to that of Example (19g), by reaction of 200 mg (5.0 mmol, 4.7 eq) of sodium hydroxide and 460 mg (1.05 mmol, 1 eq) of ethyl (E)-3-[5'-(3-heptyl-1-methylureido)-2'-methylbiphenyl-4-yl]acrylate in 6 ml of a tetrahydrofuran/methanol mixture (8/2), and after crystallization from a dichloromethane/pentane mixture, 160 mg of (E)-3-[5'-(3-heptyl-1-methylureido)-2'-methylbiphenyl-4-yl]acrylic acid are obtained in the form of a white powder. (m.p.=159° C.). Yield=37%

$^1$H NMR (CDCl$_3$, 400 MHz): 0.87 (t, 3H); 1.25 (m, 8H); 1.43 (m, 2H); 2.32 (s, 3H); 3.19 (q, 2H); 3.30 (s, 3H); 4.43 (t, 1H); 6.52-6.56 (d, 1H); 7.15-7.20 (m, 2H); 7.33-7.39 (m, 3H); 7.64 (d, 2H); 7.83-7.87 (d, 1H).

Example 22

Synthesis of 3-[5'-(3-heptyl-1-methylureido)-2'-methylbiphenyl-4-yl]propanoic acid

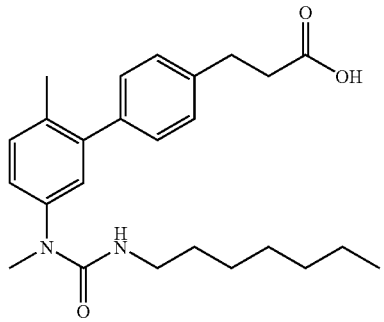

a. Preparation of ethyl 3-[5'-(3-heptyl-1-methylureido)-2'-methylbiphenyl-4-yl]propanoate A solution of 460 mg of ethyl (E)-3-[5'-(3-heptyl-1-methylureido)-2'-methylbiphenyl-4-yl]acrylate (prepared in step 21f) in 10 ml of methanol is stirred for 12 hours at room temperature in the presence of 100 mg (22% by mass) of 10% palladium-on-charcoal under a hydrogen atmosphere. The palladium is filtered off and the solvent is evaporated off. The oil is used directly in the following step.

b. Synthesis of 3-[5'-(3-heptyl-1-methylureido)-2'-methylbiphenyl-4-yl]propanoic acid In a manner similar to that of Example (19g), by reaction of 200 mg (5.0 mmol, 4.7 eq) of sodium hydroxide, the oil obtained above (ethyl 3-[5'-(3-heptyl-1-methylureido)-2'-methylbiphenyl-4-yl]propanoate) in 6 ml of a tetrahydrofuran/methanol mixture (8/2), and after crystallization from pentane, 170 mg of 3-[5'-(3-heptyl-1-methylureido)-2'-methylbiphenyl-4-yl]propanoic acid are obtained in the form of a white powder. (m.p.=104° C.). Yield=39% over the two steps a and b.

$^1$H NMR (CDCl$_3$, 400 MHz): 0.87 (t, 3H); 1.28 (m, 8H); 1.42 (m, 2H); 2.30 (s, 3H); 2.76 (t, 2H); 3.05 (t, 2H); 3.18 (q, 2H); 3.28 (s, 3H); 4.44 (t, 1H); 7.12-7.15 (m, 2H); 7.24-7.32 (m, 5H).

Example 23

Synthesis of (E)-3-[3-fluoro-3'-(3-heptyl-1-methylureido)biphenyl-4-yl]acrylic acid

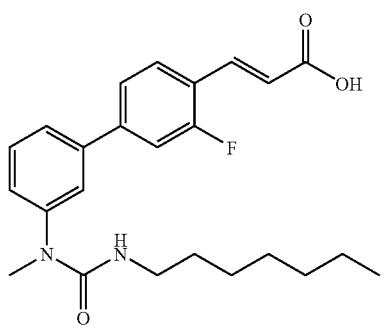

In a manner similar to that of Example (19g), by reaction of 200 mg (5.0 mmol, 4.7 eq) of sodium hydroxide, 210 mg (0.51 mmol, 1 eq) of methyl (E)-3-[3-fluoro-3'-(3-heptyl-1-methylureido)biphenyl-4-yl]acrylate (prepared in Example 3b) in 6 ml of a tetrahydrofuran/methanol mixture (8/2), and after crystallization from pentane, 165 mg of (E)-3-[3-fluoro-3'-(3-heptyl-1-methylureido)biphenyl-4-yl]acrylic acid are obtained in the form of a white powder. (m.p.=148-149° C.). Yield=81%

$^1$H NMR (CDCl$_3$, 400 MHz): 0.87 (t, 3H); 1.25 (m, 8H); 1.44 (m, 2H); 3.21 (q, 2H); 3.35 (s, 3H); 4.40 (t, 1H); 6.61-6.66 (d, 1H); 7.30-7.33 (m, 3H); 7.36-7.38 (m, 3H); 7.52-7.55 (t, 1H); 7.94-7.98 (d, 1H).

Example 24

Synthesis of (E)-3-[2-benzyloxy-3'-(3-heptyl-1-methylureido)biphenyl-4-yl]acrylic acid

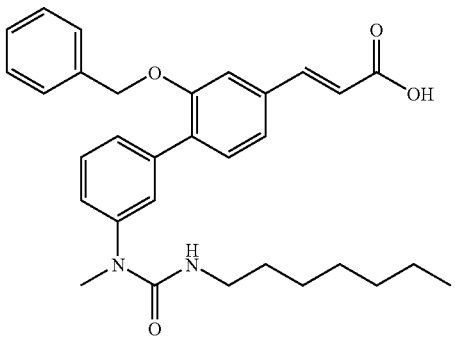

a. Preparation of methyl 3-benzyloxy-4-iodobenzoate 2.35 mL (19.78 mmol, 1.1 eq) of benzyl bromide are added to a solution of 5.0 g (17.98 mmol, 1 eq) of methyl 3-hydroxy-4-iodobenzoate in 30 ml of methyl ethyl ketone in the presence of 5.0 g of potassium carbonate. The reaction medium is heated at 60° C. for 5 hours and then hydrolyzed with water and extracted with ethyl acetate. The organic phases are combined and the solvents are evaporated off. 6.9 g of methyl 3-benzyloxy-4-iodobenzoate in oil form are used in the following reaction without further purification.

b. Preparation of (3-benzyloxy-4-iodophenyl)methanol 1.18 g (54 mmol, 3 eq) of lithium borohydride are added to a solution of 6.9 g of methyl 3-benzyloxy-4-iodobenzoate in 30 ml of tetrahydrofuran. The reaction medium is heated at 60° C. for 12 hours and then hydrolyzed with ammonium chloride solution and extracted with ethyl acetate. The organic phases are combined and the solvents are evaporated off. 6.5 g of (3-benzyloxy-4-iodophenyl)methanol in oil form are used in the following reaction without further purification.

c. Preparation of 3-benzyloxy-4-iodobenzaldehyde 7.8 g (90 mmol, 5 eq) of manganese dioxide are added to a solution of 6.5 g of (3-benzyloxy-4-iodophenyl)methanol in 50 mL of dichloromethane. The reaction medium is stirred at room temperature for 12 hours.

43

The solid is filtered off and the solvent is evaporated off. The residual oil is chromatographed on silica gel (8/2 heptane/ethyl acetate) and then crystallized from pentane. 3.25 g of 3-benzyloxy-4-iodobenzaldehyde are obtained in solid form. Yield=54% over the three steps a, b and c.

d. Preparation of methyl (E)-3-(3-benzyloxy-4-iodophenyl)acrylate 5.0 g (14.95 mmol, 1.8 eq) of methyl triphenylphosphoranylideneacetate are added to a solution of 3.25 g (8.2 mmol, 1 eq) of 3-benzyloxy-4-iodobenzaldehyde in 15 ml of toluene. The reaction mixture is stirred for 1 hour at 90° C. The solvent is evaporated off and the residual oil is then chromatographed on silica gel (8/2 heptane/ethyl acetate) and recrystallized from dichloromethane/heptane. 2.59 g of methyl (E)-3-(3-benzyloxy-4-iodophenyl)acrylate are obtained in solid form. Yield=68% e. Preparation of methyl (E)-3-[2-benzyloxy-3'-(3-heptyl-1-methylureido)biphenyl-4-yl]acrylate In a manner similar to that of Example (18d), by reaction of 50 mg (10 mol %) of palladium acetate, 180 mg (20 mol %) of dicyclohexylbiphenylphosphine, 1.0 g (2.53 mmol, 1 eq) of methyl (E)-3-(3-benzyloxy-4-iodophenyl)acrylate and 1.0 g (2.79 mmol, 1.1 eq) of 3-heptyl-1-methyl-1-[3-(4,4,5,5-tetramethyl[1,3,2]dioxaborolan-2-yl)phenyl]urea (prepared in Example 1e) in 8 ml of dimethylformamide+2 ml of 2M potassium phosphate solution, 980 mg of methyl (E)-3-[2-benzyloxy-3'-(3-heptyl-1-methylureido)biphenyl-4-yl]acrylate are obtained in oil form. Yield=75% f. Synthesis of (E)-3-[2-benzyloxy-3'-(3-heptyl-1-methylureido)biphenyl-4-yl]acrylic acid In a manner similar to that of Example (19g), by reaction of 200 mg (5.0 mmol, 12.8 eq) of sodium hydroxide and 200 mg (0.39 mmol, 1 eq) of methyl (E)-3-[2-benzyloxy-3'-(3-heptyl-1-methylureido)biphenyl-4-yl]acrylate in 6 ml of a tetrahydrofuran/methanol mixture (8/2), and after crystallization from pentane, 125 mg of (E)-3-[2-benzyloxy-3'-(3-heptyl-1-methylureido)biphenyl-4-yl]acrylic acid are obtained in the form of a white powder (m.p.=115-116° C.). Yield=64%

$^1$H NMR (CDCl$_3$, 400 MHz): 0.86 (t, 3H); 1.26 (m, 8H); 1.38 (m, 2H); 3.12 (q, 2H); 3.24 (s, 3H); 4.41 (t, 1H); 5.16 (s, 2H); 6.48-6.52 (d, 1H); 7.23-7.53 (m, 12H); 7.79-7.83 (d, 1H).

Example 25

Synthesis of 3-[3'-(3-heptyl-1-methylureido)-2-propoxybiphenyl-4-yl]propanoic acid

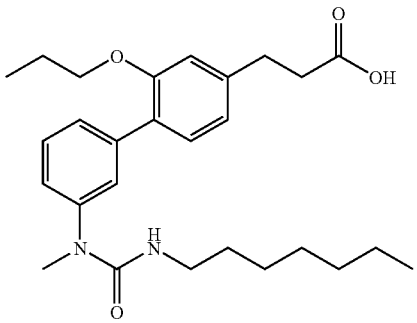

44 a. Preparation of methyl 3-[3'-(3-heptyl-1-methylureido)-2-propoxybiphenyl-4-yl]propanoate 100 μL (1.0 mmol, 1.5 eq) of 1-iodopropane are added to a solution of 285 mg (0.67 mmol, 1 eq) of methyl 3-[3'-(3-heptyl-1-methylureido)-2-hydroxybiphenyl-4-yl]propanoate (prepared in Example 15f) in 6 ml of methyl ethyl ketone in the presence of 200 mg (1.45 mmol, 2.2 eq) of potassium carbonate. The reaction medium is heated at 60° C. for 16 hours. The solid is filtered off and the solvent is evaporated off. The methyl 3-[3'-(3-heptyl-1-methylureido)-2-propoxybiphenyl-4-yl]propanoate obtained in oil form is used in the following reaction without further purification.

b. Synthesis of 3-[3'-(3-heptyl-1-methylureido)-2-propoxybiphenyl-4-yl]propanoic acid In a manner similar to that of Example (19g), by reaction of 200 mg (5.0 mmol, ~8 eq) of sodium hydroxide and methyl 3-[3'-(3-heptyl-1-methylureido)-2-propoxybiphenyl-4-yl]propanoate, prepared in the preceding step, in 6 ml of a tetrahydrofuran/methanol mixture (8/2), and after crystallization from pentane, 180 mg of 3-[3'-(3-heptyl-1-methylureido)-2-propoxybiphenyl-4-yl]propanoic acid are obtained in the form of a white powder (m.p.=79-80° C.). Yield=59% over the two steps b and c.

$^1$H NMR (CDCl$_3$, 400 MHz): 0.87 (t, 3H); 0.98 (t, 3H); 1.23-1.29 (m, 8H); 1.41 (m, 2H); 1.72-1.79 (m, 2H); 2.75 (t, 2H); 3.02 (t, 2H); 3.17 (q, 2H); 3.30 (s, 3H); 3.96 (t, 2H); 4.43 (t, 1H); 6.86 (s, 1H); 6.90 (d, 1H); 7.19 (d, 1H); 7.26 (d, 1H); 7.42-7.49 (m, 3H).

Example 26

Synthesis of 3-[2-butoxy-3'-(3-heptyl-1-methylureido)biphenyl-4-yl]propanoic acid

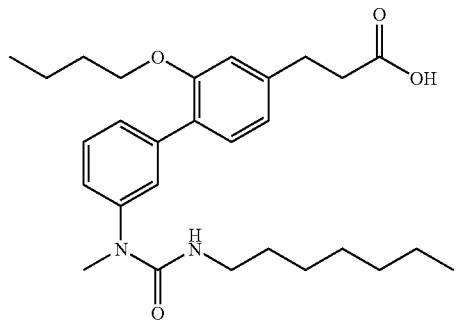

a. Preparation of methyl 3-[2-butoxy-3'-(3-heptyl-1-methylureido)biphenyl-4-yl]propanoate In a manner similar to that of Example (25a), by reaction of 114 μL (1.0 mmol, 1.5 eq) of 1-iodobutane and 285 mg (0.67 mmol, 1 eq) of methyl 3-[3'-(3-heptyl-1-methylureido)-2-hydroxybiphenyl-4-yl]propanoate (prepared in Example 15f) in 6 ml of methyl ethyl ketone in the presence of 200 mg of potassium carbonate, methyl 3-[2-butoxy-3'-(3-heptyl-1-methylureido)biphenyl-4-yl]propanoate is obtained in oil form and is used in the following reaction without further purification.

b. Synthesis of 3-[2-butoxy-3'-(3-heptyl-1-methylureido)biphenyl-4-yl]propanoic acid In a manner similar to that of Example (19g), by reaction of 200 mg (5.0 mmol, ~8 eq) of sodium hydroxide and methyl 3-[2-butoxy-3'-(3-heptyl-1-methylureido)biphenyl-4-yl]propanoate, prepared in the preceding step, in 6 ml of a tetrahydrofuran/methanol mixture (8/2), and after crystallization from pentane, 200 mg of 3-[2-butoxy-3'-(3-heptyl-1-methylureido)biphenyl-4-yl]propanoic acid are obtained in the form of a white powder (m.p.=77-78° C.). Yield=64% over the two steps a and b.

$^1$H NMR (CDCl$_3$, 400 MHz): 0.87 (t, 3H); 0.93 (t, 3H); 1.24 (m, 8H); 1.38-1.46 (m, 4H); 1.69-1.76 (m, 2H); 2.75 (t, 2H); 3.02 (t, 2H); 3.17 (q, 2H); 3.31 (s, 3H); 3.99 (t, 2H); 4.43 (t, 1H); 6.87 (s, 1H); 6.90 (d, 1H); 7.19 (d, 1H); 7.26 (d, 1H); 7.44-7.49 (m, 3H).

Example 27

Synthesis of (E)-3-[3'-(1-ethyl-3-heptylureido)biphenyl-4-yl]acrylic acid

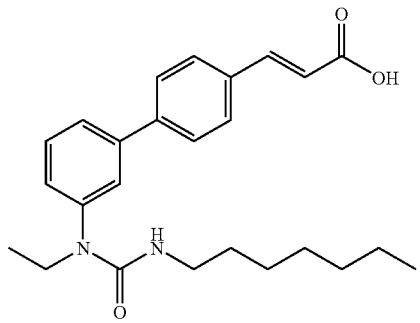

a. Preparation of N-(3-bromophenyl)acetamide 691 mL of acetic anhydride are added to a solution cooled to 10° C. of 1200 g (6.976 mol, 1 eq) of 3-bromoaniline in 6 L of dichloromethane in the presence of 1.07 L (7.67 mol, 1.1 eq) of triethylamine and 25.6 g (0.209 mol, 0.03 eq) of 4-(dimethylamino)pyridine. The reaction medium is stirred at room temperature for 4 hours and then hydrolyzed with 850 mL of 1N hydrochloric acid solution, and the phases are separated by settling. The organic phase is washed with 0.5N hydrochloric acid solution and then with water, and the solvent is evaporated off. After recrystallization from diisopropyl ether/heptane, 1506.1 g of N-(3-bromophenyl)acetamide are obtained in solid form. Yield=100% b. Preparation of N-(3-bromophenyl)-N-ethylacetamide 820 mg (20.5 mmol, 1.1 eq) of 60% sodium hydride are added to a solution of 4.0 g (18.7 mmol, 1 eq) of N-(3-bromophenyl)acetamide and 1.80 mL (22.4 mmol, 1.2 eq) of ethyl iodide in 15 ml of tetrahydrofuran in the presence of 1.5 ml of dimethylformamide. The reaction medium is stirred at room temperature for 12 hours and then hydrolyzed with water and extracted with ethyl acetate. The organic phases are combined, washed with sodium chloride solution and dried over sodium sulfate. The solvents are evaporated off and the N-(3-bromophenyl)-N-ethylacetamide obtained in oil form is used in the following reaction without further purification.

c. Preparation of (3-bromophenyl)ethylamine 10 ml of 2.5 M potassium hydroxide solution are added to a solution of N-(3-bromophenyl)-N-ethylacetamide (obtained in the preceding step) in 10 ml of ethanol. The reaction medium is refluxed for 12 hours and then hydrolyzed with water and extracted with ethyl acetate. The organic phases are combined, washed with sodium chloride solution and dried over sodium sulfate. The solvents are evaporated off and the residual oil is chromatographed on silica (7/3 heptane/ethyl acetate). 2.3 g of (3-bromophenyl)ethylamine are obtained in oil form. Yield=62% over the two steps.

d. Preparation of 1-(3-bromophenyl)-1-ethyl-3-heptylurea

In a manner similar to that of Example (11 ac), by reaction of 1.6 mL (10 mmol, 2 eq) of heptyl isocyanate and 1.0 g (5.0 mmol, 1 eq) of (3-bromophenyl)ethylamine, 1.6 g of 1-(3-bromophenyl)-1-ethyl-3-heptylurea are obtained. Yield=94% e. Preparation of 1-ethyl-1-(4'-formylbiphenyl-3-yl)-3-heptylurea 135 mg (5 mol %) of tetrakis(triphenylphosphine)palladium are added to a solution of 800 mg (2.34 mmol, 1 eq) of 1-(3-bromophenyl)-1-ethyl-3-heptylurea and 460 mg (3.0 mmol, 1.3 eq) of 4-formylphenylboronic acid in 10 mL of a mixture of dimethylformamide and of 2M potassium phosphate solution (8/2). The reaction mixture is stirred for 3 hours at 90° C. The reaction is stopped by addition of 50 mL of water and then extracted with ethyl acetate. The organic phases are combined and dried over sodium sulfate. The solvents are evaporated off and the residue is then chromatographed on silica gel (70/30 heptane/ethyl acetate). 740 mg of 1-ethyl-1-(4'-formylbiphenyl-3-yl)-3-heptylurea are obtained in oil form. Yield=86% f. Preparation of methyl (E)-3-[3'-(1-ethyl-3-heptylureido)biphenyl-4-yl]acrylate 1.0 g (3 mmol, 1.5 eq) of methyl triphenylphosphoranylideneacetate are added to a solution of 740 mg (2.02 mmol, 1 eq) of 1-ethyl-1-(4'-formylbiphenyl-3-yl)-3-heptylurea in 8 ml of toluene. The reaction mixture is heated at 90° C. for 1 hour. The solvent is evaporated off and the residual oil is then chromatographed on silica gel (8/2 heptane/ethyl acetate). 775 mg of methyl (E)-3-[3'-(1-ethyl-3-heptylureido)biphenyl-4-yl]acrylate are obtained in the form of an off-white solid. Yield=91% g. Synthesis of (E)-3-[3'-(1-ethyl-3-heptylureido)biphenyl-4-yl]acrylic acid

In a manner similar to that of Example (19g), by reaction of 400 mg (10 mmol, 5.5 eq) of sodium hydroxide and 775 mg (1.83 mmol, 1 eq) of methyl (E)-3-[3'-(1-ethyl-3-heptylureido)biphenyl-4-yl]acrylate in 15 ml of a tetrahydrofuran/methanol mixture (8/2), and after crystallization from dichloromethane/heptane, 580 mg of (E)-3-[3'-(1-ethyl-3-heptylureido)biphenyl-4-yl]acrylic acid are obtained in the form of a white powder (m.p.=116° C.). Yield=77%

$^1$H NMR (CDCl$_3$, 400 MHz): 0.87 (t, 3H); 1.16 (t, 3H); 1.24 (m, 8H); 1.42 (m, 2H); 3.19 (m, 2H); 3.82 (m, 2H); 4.21 (m, 1H); 6.52-6.56 (d, 1H); 7.26 (m, 2H); 7.50-7.66 (m, 6H); 7.83-7.87 (d, 1H).

Example 28

Synthesis of (E)-3-[3'-(3-heptyl-1-propylureido)biphenyl-4-yl]acrylic acid

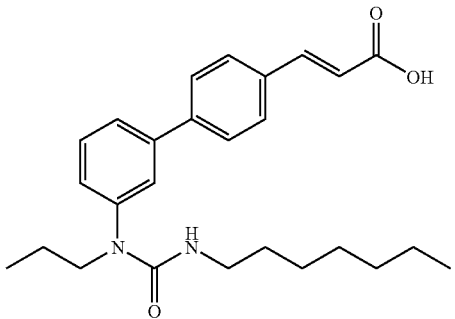

a. Preparation of N-(3-bromophenyl)-N-propylacetamide

In a manner similar to that of Example (27b), by reaction of 820 mg (20.5 mmol, 1.1 eq) of 60% sodium hydride, 4.0 g (18.7 mmol, 1 eq) of N-(3-bromophenyl)acetamide (prepared in Example 27a) and 2.20 mL (22.4 mmol, 1.2 eq) of 1-iodopropane in 15 ml of tetrahydrofuran in the presence of 1.5 ml of dimethylformamide, N-(3-bromophenyl)-N-propylacetamide is obtained in oil form and is used in the following reaction without further purification.

b. Preparation of (3-bromophenyl)propylamine

In a manner similar to that of Example (27c), by reaction of 10 mL of 2.5 M potassium hydroxide solution and N-(3-bromophenyl)-N-propylacetamide (obtained in the preceding step) in 10 mL of ethanol, 2.0 g of (3-bromophenyl)propylamine are obtained in oil form. Yield=50% over the two steps a and b.

c. Preparation of 1-(3-bromophenyl)-1-propyl-3-heptylurea

In a manner similar to that of Example (11a), by reaction of 1.6 mL (10 mmol, 2.1 eq) of heptyl isocyanate and 1.0 g (4.7 mmol, 1 eq) of (3-bromophenyl)propylamine, 1.45 g of 1-(3-bromophenyl)-1-propyl-3-heptylurea are obtained. Yield=90% d. Preparation of 1-propyl-1-(4'-formylbiphenyl-3-yl)-3-heptylurea 135 mg (5 mol %) of tetrakis(triphenyl-phosphine)palladium are added to a solution of 830 mg (2.34 mmol, 1 eq) of 1-(3-bromophenyl)-1-propyl-3-heptylurea and 460 mg (3.0 mmol, 1.3 eq) of 4-formylphenylboronic acid in 10 mL of a mixture of dimethylformamide and of 2M potassium phosphate solution (8/2). The reaction mixture is stirred for 3 hours at 90° C. The reaction is stopped by addition of 50 mL of water and then extracted with ethyl acetate. The organic phases are combined and dried over sodium sulfate. The solvents are evaporated off and the residue is then chromatographed on silica gel (70/30 heptane/ethyl acetate). 735 mg of 1-propyl-1-(4'-formylbiphenyl-3-yl)-3-heptylurea are obtained in oil form. Yield=82% e. Preparation of methyl (E)-3-[3'-(1-propyl-3-heptylureido)biphenyl-4-yl]acrylate In a manner similar to that of Example (27f), by reaction of 1.0 g (3 mmol, 1.5 eq) of methyl triphenylphosphoranylideneacetate and 735 mg (1.93 mmol, 1 eq) of 1-propyl-1-(4'-formylbiphenyl-3-yl)-3-heptylurea in 8 ml of toluene, 680 mg of methyl (E)-3-[3'-(1-propyl-3-heptylureido)biphenyl-4-yl]acrylate are obtained in the form of an off-white solid. Yield=81% f. Synthesis of (E)-3-[3'-(1-propyl-3-heptylureido)biphenyl-4-yl]acrylic acid

In a manner similar to that of Example (19g), by reaction of 400 mg (10 mmol, 6.4 eq) of sodium hydroxide and 680 mg (1.55 mmol, 1 eq) of methyl (E)-3-[3'-(1-propyl-3-heptylureido)biphenyl-4-yl]acrylate in 15 ml of a tetrahydrofuran/methanol mixture (8/2), and after crystallization from dichloromethane/heptane, 560 mg of (E)-3-[3'-(1-propyl-3-heptylureido)biphenyl-4-yl]acrylic acid are obtained in the form of a white powder (m.p.=126° C.). Yield=85%

$^1$H NMR (CDCl$_3$, 400 MHz): 0.87 (t, 3H); 0.92 (t, 3H); 1.24 (m, 8H); 1.40-1.45 (m, 2H); 1.53-1.63 (m, 2H); 3.19 (m, 2H); 3.71 (m, 2H); 4.22 (m, 1H); 6.52-6.56 (d, 1H); 7.26 (m, 2H); 7.50-7.69 (m, 6H); 7.83-7.87 (d, 1H).

Example 29

Synthesis of (E)-3-[3,5-difluoro-3'-(3-heptyl-1-methylureido)biphenyl-4-yl]acrylic acid

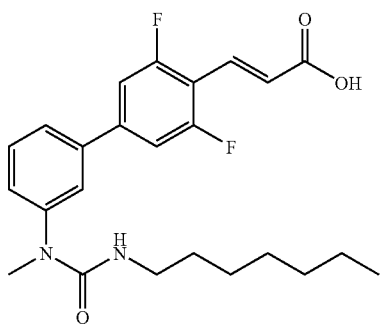

a. Preparation of 4-bromo-2,6-difluorobenzaldehyde 0.7 g (7.7 mmol 10 eq) of manganese dioxide is added to a solution of 1.0 g (0.77 mmol, 1 eq) of 2,6-difluoro-4-bromobenzylalcool in 15 mL of dichloromethane. The reaction medium is stirred at room temperature for 48 hours.

The solid is filtered off and the solvent is evaporated off. The residual oil is chromatographed on silica gel (8/2 heptane/ethyl acetate) and 760 mg of 4-bromo-2,6-difluorobenzaldehyde are obtained. Yield=76% b. Preparation of methyl 3-(4-bromo-2,6-difluorophenyl)acrylate

In a manner similar to that of Example (3a), by reaction of 1.7 g (5.15 mmol, 1.5 eq) of methyl triphenylphosphoranylideneacetate and 760 mg (3.44 mmol, 1 eq) of 4-bromo-2,6-difluorobenzaldehyde in 15 ml of toluene, 550 mg of methyl 3-(4-bromo-2,6-difluorophenyl)acrylate are obtained in solid form. Yield=57% c. Preparation of methyl (E)-3-[3,5-difluoro-3'-(3-heptyl-1-methylureido)biphenyl-4-yl]acrylate In a manner similar to that of Example (1f), by reaction of 550 mg (1.98 mmol, 1 eq) of methyl 3-(4-bromo-2,6-difluorophenyl)acrylate, 965 mg (2.58 mmol, 1.3 eq) 3-heptyl-1-methyl-1-[3-(4,4,5,5-tetramethyl[1,3,2]dioxaborolan-2-yl)phenyl]urea (prepared in Example 1e) and 100 mg (5 mol %) of tetrakis(triphenylphosphine)palladium in 10 mL of a 6/1 mixture of dimethylformamide and of 2M potassium phosphate solution, 630 mg of methyl (E)-3-[3,5-difluoro-3'-(3-heptyl-1-methylureido)biphenyl-4-yl]acrylate are obtained in oil form. Yield=72% d. Synthesis of (E)-3-[3,5-difluoro-3'-(3-heptyl-1-methylureido)biphenyl-4-yl]acrylic acid In a manner similar to that of Example (19g), by reaction of 400 mg (10 mmol, 7.0 eq) of sodium hydroxide and 630 mg (1.41 mmol, 1 eq) of methyl (E)-3-[3,5-difluoro-3'-(3-heptyl-1-methylureido)biphenyl-4-yl]acrylate in 15 ml of a tetrahydrofuran/methanol mixture (8/2), and after crystallization from dichloromethane/heptane, 450 mg of (E)-3-[3,5-difluoro-3'-(3-heptyl-1-methylureido)biphenyl-4-yl]acrylic acid are obtained in the form of a white powder (m.p.=136° C.). Yield=74%

$^1$H NMR (CDCl$_3$, 400 MHz): 0.86 (m, 3H); 1.25 (m, 8H); 1.44 (m, 2H); 3.21 (m, 2H); 3.34 (s, 3H); 4.37 (m, 1H); 6.80-6.86 (d, 1H); 7.20-7.23 (d, 2H); 7.34 (d, 1H); 7.50-7.57 (m, 3H); 7.88-7.94 (d, 1H).

Example 30

Synthesis of 3-[3'-(1-ethyl-3-heptylureido)biphenyl-4-yl]propanoic acid

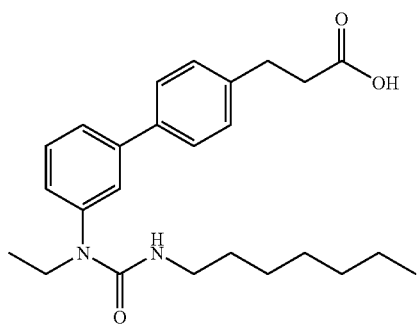

A solution of 400 mg (0.98 mmol, 1 eq) of (E)-3-[3'-(1-ethyl-3-heptylureido)biphenyl-4-yl]acrylic acid (prepared in Example 27 g) in 10 mL of ethyl acetate in the presence of 0.2 ml of methanol is stirred for 4 hours at room temperature in the presence of 200 mg (50% by mass) of 10% palladium-on-charcoal under a hydrogen atmosphere. The reaction medium is filtered through Celite and then evaporated to dryness. After crystallization from ethyl ether/pentane, 265 mg of 3-[3'-(1-ethyl-3-heptylureido)biphenyl-4-yl]propanoic acid are obtained in the form of a white powder (m.p.=70° C.). Yield=66%

$^1$H NMR (CDCl$_3$, 400 MHz): 0.86 (t, 3H); 1.15 (t, 3H); 1.23 (m, 8H); 1.42 (m, 2H); 2.75 (t, 2H); 3.05 (t, 2H); 3.17 (m, 2H); 3.79 (q, 2H); 4.22 (t, 1H); 7.19 (d, 1H); 7.34 (d, 2H); 7.45-7.57 (m, 5H).

Example 31

Synthesis of 3-[3'-(3-heptyl-1-propylureido)biphenyl-4-yl]propanoic acid

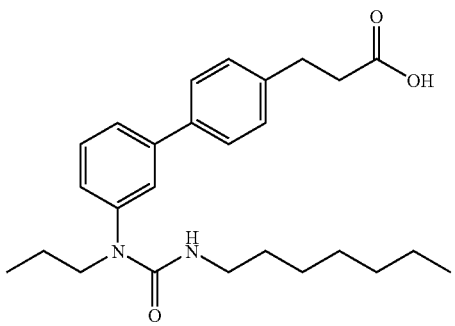

In a manner similar to that of Example (18e), by reaction of 400 mg (0.95 mmol, 1 eq) of (E)-3-[3'-(1-propyl-3-heptylureido)biphenyl-4-yl]acrylic acid (prepared in Example 28f) and 200 mg (50% by mass) of 10% palladium-on-charcoal in 10 mL of ethyl acetate in the presence of 0.2 ml of methanol, 250 mg of 3-[3'-(1-propyl-3-heptylureido)biphenyl-4-yl]propanoic acid are obtained in the form of a white powder (m.p.=79° C.). Yield=63%

$^1$H NMR (CDCl$_3$, 400 MHz): 0.86 (t, 3H); 0.90 (t, 3H); 1.23 (m, 8H); 1.41 (m, 2H); 1.51-1.61 (m, 2H); 2.75 (t, 2H); 3.05 (t, 2H); 3.17 (m, 2H); 3.99 (m, 2H); 4.23 (m, 1H); 7.19 (d, 1H); 7.34 (d, 2H); 7.44-7.55 (m, 5H).

Example 32

Synthesis of 3-[3,5-difluoro-3'-(3-heptyl-1-methylureido)biphenyl-4-yl]propanoic acid

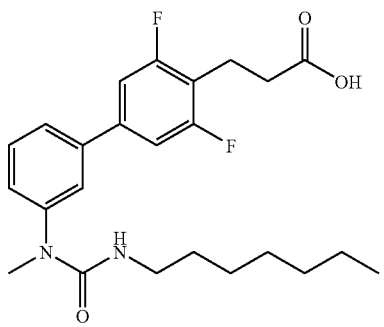

In a manner similar to that of Example (18e), by reaction of 300 mg (0.69 mmol, 1 eq) of (E)-3-[3,5-difluoro-3'-(3-heptyl-1-methylureido)biphenyl-4-yl]acrylic acid (prepared in Example 29d) and 200 mg (67% by mass) of 10% palladium-on-charcoal in 10 mL of ethyl acetate in the presence of 0.2 ml of methanol, 130 mg of 3-[3,5-difluoro-3'-(3-heptyl-1-methylureido)biphenyl-4-yl]propanoic acid are obtained in the form of a white powder (m.p.=86° C.). Yield=44%

¹H NMR (CDCl₃, 400 MHz): 0.86 (t, 3H); 1.24 (m, 8H); 1.43 (m, 2H); 2.72 (t, 2H); 3.08 (t, 2H); 3.19 (q, 2H); 3.33 (s, 3H); 4.38 (t, 1H); 7.11 (d, 2H); 7.30 (s, 1H); 7.45 (s, 1H); 7.47-7.54 (m, 2H).

Example 33

Synthesis of 3-{3'-[3-(4-butoxyphenyl)-1-methylureido]biphenyl-4-yl}propanoic acid

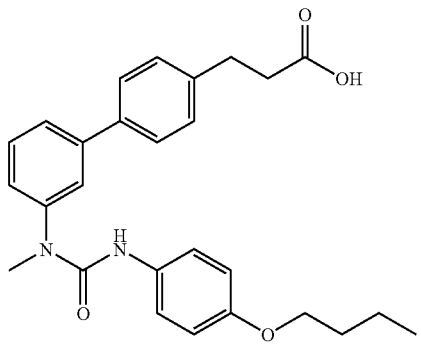

a. Preparation of ethyl 3-{3'-[3-(4-butoxyphenyl)-1-methylureido]biphenyl-4-yl}propanoate In a manner similar to that of Example (5a), by reaction of 574 µl (3.17 mmol, 3 eq) of 4-butoxyphenyl isocyanate and 300 mg (1.06 mmol, 1 eq) of ethyl 3-(3'-methylaminobiphenyl-4-yl)propanoate at 100° C. by microwave for 15 minutes, 490 mg of ethyl 3-{3'-[3-(4-butoxyphenyl)-1-methylureido]biphenyl-4-yl}propanoate are obtained in the form of a white solid. Yield=97% b. Synthesis of 3-{3'-[3-(4-butoxyphenyl)-1-methylureido]biphenyl-4-yl}propanoic acid In a manner similar to that of Example (19g), by reaction of 200 mg (5.0 mmol, 4.8 eq) of sodium hydroxide and 490 mg (1.03 mmol, 1 eq) of ethyl 3-{3'-[3-(4-butoxyphenyl)-1-methylureido]biphenyl-4-yl}propanoate in 6 ml of a tetrahydrofuran/methanol mixture (8/2), and after recrystallization from ethyl acetate/heptane, 330 mg of 3-{3'-[3-(4-butoxyphenyl)-1-methylureido]biphenyl-4-yl}propanoic acid are obtained in the form of white crystals. (m.p.=165° C.). Yield=71%

¹H NMR (CDCl₃, 400 MHz): 0.95 (t, 3H); 1.43-1.48 (m, 2H); 1.68-1.75 (m, 2H); 2.73 (t, 2H); 3.01 (t, 2H); 3.37 (s, 3H); 3.89 (t, 2H); 6.18 (s, 1H); 6.77 (d, 2H); 7.16 (d, 2H); 7.29-7.32 (m, 3H); 7.51-7.56 (m, 5H).

Example 34

Synthesis of 3-{3'-[3-(4-butoxyphenyl)-1-ethylureido]biphenyl-4-yl}propanoic acid

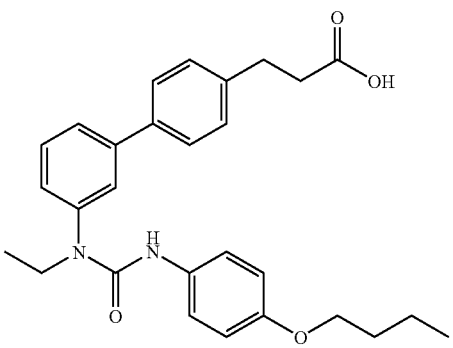

a. Preparation of ethyl (E)-3-[4-(4,4,5,5-tetramethyl[1,3,2]dioxaborolan-2-yl)phenyl]acrylate In a manner similar to that of Example (1e), by reaction of 7.0 g (27 mmol, 1 eq) of ethyl 4-bromocinnamate, 8.0 g (81 mmol, 3 eq) of potassium acetate and 8.3 g (33 mmol, 1.2 eq) of pinacol diborane in the presence of 980 mg (5 mol %) of diphenylphosphinoferrocenepalladium dichloride in 50 ml of dimethylformamide, 8.0 g of ethyl (E)-3-[4-(4,4,5,5-tetramethyl[1,3,2]dioxaborolan-2-yl)phenyl]acrylate are obtained in oil form. Yield=98% b. Preparation of ethyl 3-[4-(4,4,5,5-tetramethyl[1,3,2]dioxaborolan-2-yl)phenyl]propanoate In a manner similar to that of Example (18e), by reaction of 400 mg (5% by mass) of 10% palladium-on-charcoal and 8.0 g (1.39 mmol, 1 eq) of ethyl (E)-3-[4-(4,4,5,5-tetramethyl[1,3,2]dioxaborolan-2-yl)phenyl]acrylate in 30 ml of methanol, 7.8 g of ethyl 3-[4-(4,4,5,5-tetramethyl[1,3,2]dioxaborolan-2-yl)phenyl]propanoate are obtained in the form of a colorless oil. Yield=96% c. Preparation of ethyl 3-(3'-ethylaminobiphenyl-4-yl)propanoate

In a manner similar to that of Example (1f), by reaction of 1.5 g (4.93 mmol, 1 eq) of ethyl 3-[4-(4,4,5,5-tetramethyl[1,3,2]dioxaborolan-2-yl)phenyl]propanoate, 1.28 g (6.41 mmol, 1.3 eq) of (3-bromophenyl)ethylamine (prepared in Example 27c) and 280 mg (5 mol %) of tetrakis(triphenylphosphine)-palladium in 15 mL of a 6/1 mixture of dimethylformamide and of 2M potassium phosphate solution, and after crystallization from pentane, 700 mg of ethyl (3-(3'-ethylaminobiphenyl-4-yl)propanoate are obtained in the form of a white solid. Yield=48% d. Preparation of ethyl 3-{3'-[3-(4-butoxyphenyl)-1-ethylureido]biphenyl-4-yl}propanoate In a manner similar to that of Example (11a), by reaction of 543 µl (3.0 mmol, 3 eq) of 4-butoxyphenyl isocyanate and 300 mg (1.0 mmol, 1 eq) of ethyl 3-(3'-methylaminobiphenyl-4-yl)propanoate, 460 mg of ethyl 3-{3'-[3-(4-butoxyphenyl)-1-ethylureido]biphenyl-4-yl}propanoate are obtained in the form of a colorless oil. Yield=94% e. Synthesis of 3-{3'-[3-(4-butoxyphenyl)-1-ethylureido]biphenyl-4-yl}propanoic acid In a manner similar to that of Example (19g), by reaction of 200 mg (5.0 mmol, 4.8 eq) of sodium hydroxide and 460 mg (0.94 mmol, 1 eq) of ethyl 3-{3'-[3-(4-butoxyphenyl)-1-ethylureido]bipiphenyl-4-yl}propanoate in 6 ml of a tetrahydrofuran/methanol mixture (8/2), and after crystallization from pentane, 118 mg of 3-{3'-[3-(4-butoxyphenyl)-1-ethylureido]biphenyl-4-yl}propanoic acid are obtained in the form of a white powder (m.p.=102-103° C.). Yield=27%

$^1$H NMR (CDCl$_3$, 400 MHz): 0.94 (t, 3H); 1.19 (t, 3H); 1.40-1.50 (m, 2H); 1.68-1.75 (m, 2H); 2.72 (t, 2H); 3.02 (t, 2H); 3.82 (m, 2H); 3.89 (t, 2H); 6.02 (s, 1H); 6.77 (d, 2H); 7.16 (d, 2H); 7.27-7.32 (m, 3H); 7.51-7.58 (m, 5H).

Example 35

Synthesis of 3-[2-cyclopropylmethoxy-3'-(3-heptyl-1-methylureido)biphenyl-4-yl]propanoic acid

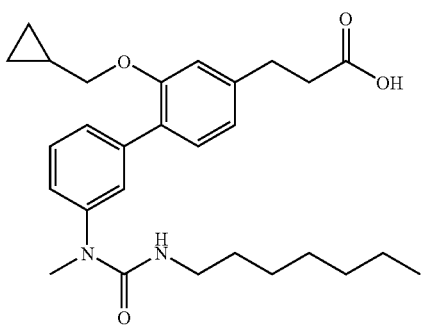

a. Preparation of methyl 3-[2-cyclopropylmethoxy-3'-(3-heptyl-1-methylureido)biphenyl-4-yl]propanoate In a manner similar to that of Example (25a), by reaction of 170 μL (1.75 mmol, 1.5 eq) of methylcyclopropyl bromide and 500 mg (1.17 mmol, 1 eq) of methyl 3-[3'-(3-heptyl-1-methylureido)-2-hydroxybiphenyl-4-yl]propanoate (prepared in Example 15f) in 10 ml of methyl ethyl ketone in the presence of 500 mg (3.61 mmol, 3 eq) of potassium carbonate, methyl 3-[2-cyclopropylmethoxy-3'-(3-heptyl-1-methylureido)biphenyl-4-yl]propanoate is obtained in oil form and is used in the following reaction without further purification.

b. Synthesis of 3-[2-cyclopropylmethoxy-3'-(3-heptyl-1-methylureido)biphenyl-4-yl]propanoic acid In a manner similar to that of Example (19g), by reaction of 400 mg (10.0 mmol, 4.8 eq) of sodium hydroxide and methyl 3-[2-cyclopropylmethoxy-3'-(3-heptyl-1-methylureido)biphenyl-4-yl]propanoate, obtained in the preceding step, in 10 ml of a tetrahydrofuran/methanol mixture (8/2), and after crystallization from pentane, 426 mg of 3-[2-cyclopropylmethoxy-3'-(3-heptyl-1-methylureido)biphenyl-4-yl]propanoic acid are obtained in the form of a white powder (m.p.=64° C.). Yield=78% over the two steps $^1$H NMR (DMSO-d6, 400 MHz): 0.29 (m, 2H); 0.51 (m, 2H); 0.85 (t, 3H); 1.17-1.21 (m, 8H); 1.37 (m, 2H); 2.57 (t, 2H); 2.84 (t, 2H); 2.99 (m, 2H); 3.18 (s, 3H); 3.86 (d, 2H); 5.92 (t, 1H); 6.88 (d, 1H); 6.97 (s, 1H); 7.17 (d, 1H); 7.24 (d, 1H); 7.38-7.43 (m, 3H).

Example 36

Synthesis of 3-[2-ethoxy-3'-(3-heptyl-1-methylureido)biphenyl-4-yl]propanoic acid

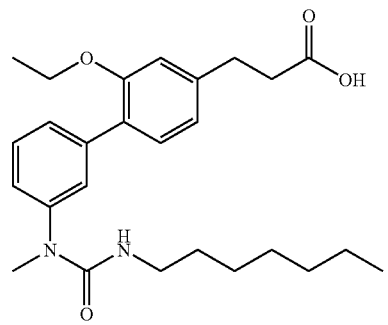

a. Preparation of methyl 3-[2-ethoxy-3'-(3-heptyl-1-methylureido)biphenyl-4-yl]propanoate In a manner similar to that of Example (25a), by reaction of 200 μL (2.46 mmol, 3 eq) of 1-iodoethane and 350 mg (0.82 mmol, 1 eq) of methyl 3-[3'-(3-heptyl-1-methylureido)-2-hydroxybiphenyl-4-yl]propanoate (prepared in Example 15f) in 6 ml of methyl ethyl ketone in the presence of 500 mg (3.61 mmol, 4.4 eq) of potassium carbonate at 80° C. for 5 hours, methyl 3-[2-ethoxy-3'-(3-heptyl-1-methylureido)biphenyl-4-yl]propanoate is obtained in oil form and is used in the following reaction without further purification.

b. Synthesis of 3-[2-ethoxy-3'-(3-heptyl-1-methylureido)biphenyl-4-yl]propanoic acid In a manner similar to that of Example (19g), by reaction of 400 mg (10.0 mmol, 4.8 eq) of sodium hydroxide and methyl 3-[2-ethoxy-3'-(3-heptyl-1-methylureido)biphenyl-4-yl]propanoate, obtained in the preceding step, in 10 ml of a tetrahydrofuran/methanol mixture (8/2), and after crystallization from pentane/isopropyl ether, 246 mg of 3-[2-ethoxy-3'-(3-heptyl-1-methylureido)biphenyl-4-yl]propanoic acid are obtained in the form of a white powder (m.p.=64° C.). Yield=78% over the two steps $^1$H NMR (CDCl$_3$, 400 MHz): 0.84 (t, 3H); 1.22-1.27 (m, 8H); 1.35 (t, 3H); 1.40 (m, 2H); 2.73 (t, 2H); 3.00 (t, 2H); 3.16 (q, 2H); 3.29 (s, 3H); 4.05 (q, 2H); 4.44 (t, 1H); 6.84 (s, 1H); 6.88 (d, 1H); 7.17 (d, 1H); 7.24 (d, 1H); 7.40-7.47 (m, 3H).

Example 37

Synthesis of 3-[3'-(3-heptyl-1-methylureido)-2-(3,3,3-trifluoropropoxy)biphenyl-4-yl]propanoic acid

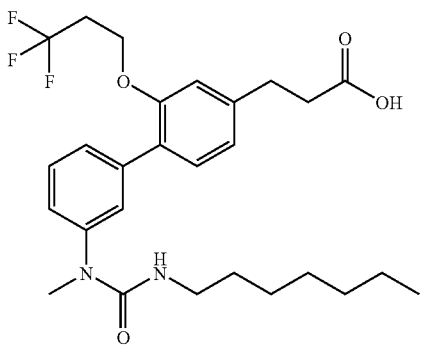

a. Preparation of methyl 3-[3'-(3-heptyl-1-methylureido)-2-(3,3,3-trifluoropropoxy)biphenyl-4-yl]propanoate In a manner similar to that of Example (25a), by reaction of 1.0 mL (8.52 mmol, 7.3 eq) 1-iodo-3,3,3-trifluoropropane and 500 mg (1.17 mmol, 1 eq) of methyl 3-[3'-(3-heptyl-1-methylureido)-2-hydroxybiphenyl-4-yl]propanoate (prepared in Example 15f) in 10 ml of methyl ethyl ketone in the presence of 500 mg (3.61 mmol, 3 eq) of potassium carbonate at 80° C. for 7 days, 50 mg of methyl 3-[3'-(3-heptyl-1-methylureido)-2-(3,3,3-trifluoropropoxy)biphenyl-4-yl]propanoate are obtained in oil form. Yield=8% b. Synthesis of 3-[3'-(3-heptyl-1-methylureido)-2-(3,3,3-trifluoropropoxy)biphenyl-4-yl]propanoic acid In a manner similar to that of Example (19g), by reaction of 50 mg (1.25 mmol, 13 eq) of sodium hydroxide and 50 mg (0.096 mmol, 1 eq) of methyl 3-[3'-(3-heptyl-1-methylureido)-2-(3,3,3-trifluoropropoxy)biphenyl-4-yl]propanoate in 3 ml of a tetrahydrofuran/methanol mixture (8/2) at room temperature for 2 hours, and after crystallization from pentane/isopropyl ether, 14 mg of 3-[3'-(3-heptyl-1-methylureido)-2-(3,3,3-trifluoropropoxy)biphenyl-4-yl]propanoic acid are obtained in the form of a white powder (m.p.=90° C.). Yield=29%

$^1$H NMR (CDCl$_3$, 400 MHz): 0.84 (t, 3H); 1.21-1.32 (m, 8H); 1.40 (m, 2H); 2.53 (m, 2H); 2.68 (t, 2H); 2.99 (t, 2H); 3.15 (q, 2H); 3.28 (s, 3H); 4.19 (t, 2H); 4.36 (t, 1H); 6.82 (s, 1H); 6.92 (d, 1H); 7.17 (m, 1H); 7.25 (m, 1H); 7.26-7.42 (m, 3H).

Example 38

Synthesis of 3-[3'-(3-heptyl-1-methylureido)-2-(4,4,4-trifluorobutoxy)biphenyl-4-yl]propanoic acid

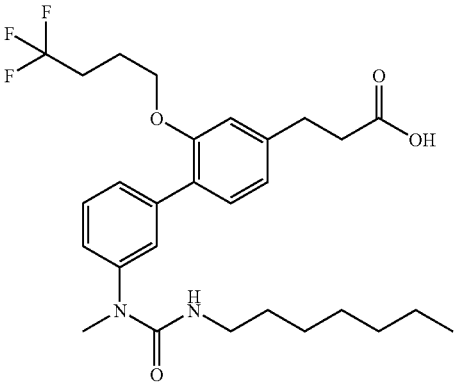

a. Preparation of methyl 3-[3'-(3-heptyl-1-methylureido)-2-(4,4,4-trifluorobutoxy)biphenyl-4-yl]propanoate In a manner similar to that of Example (25a), by reaction of 500 μL (3.78 mmol, 5.8 eq) of 1-iodo-4,4,4-trifluorobutane and 280 mg (0.65 mmol, 1 eq) of methyl 3-[3'-(3-heptyl-1-methylureido)-2-hydroxybiphenyl-4-yl]propanoate (prepared in Example 15f) in 10 ml of methyl ethyl ketone in the presence of 500 mg (3.61 mmol, 5.5 eq) of potassium carbonate at 80° C. for 12 hours, methyl 3-[3'-(3-heptyl-1-methylureido)-2-(4,4,4-trifluorobutoxy)biphenyl-4-yl]propanoate is obtained in oil form and is used in the following reaction without further purification.

b. Synthesis of 3-[3'-(3-heptyl-1-methylureido)-2-(4,4,4-trifluorobutoxy)biphenyl-4-yl]propanoic acid In a manner similar to that of Example (19g), by reaction of 400 mg (10.0 mmol, 4.8 eq) of sodium hydroxide and methyl 3-[3'-(3-heptyl-1-methylureido)-2-(4,4,4-trifluorobutoxy)biphenyl-4-yl]propanoate, obtained in the preceding step, in 10 ml of a tetrahydrofuran/methanol mixture (8/2), and after crystallization from pentane, 252 mg of 3-[3'-(3-heptyl-1-methylureido)-2-(4,4,4-trifluorobutoxy)biphenyl-4-yl]propanoic acid are obtained in the form of a white powder (m.p.=78° C.). Yield=74% over the two steps $^1$H NMR (CDCl$_3$, 400 MHz): 0.84 (t, 3H); 1.21-1.27 (m, 8H); 1.39 (m, 2H); 1.95-2.0 (m, 2H); 2.12-2.17 (m, 2H); 2.73 (t, 2H); 3.00 (t, 2H); 3.15 (q, 2H); 3.29 (s, 3H); 4.02 (t, 2H); 4.39 (t, 1H); 6.83 (s, 1H); 6.93 (d, 1H); 7.18 (m, 1H); 7.24 (d, 1H); 7.38 (s, 1H); 7.43 (d, 2H).

Example 39

Synthesis of 3-[3'-(3-heptyl-1-methylureido)-2-(3-hydroxypropoxy)biphenyl-4-yl]propanoic acid

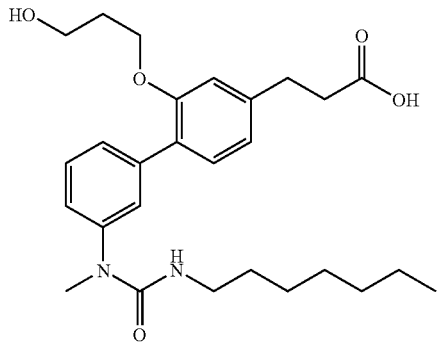

a. Preparation of methyl 3-[3'-(3-heptyl-1-methylureido)-2-(3-hydroxypropoxy)biphenyl-4-yl]propanoate In a manner similar to that of Example (25a), by reaction of 500 μL (5.2 mmol, 7.4 eq) of 3-iodo-1-propanol and 300 mg (0.7 mmol, 1 eq) of methyl 3-[3'-(3-heptyl-1-methylureido)-2-hydroxybiphenyl-4-yl]propanoate (prepared in Example 15f) in 10 ml of methyl ethyl ketone in the presence of 500 mg (3.61 mmol, 5.1 eq) of potassium carbonate at 80° C. for 15 hours, 270 mg of methyl 3-[3'-(3-heptyl-1-methylureido)-2-(3-hydroxypropoxy)biphenyl-4-yl]propanoate are obtained in oil form. Yield=79% b. Synthesis of 3-[3'-(3-heptyl-1-methylureido)-2-(3-hydroxypropoxy)biphenyl-4-yl]propanoic acid In a manner similar to that of Example (19g), by reaction of 400 mg (10.0 mmol, 18 eq) of sodium hydroxide and 270 mg (0.55 mmol, 1 eq) of methyl 3-[3'-(3-heptyl-1-methylureido)-2-(3-hydroxypropoxy)biphenyl-4-yl]propanoate in 3 ml of a tetrahydrofuran/methanol mixture (8/2), and after crystallization from ethyl acetate/heptane, 135 mg of 3-[3'-(3-heptyl-1-methylureido)-2-(3-hydroxypropoxy)biphenyl-4-yl]propanoic acid are obtained in the form of a white powder (m.p.=107° C.). Yield=51%

$^1$H NMR (CDCl$_3$, 400 MHz): 0.84 (t, 3H); 1.22-1.27 (m, 8H); 1.40 (m, 2H); 1.92-1.98 (m, 2H); 2.73 (t, 2H); 3.00 (t, 2H); 3.15 (q, 2H); 3.26 (s, 3H); 3.67 (t, 2H); 4.15 (t, 2H); 4.76 (t, 1H); 6.87 (s, 1H); 6.92 (d, 1H); 7.18-7.22 (m, 2H); 7.35 (d, 2H); 7.43 (t, 1H).

Example 40

Synthesis of 3-[3'-(3-heptyl-1-methylureido)-2-(4-hydroxybutoxy)biphenyl-4-yl]propanoic acid

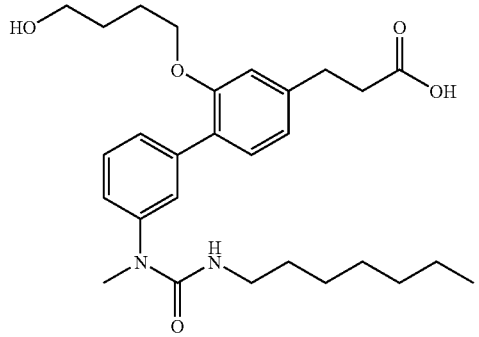

a. Preparation of methyl 3-[3'-(3-Heptyl-1-methylureido)-2-(4-hydroxybutoxy)biphenyl-4-yl]propanoate In a manner similar to that of Example (25a), by reaction of 500 μL (3.45 mmol, 4.9 eq) of 4-bromobutyl acetate and 300 mg (0.7 mmol, 1 eq) of methyl 3-[3'-(3-heptyl-1-methylureido)-2-hydroxybiphenyl-4-yl]propanoate (prepared in Example 15f) in 6 ml of methyl ethyl ketone in the presence of 500 mg (3.61 mmol, 5.1 eq) of potassium carbonate at 80° C. for 15 hours, 305 mg of methyl 3-[3'-(3-heptyl-1-methylureido)-2-(4-hydroxybutoxy)biphenyl-4-yl]propanoate are obtained in oil form. Yield=80% b. Synthesis of 3-[3'-(3-heptyl-1-methylureido)-2-(4-hydroxybutoxy)biphenyl-4-yl]propanoic acid In a manner similar to that of Example (19g), by reaction of 300 mg (7.5 mmol, 13 eq) of sodium hydroxide and 305 mg (0.56 mmol, 1 eq) of methyl 3-[3'-(3-heptyl-1-methylureido)-2-(4-hydroxybutoxy)biphenyl-4-yl]propanoate in 3 ml of a tetrahydrofuran/methanol mixture (8/2), 156 mg of 3-[3'-(3-heptyl-1-methylureido)-2-(4-hydroxybutoxy)biphenyl-4-yl]propanoic acid are obtained in the form of a whitish oil. Yield=57%

$^1$H NMR (CDCl$_3$, 400 MHz): 0.84 (t, 3H); 1.21-1.27 (m, 8H); 1.38-1.41 (m, 2H); 1.63-1.68 (m, 2H); 1.78-1.83 (m, 2H); 2.71 (t, 2H); 2.99 (t, 2H); 3.14 (q, 2H); 3.28 (s, 3H); 3.57 (t, 2H); 4.03 (t, 2H); 4.63 (t, 1H); 6.86 (s, 1H); 6.88 (d, 1H); 7.17 (m, 1H); 7.24 (d, 1H); 7.42-7.46 (m, 3H).

Example 41

Synthesis of 3-[2-butoxy-3'-(1-methyl-3-pentylureido)biphenyl-4-yl]propanoic acid

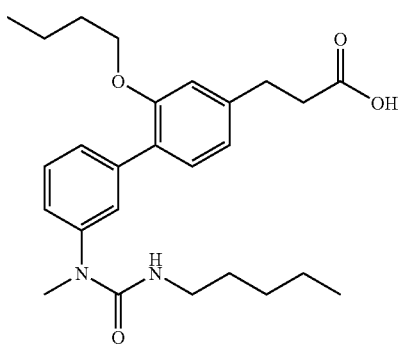

a. Preparation of methyl (E)-3-(2-benzyloxy-3'-methylaminobiphenyl-4-yl)acrylate In a manner similar to that of Example (15e), by reaction of 130 mg (5 mol %) of palladium acetate, 406 mg (10 mol %) of dicyclohexylbiphenyl phosphine, 4.6 g (11.7 mmol, 1.0 eq) of methyl (E)-3-(3-benzyloxy-4-iodophenyl)acrylate (prepared in Example 15d) and 3.26 g (14.0 mmol, 1.2 eq) of methyl[3-(4,4,5,5-tetramethyl[1,3,2]dioxaborolan-2-yl)phenyl]amine (prepared in Example 7a) in 20 mL of a mixture of dimethylformamide/2M potassium phosphate solution (6/1), 4.3 g of methyl (E)-3-(2-benzyloxy-3'-methylaminobiphenyl-4-yl)acrylate are obtained in oil form. Yield=98% b. Preparation of methyl (E)-3-[2-benzyloxy-3'-(1-methyl-3-pentylureido)biphenyl-4-yl]acrylate In a manner similar to that of Example (1d), by reaction of 600 μL (4.6 mmol, 3.5 eq) of pentyl isocyanate and 500 mg (1.33 mmol, 1 eq) of methyl (E)-3-(2-benzyloxy-3'-methylaminobiphenyl-4-yl)acrylate, 544 mg of methyl (E)-3-[2-benzyloxy-3'-(1-methyl-3-pentylureido)biphenyl-4-yl]acrylate are obtained in oil form. Yield=84% c. Preparation of methyl 3-[2-hydroxy-3'-(1-methyl-3-pentylureido)biphenyl-4-yl]propanoate In a manner similar to that of Example (18e), by reaction of 100 mg (18% by mass) of 10% palladium-on-charcoal and 544 mg (1.12 mmol, 1 eq) of methyl (E)-3-[2-benzyloxy-3'-(1-methyl-3-pentylureido)biphenyl-4-yl]acrylate in 10 ml of methanol, 530 mg of methyl 3-[2-hydroxy-3'-(1-methyl-3-pentylureido)biphenyl-4-yl]propanoate are obtained in oil form. Yield=97% d. Preparation of methyl 3-[2-butoxy-3'-(1-methyl-3-pentylureido)biphenyl-4-yl]propanoate In a manner similar to that of Example (25a), by reaction of 500 μL (4.4 mmol, 3.3 eq) of 1-iodobutane and 530 mg (1.33 mmol, 1 eq) of methyl 3-[2-hydroxy-3'-(1-methyl-3-pentylureido)biphenyl-4-yl]propanoate in 10 ml of methyl ethyl ketone in the presence of 500 mg (3.61 mmol, 2.7 eq) of potassium carbonate at 80° C. for 16 hours, methyl 3-[2-butoxy-3'-(1-methyl-3-pentylureido)biphenyl-4-yl]propanoate is obtained in oil form and is used in the following reaction without further purification.

e. Synthesis of 3-[2-butoxy-3'-(1-methyl-3-pentylureido)biphenyl-4-yl]propanoic acid In a manner similar to that of Example (25a), by reaction of 400 mg (10 mmol, 7.5 eq) of sodium hydroxide and methyl 3-[2-butoxy-3'-(1-methyl-3-pentylureido)biphenyl-4-yl]propanoate, obtained in the preceding step, in 6 ml of a tetrahydrofuran/methanol mixture (8/2), and after crystallization from pentane, 220 mg of 3-[2-butoxy-3'-(1-methyl-3-pentylureido)biphenyl-4-yl]propanoic acid are obtained in the form of a white powder (m.p.=78° C.). Yield=46% over the two steps.

$^1$H NMR (CDCl$_3$, 400 MHz): 0.84 (t, 3H); 0.91 (t, 3H); 1.18-1.27 (m, 4H); 1.36-1.44 (m, 4H); 1.68-1.72 (m, 2H); 2.73 (t, 2H); 3.00 (t, 2H); 3.15 (q, 2H); 3.29 (s, 3H); 3.97 (t, 2H); 4.41 (t, 1H); 6.84 (s, 1H); 6.87 (d, 1H); 7.17 (d, 1H); 7.25 (d, 1H); 7.42-7.46 (m, 3H).

Example 42

Synthesis of 3-[2-benzyloxy-3'-(3-heptyl-1-methylureido)biphenyl-4-yl]propanoic acid

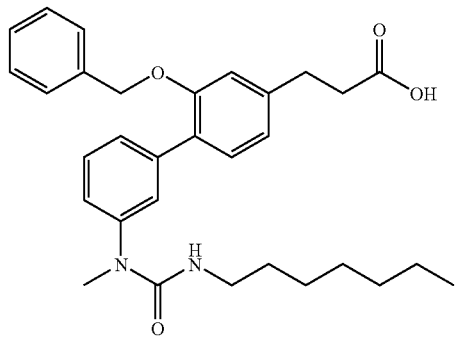

a. Preparation of methyl 3-[2-benzyloxy-3'-(3-heptyl-1-methylureido)biphenyl-4-yl]propanoate In a manner similar to that of Example (25a), by reaction of 300 μL (2.5 mmol, 2.7 eq) of benzyl bromide and 400 mg (0.93 mmol, 1 eq) of methyl 3-[3'-(3-heptyl-1-methylureido)-2-hydroxybiphenyl-4-yl]propanoate (prepared in Example 15f) in 10 ml of methyl ethyl ketone in the presence of 500 mg (3.61 mmol, 3.9 eq) of potassium carbonate at 90° C. for 3 hours, methyl 3-[2-benzyloxy-3'-(3-heptyl-1-methylureido)biphenyl-4-yl]propanoate is obtained in oil form and is used in the following reaction without further purification.

b. Synthesis of 3-[2-benzyloxy-3'-(3-heptyl-1-methylureido)biphenyl-4-yl]propanoic acid In a manner similar to that of Example (19g), by reaction of 400 mg (10 mmol, 10 eq) of sodium hydroxide and methyl 3-[2-benzyloxy-3'-(3-heptyl-1-methylureido)biphenyl-4-yl]propanoate, obtained in the preceding step, in 10 ml of a tetrahydrofuran/methanol mixture (8/2), and after crystallization from pentane, 305 mg of 3-[2-benzyloxy-3'-(3-heptyl-1-methylureido)biphenyl-4-yl]propanoic acid are obtained in the form of a white powder (m.p.=76° C.). Yield=65% over the two steps.

¹H NMR (CDCl₃, 400 MHz): 0.83 (t, 3H); 1.19-1.26 (m, 8H); 1.30-1.35 (m, 2H); 2.72 (t, 2H); 3.00 (t, 2H); 3.05-3.10 (q, 2H); 3.20 (s, 3H); 4.39 (t, 1H); 5.07 (s, 2H); 6.92 (d, 2H); 7.17 (d, 1H); 7.28-7.33 (m, 6H); 7.42-7.47 (m, 3H).

Example 43

Synthesis of 3-[2-(3-fluorobenzyloxy)-3'-(3-heptyl-1-methylureido)biphenyl-4-yl]propanoic acid

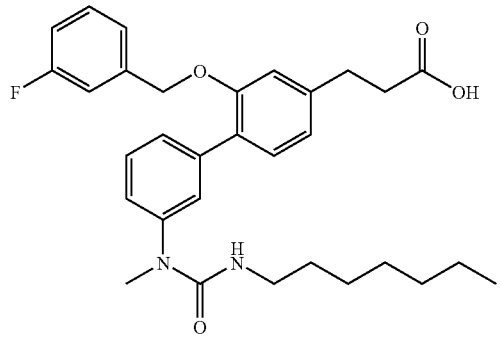

a. Preparation of methyl 3-[2-(3-fluorobenzyloxy)-3'-(3-heptyl-1-methylureido)biphenyl-4-yl]propanoate In a manner similar to that of Example (25a), by reaction of 300 μL (2.4 mmol, 2.6 eq) of 3-fluorobenzyl bromide and 400 mg (0.93 mmol, 1 eq) of methyl 3-[3'-(3-heptyl-1-methylureido)-2-hydroxybiphenyl-4-yl]propanoate (prepared in Example 15f) in 10 ml of methyl ethyl ketone in the presence of 500 mg (3.61 mmol, 3.9 eq) of potassium carbonate at 90° C. for 3 hours, methyl 3-[2-(3-fluorobenzyloxy)-3'-(3-heptyl-1-methylureido)biphenyl-4-yl]propanoate is obtained in oil form and is used in the following reaction without further purification.

b. Synthesis of 3-[2-(3-fluorobenzyloxy)-3'-(3-heptyl-1-methylureido)biphenyl-4-yl]propanoic acid In a manner similar to that of Example 19g, by reaction of 400 mg (10 mmol, 10 eq) of sodium hydroxide and methyl 3-[2-(3-fluorobenzyloxy)-3'-(3-heptyl-1-methylureido)biphenyl-4-yl]propanoate, obtained in the preceding step, in 10 ml of a tetrahydrofuran/methanol mixture (8/2), and after crystallization from pentane, 305 mg of 3-[2-(3-fluorobenzyloxy)-3'-(3-heptyl-1-methylureido)biphenyl-4-yl]propanoic acid are obtained in the form of a white powder (m.p.=73° C.). Yield=68% over the two steps.

¹H NMR (CDCl₃, 400 MHz): 0.83 (t, 3H); 1.19-1.26 (m, 8H); 1.31-1.36 (m, 2H); 2.72 (t, 2H); 3.00 (t, 2H); 3.07-3.12 (q, 2H); 3.23 (s, 3H); 4.40 (t, 1H); 5.06 (s, 2H); 6.90 (s, 1H); 6.93-7.00 (m, 3H); 7.08 (d, 1H); 7.18 (d, 1H); 7.28 (m, 2H); 7.44-7.46 (m, 3H).

Example 44

Synthesis of 3-[2-(4-fluorobenzyloxy)-3'-(3-heptyl-1-methylureido)biphenyl-4-yl]propanoic acid

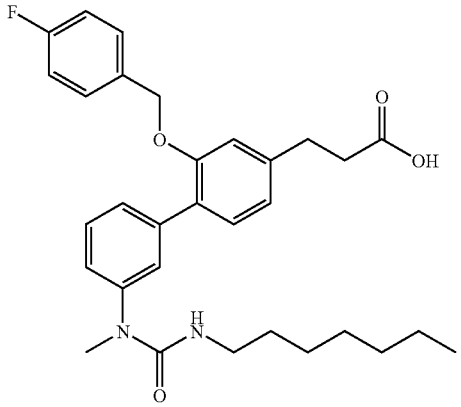

a. Preparation of methyl 3-[2-(4-fluorobenzyloxy)-3'-(3-heptyl-1-methylureido)biphenyl-4-yl]propanoate In a manner similar to that of Example (25a), by reaction of 300 μL (2.4 mmol, 2.6 eq) of 3-fluorobenzyl bromide and 400 mg (0.93 mmol, 1 eq) of methyl 3-[3'-(3-heptyl-1-methylureido)-2-hydroxybiphenyl-4-yl]propanoate (prepared in Example 15f) in 10 ml of methyl ethyl ketone in the presence of 500 mg (3.61 mmol, 3.9 eq) of potassium carbonate at 90° C. for 3 hours, methyl 3-[2-(4-fluorobenzyloxy)-3'-(3-heptyl-1-methylureido)biphenyl-4-yl]propanoate is obtained in oil form and is used in the following reaction without further purification.

b. Synthesis of 3-[2-(4-fluorobenzyloxy)-3'-(3-heptyl-1-methylureido)biphenyl-4-yl]propanoic acid In a manner similar to that of Example (19g), by reaction of 400 mg (10 mmol, 10 eq) of sodium hydroxide and methyl 3-[2-(4-fluorobenzyloxy)-3'-(3-heptyl-1-methylureido)biphenyl-4-yl]propanoate, obtained in the preceding step, in 10 ml of a tetrahydrofuran/methanol mixture (8/2), and after crystallization from pentane, 310 mg of 3-[2-(4-fluorobenzyloxy)-3'-(3-heptyl-1-methylureido)biphenyl-4-yl]propanoic acid are obtained in the form of a white powder (m.p.=79° C.). Yield=64% over the two steps.

¹H NMR (CDCl₃, 400 MHz): 0.83 (t, 3H); 1.19-1.26 (m, 8H); 1.32-1.36 (m, 2H); 2.73 (t, 2H); 3.00 (t, 2H); 3.07-3.12 (q, 2H); 3.21 (s, 3H); 4.38 (t, 1H); 5.03 (s, 2H); 6.92 (d, 2H); 6.99-7.03 (m, 2H); 7.17 (d, 1H); 7.27-7.29 (m, 3H); 7.42-7.45 (m, 3H).

Example 45

Synthesis of 3-[3'-(3-heptyl-1-methylureido)-2-pentyloxybiphenyl-4-yl]propanoic acid

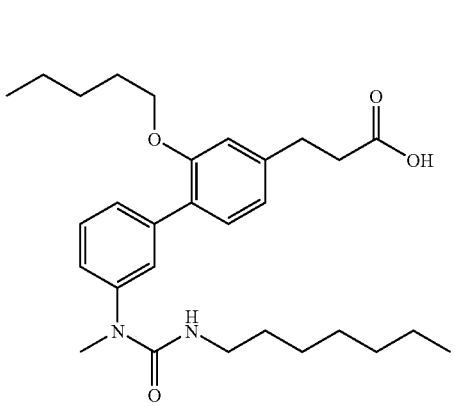

a. Preparation of methyl 3-[3'-(3-heptyl-1-methylureido)-2-pentyloxybiphenyl-4-yl]propanoate In a manner similar to that of Example (25a), by reaction of 500 µL (3.8 mmol, 5.4 eq) of 1-iodopentane and 300 mg (0.7 mmol, 1 eq) of methyl 3-[3'-(3-heptyl-1-methylureido)-2-hydroxybiphenyl-4-yl]propanoate (prepared in Example 15f) in 10 ml of methyl ethyl ketone in the presence of 500 mg (3.61 mmol, 5.1 eq) of potassium carbonate at 80° C. for 12 hours, methyl 3-[3'-(3-heptyl-1-methylureido)-2-pentyloxybiphenyl-4-yl]propanoate is obtained in oil form and is used in the following reaction without further purification.

b. Synthesis of 3-[3'-(3-heptyl-1-methylureido)-2-pentyloxybiphenyl-4-yl]propanoic acid In a manner similar to that of Example (19g), by reaction of 400 mg (10 mmol, 14 eq) of sodium hydroxide and methyl 3-[3'-(3-heptyl-1-methylureido)-2-pentyloxybiphenyl-4-yl]propanoate, obtained in the preceding step, in 10 ml of a tetrahydrofuran/methanol mixture (8/2), and after crystallization from pentane, 260 mg of 3-[3'-(3-heptyl-1-methylureido)-2-pentyloxybiphenyl-4-yl]propanoic acid are obtained in the form of a white powder (m.p.=69° C.). Yield=77% over the two steps.

$^1$H NMR (CDCl$_3$, 400 MHz): 0.84 (t, 3H); 0.88 (t, 3H); 1.21-1.25 (m, 8H); 1.32-1.40 (m, 6H); 1.72 (m, 2H); 2.73 (t, 2H); 3.00 (t, 2H); 3.15 (q, 2H); 3.29 (s, 3H); 3.96 (t, 2H); 4.42 (t, 1H); 6.84 (s, 1H); 6.87 (d, 1H); 7.17 (d, 1H); 7.24 (d, 1H); 7.40-7.46 (m, 3H).

Example 46

Synthesis of 3-[3'-(1-methyl-3-pentylureido)-2-pentyloxybiphenyl-4-yl]propanoic acid

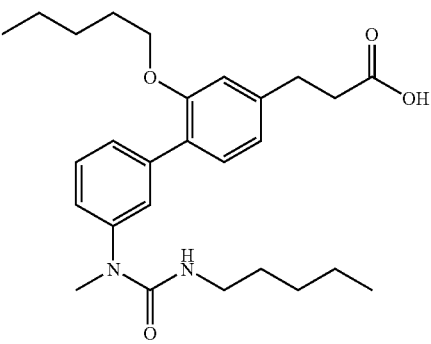

a. Preparation of 1-(3-bromophenyl)-1-methyl-3-pentylurea

A solution of 50.0 g (0.442 mol, 1 eq) of pentyl isocyanate in 50 mL of dichloromethane is added to a mixture of 82.2 g (0.442 mol, 1 eq) of (3-bromophenyl)methylamine in 250 mL of dichloromethane in the presence of 20 mL (0.143 mol, 0.3 eq) of triethylamine. The reaction medium is refluxed for 3 days and then hydrolyzed in 200 mL of 1N hydrochloric acid solution and extracted with ethyl acetate. The organic phases are combined, washed with water and sodium chloride, and evaporated. 123 g of 1-(3-bromophenyl)-1-methyl-3-pentylurea are obtained. Yield=93% b. Preparation of 3-(1-methyl-3-pentylureido)phenylboronic acid

In a manner similar to that of Example (18a), by reaction of 123 g (0.411 mol, 1 eq) of 1-(3-bromophenyl)-1-methyl-3-pentylurea in 1.23 L of tetrahydrofuran, 150 mL (0.452 mol, 1.1 eq) of methyllithium, 530 mL (0.904 mol, 2.2 eq) of a 1.7 M solution of tert-butyllithium in pentane and 115 mL (0.904 mol, 2.2 eq) of trimethyl borate, and after purification by chromatography on silica gel (50/50 heptane/ethyl acetate) and crystallization from ethyl acetate/heptane, 42.0 g of 3-(1-methyl-3-pentylureido)phenylboronic acid are obtained in the form of a pink-colored powder. Yield=39% c. Preparation of methyl (E)-3-[2-benzyloxy-3'-(1-methyl-3-pentylureido)biphenyl-4-yl]acrylate In a manner similar to that of Example (18d), by reaction of 17 mg (2 mol %) of palladium acetate, 53 mg (4 mol %) of dicyclohexylbiphenyl phosphine, 1.5 g (3.8 mmol, 1.0 eq) of methyl (E)-3-(3-benzyloxy-4-iodophenyl)acrylate (prepared in Example 24d) and 1.3 g (4.94 mmol, 1.3 eq) of 3-(1-methyl-3-pentylureido)phenylboronic acid in 20 mL of a mixture of dimethylformamide/2M potassium phosphate solution (6/1), 1.54 g of methyl (E)-3-[2-benzyloxy-3'-(1-methyl-3-pentylureido)biphenyl-4-yl]acrylate are obtained in oil form. Yield=83% d. Preparation of methyl 3-[2-hydroxy-3'-(1-methyl-3-pentylureido)biphenyl-4-yl]propanoate In a manner similar to that of Example (18e), by reaction of 400 mg (26% by mass) of 10% palladium-on-charcoal, 1.54 g (3.16 mmol, 1 eq) of methyl (E)-3-[2-benzyloxy-3'-(1-methyl-3-pentylureido)biphenyl-4-yl]acrylate in 20 ml of methanol and 5 mL of ethyl acetate, and after crystallization from pentane, 1.1 g of methyl 3-[2-hydroxy-3'-(1-methyl-3-pentylureido)biphenyl-4-yl]propanoate are obtained in solid form. Yield=87% e. Preparation of methyl 3-[3'-(1-methyl-3-pentylureido)-2-pentyloxybiphenyl-4-yl]propanoate In a manner similar to that of Example (25a), by reaction of 500 μL (3.8 mmol, 3.8 eq) of 1-iodopentane and 400 mg (1.0 mmol, 1 eq) of methyl 3-[2-hydroxy-3'-(1-methyl-3-pentylureido)biphenyl-4-yl]propanoate in 10 ml of methyl ethyl ketone in the presence of 500 mg (3.61 mmol, 3.6 eq) of potassium carbonate at 80° C. for 12 hours, methyl 3-[3'-(1-methyl-3-pentylureido)-2-pentyloxybiphenyl-4-yl]propanoate is obtained in oil form and is used in the following reaction without further purification.

f. Synthesis of 3-[3'-(1-methyl-3-pentylureido)-2-pentyloxybiphenyl-4-yl]propanoic acid In a manner similar to that of Example (19g), by reaction of 400 mg (10 mmol, 10 eq) of sodium hydroxide and methyl 3-[3'-(1-methyl-3-pentylureido)-2-pentyloxybiphenyl-4-yl]propanoate, obtained in the preceding step, in 10 ml of a tetrahydrofuran/methanol mixture (8/2), and after crystallization from pentane, 312 mg of 3-[3'-(1-methyl-3-pentylureido)-2-pentyloxybiphenyl-4-yl]propanoic acid are obtained in the form of a white powder (m.p.=83° C.). Yield=74% over the two steps.
$^1$H NMR (CDCl$_3$, 400 MHz): 0.83 (t, 3H); 0.88 (t, 3H); 1.19-1.40 (m, 10H); 1.72 (m, 2H); 2.73 (t, 2H); 3.00 (t, 2H); 3.15 (q, 2H); 3.29 (s, 3H); 3.96 (t, 2H); 4.43 (t, 1H); 6.84 (s, 1H); 6.88 (d, 1H); 7.16 (d, 1H); 7.24 (d, 1H); 7.42-7.47 (m, 3H).

Example 47

Synthesis of 3-[2-(2-ethoxyethoxy)-3'-(3-heptyl-1-methylureido)biphenyl-4-yl]propanoic acid

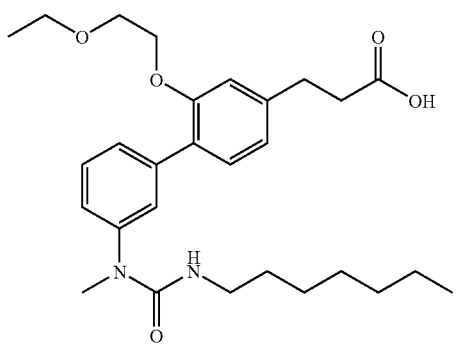

a. Preparation of methyl 3-[2-(2-ethoxyethoxy)-3'-(3-heptyl-1-methylureido)biphenyl-4-yl]propanoate In a manner similar to that of Example (25a), by reaction of 500 μL (4.43 mmol, 5.4 eq) of 2-bromoethyl ethyl ether and 350 mg (0.82 mmol, 1 eq) of methyl 3-[3'-(3-heptyl-1-methylureido)-2-hydroxybiphenyl-4-yl]propanoate (prepared in Example 15f) in 10 ml of methyl ethyl ketone in the presence of 500 mg (3.61 mmol, 4.4 eq) of potassium carbonate at 90° C. for 12 hours, methyl 3-[2-(2-ethoxyethoxy)-3'-(3-heptyl-1-methylureido)biphenyl-4-yl]propanoate is obtained in oil form and is used in the following reaction without further purification.

b. Synthesis of 3-[2-(2-ethoxyethoxy)-3'-(3-heptyl-1-methylureido)biphenyl-4-yl]propanoic acid In a manner similar to that of Example (19g), by reaction of 400 mg (10 mmol, 14 eq) of sodium hydroxide and methyl 3-[2-(2-ethoxyethoxy)-3'-(3-heptyl-1-methylureido)biphenyl-4-yl]propanoate, obtained in the preceding step, in 10 ml of a tetrahydrofuran/methanol mixture (8/2), and after crystallization from pentane and isopropyl ether, 245 mg of 3-[2-(2-ethoxyethoxy)-3'-(3-heptyl-1-methylureido)biphenyl-4-yl]propanoic acid are obtained in the form of a white powder (m.p.=63° C.). Yield=62% over the two steps.
$^1$H NMR (CDCl$_3$, 400 MHz): 0.85 (t, 3H); 1.17 (t, 3H); 1.21-1.27 (m, 8H); 1.40 (m, 2H); 2.73 (t, 2H); 3.01 (t, 2H); 3.16 (q, 2H); 3.29 (s, 3H); 3.46-3.51 (q, 2H); 3.70 (m, 2H); 4.13 (m, 2H); 4.47 (t, 1H); 6.87 (s, 1H); 6.90 (d, 1H); 7.17 (d, 1H); 7.24 (s, 1H); 7.41 (t, 1H); 7.51 (d, 2H).

Example 48

Synthesis of 3-[2-butoxy-3'-(1-methyl-3-phenylureido)biphenyl-4-yl]propanoic acid

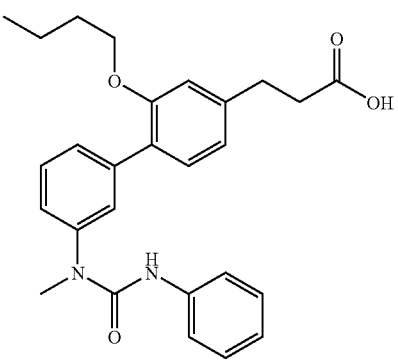

a. Preparation of 3-hydroxy-4-iodobenzoic acid 21.0 g (0.52 mol, 1.05 eq) of sodium hydroxide and then 78.7 g (0.52 mol, 1.05 eq) of sodium iodide are added to a solution of 69.1 g (0.5 mol, 1 eq) of 3-hydroxybenzoic acid in 700 ml of methanol. The reaction mixture is cooled to 0° C. and potassium hypochlorite solution (0.52 mol, 1.05 eq) is then added dropwise. The reaction medium is stirred at 0-5° C. for 2 hours and then at room temperature overnight. The methanol is evaporated off and the reaction medium is then acidified with concentrated hydrochloric acid solution. The precipitated product is filtered off, washed with water and dried. 121 g of 3-hydroxy-4-iodobenzoic acid are obtained in the form of an off-white solid. Yield=92% b. Preparation of methyl 3-hydroxy-4-iodobenzoate 59 ml (1.10 mol, 2.4 eq) of sulfuric acid are added to a solution of 121 g (0.458 mol, 1 eq) of methyl 3-hydroxy-4-iodobenzoic acid in 700 ml of methanol. The reaction mixture is refluxed for 6 days. The methanol is evaporated off and the reaction medium is then poured into water and extracted with ethyl acetate. The organic phases are combined, washed with water and dried over sodium sulfate. The solvent is concentrated and the solid obtained is filtered off and dried. 88.56 g of methyl 3-hydroxy-4-iodobenzoate are obtained in the form of white crystals. Yield=70% c. Preparation of methyl 3-butoxy-4-iodobenzoate

In a manner similar to that of Example (25a), by reaction of 21.5 mL (0.189 mol, 1.5 eq) of 1-iodobutane and 35.03 g (0.126 mol, 1 eq) of methyl 3-hydroxy-4-iodobenzoate in 350 ml of methyl ethyl ketone in the presence of 52.24 g (0.378 mol, 3 eq) of potassium carbonate at 85° C. for 2 hours 30 minutes, and after washing with heptane, 41.78 g of methyl 3-butoxy-4-iodobenzoate are obtained in the form of white crystals. Yield=99% d. Preparation of (3-butoxy-4-iodophenyl)methanol 8.17 g (0.375 mol, 3 eq) of lithium borohydride are added to a solution of 41.78 g (0.125 mol, 1 eq) of methyl 3-butoxy-4-iodobenzoate in 210 ml of tetrahydrofuran. The reaction medium is heated at 60° C. for 2 hours and then hydrolyzed cautiously in ice-cold saturated ammonium chloride solution. The reaction medium is neutralized with concentrated hydrochloric acid and then extracted with ethyl acetate. The organic phases are washed with water and dried over magnesium sulfate. The solvent is evaporated off and 38.31 g of (3-butoxy-4-iodophenyl)methanol are obtained in the form of a whitish oil. Yield=100% e. Preparation of 3-butoxy-4-iodobenzaldehyde 89.5 g (0.875 mol, 7 eq) of manganese dioxide are added to a solution of 38.30 g (0.125 mol, 1 eq) of (3-butoxy-4-iodophenyl)methanol in 250 mL of dichloromethane. The reaction medium is stirred at room temperature for 18 hours and then filtered through silica gel. The solvent is evaporated off and 29.61 g of 3-butoxy-4-iodobenzaldehyde are obtained in the form of an orange oil. Yield=78% f. Preparation of methyl (E)-3-(3-butoxy-4-iodophenyl)acrylate 65.08 g (0.195 mol, 2 eq) of methyl triphenylphosphoranylideneacetate are added to a solution of 29.60 g (0.097 mol, 1 eq) of methyl-3-butoxy-4-iodobenzaldehyde in 360 ml of toluene. The reaction mixture is refluxed for 2 hours. The solvent is evaporated off and the oil obtained is chromatographed on silica gel (50/50 heptane/dichloromethane). 30.47 g of methyl (E)-3-(3-butoxy-4-iodophenyl)acrylate are obtained in the form of pale yellow crystals. Yield=87% g. Preparation of methyl (E)-3-(2-Butoxy-3'-methylaminobiphenyl-4-yl)acrylate In a manner similar to that of Example (18d), by reaction of 28 mg (1 mol %) of palladium acetate, 88 mg (2 mol %) of dicyclohexylbiphenylphosphine, 4.5 g (12.5 mmol, 1.0 eq) of methyl (E)-3-(3-butoxy-4-iodophenyl)acrylate and 3.79 g (16.2 mmol, 1.3 eq) of methyl[3-(4,4,5,5-tetramethyl[1,3,2]dioxaborolan-2-yl)phenyl]amine (prepared in Example 7a) in 72 mL of a mixture of dimethylformamide/2M potassium phosphate solution (5/1) at 90° C. for 2 hours, 3.67 g of methyl (E)-3-(2-butoxy-3'-methylaminobiphenyl-4-yl)acrylate are obtained in the form of crystals. Yield=86% h. Preparation of methyl 3-(2-butoxy-3'-methylaminobiphenyl-4-yl)propanoate

A solution of 3.63 g (10.7 mmol) of methyl (E)-3-(2-butoxy-3'-methylaminobiphenyl-4-yl)acrylate in 70 ml of methanol is stirred for 4 hours at room temperature in the presence of 363 mg (10% by mass) of 10% palladium-on-charcoal under a hydrogen atmosphere. The palladium is filtered off and the solvent is evaporated off. 3.39 g of methyl 3-(2-butoxy-3'-methylaminobiphenyl-4-yl)propanoate are obtained in the form of a yellowish oil. Yield=93% i. Preparation of methyl 3-[2-butoxy-3'-(1-methyl-3-phenylureido)biphenyl-4-yl]propanoate In a manner similar to that of Example (1d), by reaction of 165 μl (1.5 mmol, 1.5 eq) of phenyl isocyanate and 342 mg (1.0 mmol, 1 eq) of methyl 3-(2-butoxy-3'-methylaminobiphenyl-4-yl)propanoate, 437 mg of methyl 3-[2-butoxy-3'-(1-methyl-3-phenylureido)biphenyl-4-yl]propanoate are obtained in the form of a yellow paste. Yield=95% j. Synthesis of 3-[2-butoxy-3'-(1-methyl-3-phenylureido)biphenyl-4-yl]propanoic acid In a manner similar to that of Example (19g), by reaction of 187 mg (4.7 mmol, 5 eq) of sodium hydroxide and 437 mg (0.93 mmol, 1 eq) of methyl 3-[2-butoxy-3'-(1-methyl-3-phenylureido)biphenyl-4-yl]propanoate in 5 ml of methanol, 305 mg of 3-[2-butoxy-3'-(1-methyl-3-phenylureido)biphenyl-4-yl]propanoic acid are obtained in the form of white crystals (m.p.=134-136° C.). Yield=73%

$^1$H NMR (CDCl$_3$, 400 MHz): 0.84 (t, 3H); 1.33-1.39 (m, 2H); 1.62-1.67 (m, 2H); 2.73 (t, 2H); 2.99 (t, 2H); 3.37 (s, 3H); 3.95 (t, 2H); 6.34 (s, 1H); 6.84 (s, 1H); 6.85 (d, 1H); 6.98 (t, 1H); 7.2-7.3 (m, 5H); 7.50 (m, 2H); 7.57 (s, 1H).

Example 49

Synthesis of 3-[2-(2-ethoxyethoxy)-3'-(1-methyl-3-pentylureido)biphenyl-4-yl]propanoic acid

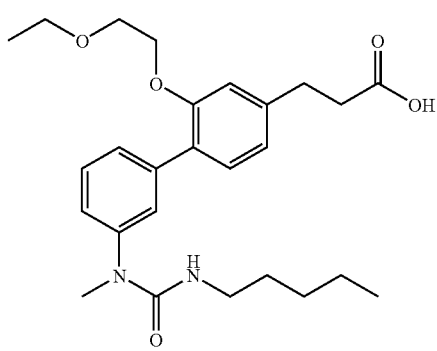

a. Preparation of methyl 3-[2-(2-ethoxyethoxy)-3'-(1-methyl-3-pentylureido)biphenyl-4-yl]propanoate In a manner similar to that of Example (25a), by reaction of 230 mg (1 mmol, 1.5 eq) of 2-bromoethyl ethyl ether and 400 mg (1.0 mmol, 1 eq) of methyl 3-[2-hydroxy-3'-(1-methyl-3-pentylureido)biphenyl-4-yl]propanoate (prepared as in Example 46d) in 10 ml of methyl ethyl ketone in the presence of 415 mg (3.0 mmol, 3 eq) of potassium carbonate and 60 mg (0.4 mmol, 0.4 eq) of sodium iodide at 90° C. for 48 hours, 450 mg of methyl 3-[2-(2-ethoxyethoxy)-3'-(1-methyl-3-pentylureido)biphenyl-4-yl]propanoate are obtained in the form of a yellow oil. Yield=96% b. Synthesis of 3-[2-(2-ethoxyethoxy)-3'-(1-methyl-3-pentylureido)biphenyl-4-yl]propanoic acid In a manner similar to that of Example (19g), by reaction of 181 mg (4.5 mmol, 5 eq) of sodium hydroxide and 427 mg (0.90 mmol, 1 eq) of methyl 3-[2-(2-ethoxyethoxy)-3'-(1-methyl-3-pentylureido)biphenyl-4-yl]propanoate in 5 ml of methanol, 304 mg of 3-[2-(2-ethoxyethoxy)-3'-(1-methyl-3-pentylureido)biphenyl-4-yl]propanoic acid are obtained in the form of a white powder (m.p.=61-62° C.). Yield=73%
$^1$H NMR (CDCl$_3$, 400 MHz): 0.84 (t, 3H); 1.15 (t, 3H); 1.20-1.27 (m, 4H); 1.37-1.42 (m, 2H); 2.72 (t, 2H); 2.99 (t, 2H); 3.46-3.51 (q, 2H); 3.70 (t, 2H); 4.13 (t, 2H); 4.49 (t, 1H); 6.87 (s, 1H); 6.90 (d, 1H); 7.15 (d, 1H); 7.17 (s, 1H); 7.41 (t, 3H); 7.50 (s, 1H); 7.51 (d, 1H).

Example 50

Synthesis of 3-[2-(2-diethylaminoethoxy)-3'-(3-heptyl-1-methylureido)biphenyl-4-yl]propanoic acid hydrochloride

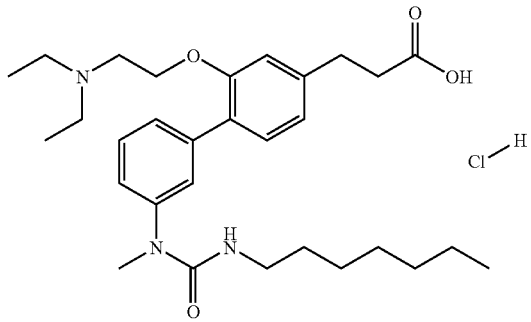

a. Preparation of methyl 3-[2-(2-diethylaminoethoxy)-3'-(3-heptyl-1-methylureido)biphenyl-4-yl]propanoate A solution of 500 mg (1.17 mmol, 1 eq) of methyl 3-[3'-(3-heptyl-1-methylureido)-2-hydroxybiphenyl-4-yl]propanoate (prepared in Example 15f) in 5 ml of tetrahydrofuran in the presence of 150 mg (1.29 mmol, 1.1 eq) of 2-diethylaminoethanol, 460 mg (1.76 mmol, 1.5 eq) of triphenylphosphine and 280 µL (1.76 mmol, 1.5 eq) of diethyl azodicarboxylate (DEAD) is stirred at room temperature for 24 hours. The reaction medium is concentrated and the residue is then chromatographed on silica gel (40/60 heptane/ethyl acetate). 490 mg of methyl 3-[2-(2-diethylaminoethoxy)-3'-(3-heptyl-1-methylureido)biphenyl-4-yl]propanoate are obtained. Yield=80% b. Synthesis of 3-[2-(2-diethylaminoethoxy)-3'-(3-heptyl-1-methylureido)biphenyl-4-yl]propanoic acid hydrochloride 220 mg (9.3 mmol, 10 eq) of lithium hydroxide are added to a solution of 490 mg (0.93 mmol) of methyl 3-[2-(2-diethylaminoethoxy)-3'-(3-heptyl-1-methylureido)biphenyl-4-yl]propanoate in 7 ml of 5/1/1 tetrahydrofuran/methanol/water. The reaction mixture is stirred for 4 hours at room temperature. The reaction medium is hydrolyzed with water and extracted with ethyl acetate. The organic phases are combined, washed with water and dried over sodium sulfate. The solvents are evaporated off and the residue is then chromatographed on silica gel (90/10 dichloromethane/methanol), purified on a preparative thin-layer silica plate and then placed in hydrochloride form. 14 mg of 3-[2-(2-diethylaminoethoxy)-3'-(3-heptyl-1-methylureido)biphenyl-4-yl]propanoic acid hydrochloride are obtained in the form of a colorless oil. Yield=3%
$^1$H NMR (CDCl$_3$, 400 MHz): 0.77 (t, 3H); 0.93 (t, 3H); 1.16 (m, 8H); 1.32 (m, 2H); 2.48 (t, 2H); 2.63-2.68 (q, 4H); 2.87 (m, 4H); 3.04-3.08 (q, 2H); 3.19 (s, 3H); 4.11 (m, 2H); 4.36 (t, 1H); 6.77 (d, 1H); 6.82 (s, 1H); 7.07 (d, 2H); 7.30 (d, 3H).

Example 51

Synthesis of 3-[3'-(3-heptyl-1-methylureido)-2-(2-morpholin-4-ylethoxy)biphenyl-4-yl]propanoic acid

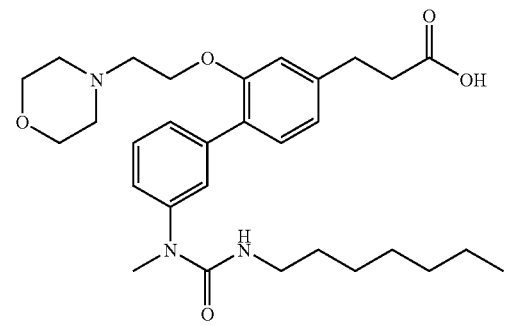

a. Preparation of methyl 3-[3'-(3-Heptyl-1-methylureido)-2-(2-morpholin-4-ylethoxy)biphenyl-4-yl]propanoate In a manner similar to that of Example (50a), by reaction of 500 mg (1.17 mmol, 1 eq) of methyl 3-[3'-(3-heptyl-1-methylureido)-2-hydroxybiphenyl-4-yl]propanoate (prepared in Example 15f) in 5 ml of tetrahydrofuran, 170 mg (1.29 mmol, 1.1 eq) of N-(2-hydroxyethyl)morpholine, 460 mg (1.76 mmol, 1.5 eq) of triphenylphosphine and 280 µL (1.76 mmol, 1.5 eq) of diethyl azodicarboxylate (DEAD), 420 mg of methyl 3-[3'-(3-heptyl-1-methylureido)-2-(2-morpholin-4-ylethoxy)biphenyl-4-yl]propanoate are obtained. Yield=68% b. Synthesis of 3-[3'-(3-heptyl-1-methylureido)-2-(2-morpholin-4-ylethoxy)biphenyl-4-yl]propanoic acid 630 mg (1.56 mmol, 2 eq) of sodium hydroxide are added to a solution of 420 mg (0.78 mmol, 1 eq) of methyl 3-[3'-(3- heptyl-1-methylureido)-2-(2-morpholin-4-ylethoxy)biphenyl-4-yl]propanoate in 8 ml of 8/1/1 tetrahydrofuran/methanol/water. The reaction mixture is stirred for 4 hours at room temperature. The reaction medium is hydrolyzed with water and acetic acid and extracted with ethyl acetate. The organic phases are combined, washed with water and dried over sodium sulfate. The solvents are evaporated off and the residue is then chromatographed on silica gel (40/60 heptane/ethyl acetate) and then on preparative HPLC. 10 mg of 3-[3'-(3-heptyl-1-methylureido)-2-(2-morpholin-4-ylethoxy)biphenyl-4-yl]propanoic acid are obtained in oil form. Yield=2%

$^1$H NMR (CDCl$_3$, 400 MHz): 0.79 (t, 3H); 1.18 (m, 8H); 1.37 (m, 2H); 2.57 (t, 2H); 2.94 (t, 2H); 3.02-3.14 (q, 2H); 3.22 (s, 3H); 3.31 (m, 2H); 3.73 (m, 4H); 4.38 (t, 2H); 4.43 (t, 1H); 6.85 (s, 1H); 6.87 (d, 1H); 7.10-7.17 (m, 2H); 7.24 (d, 1H); 7.33-7.37 (m, 3H).

Example 52

Synthesis of 3-[2-amino-3'-(1-methyl-3-pentylureido)biphenyl-4-yl]propanoic acid

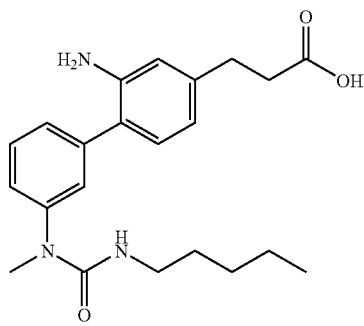

a. Preparation of methyl (E)-3-(4-chloro-3-nitrophenyl)acrylate

A solution of 5.0 g (0.027 mol, 1 eq) of 4-chloro-3-nitrobenzaldehyde in 150 ml of toluene in the presence of 18.0 g (0.054 mol, 2 eq) of triphenylphospharanylidene is refluxed for 1 hour 30 minutes. The cooled reaction medium is hydrolyzed by addition of 100 mL of water and the phases are then separated by settling. The organic phase is dried over sodium sulfate and evaporated. The residue is chromatographed on silica gel (70/30 heptane/ethyl acetate) and 6.3 g of methyl (E)-3-(4-chloro-3-nitrophenyl)acrylate are obtained in the form of a pale yellow solid. Yield=97% b. Preparation of methyl (E)-3-[3'-(1-methyl-3-pentylureido)-2-nitrobiphenyl-4-yl]acrylate In a manner similar to that of Example (18d), by reaction of 38 mg (2 mol %) of palladium acetate, 118 mg (4 mol %) of dicyclohexylbiphenylphosphine, 2.0 g (8.28 mmol, 1.0 eq) of methyl (E)-3-(4-chloro-3-nitrophenyl)acrylate and 2.6 g (9.9 mmol, 1.2 eq) of 3-(1-methyl-3-pentylureido)phenylboronic acid in 25 mL of a mixture of dimethylformamide/2M potassium phosphate solution (4/1), 2.90 g of methyl (E)-3-[3'-(1-methyl-3-pentylureido)-2-nitrobiphenyl-4-yl]acrylate are obtained in the form of a yellow oil. Yield=82% c. Preparation of methyl 3-[2-amino-3'-(1-methyl-3-pentylureido)biphenyl-4-yl]propanoate In a manner similar to that of Example (18e), by reaction of 300 mg (10% by mass) of 10% palladium-on-charcoal and 2.90 g (6.8 mmol, 1 eq) of methyl (E)-3-[3'-(1-methyl-3-pentylureido)-2-nitrobiphenyl-4-yl]acrylate in 50 ml of methanol, and after purification by chromatography on silica gel (50/50 heptane/ethyl acetate), 2.57 g of methyl 3-[2-amino-3'-(1-methyl-3-pentylureido)biphenyl-4-yl]propanoate are obtained in the form of a yellow oil. Yield=95% d. Synthesis of 3-[2-amino-3'-(1-methyl-3-pentylureido)biphenyl-4-yl]propanoic acid A solution of 123.9 mg (0.311 mmol, 1 eq) of methyl 3-[2-amino-3'-(1-methyl-3-pentylureido)biphenyl-4-yl]propanoate in 3 ml of tetrahydrofuran in the presence of 550 µL (0.623 mmol, 2 eq) of 1N lithium hydroxide solution is stirred at room temperature for 4 hours. The reaction medium is concentrated, hydrolyzed with water, acidified with acetic acid and extracted with ethyl acetate. The organic phase is dried over sodium sulfate and evaporated. The residue is taken up in heptane and then recrystallized from acetonitrile. 302.8 mg of 3-[2-amino-3'-(1-methyl-3-pentylureido)biphenyl-4-yl]propanoic acid are obtained in the form of a white powder (m.p.=84.9° C.) Yield=75%

$^1$H NMR (CDCl$_3$, 400 MHz): 0.85 (t, 3H); 1.19-1.31 (m, 4H); 1.31-1.46 (m, 2H); 2.70 (t, 2H); 2.92 (t, 2H); 3.15-3.20 (q, 2H); 3.29 (s, 3H); 4.45 (t, 1H); 6.65 (s, 1H); 6.69 (d, 1H); 7.03 (d, 1H); 7.22 (d, 1H); 7.34 (s, 1H); 7.39 (d, 1H); 7.47 (t, 1H).

Example 53

Synthesis of 3-[2-butylamino-3'-(1-methyl-3-pentylureido)biphenyl-4-yl]propanoic acid hydrochloride

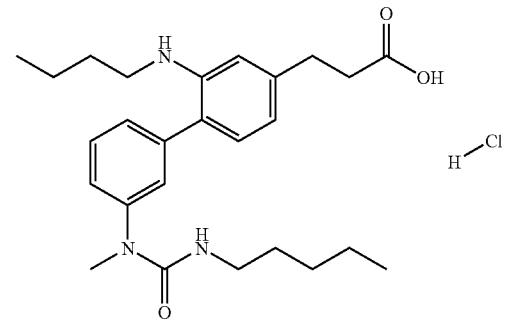

a. Preparation of methyl 3-[2-butylamino-3'-(1-methyl-3-pentylureido)biphenyl-4-yl]propanoate A solution of 200 mg (0.5 mmol, 1 eq) of methyl 3-[2-amino-3'-(1-methyl-3-pentylureido)biphenyl-4-yl]propanoate (prepared in Example 52c) and 60 µL (0.55 mmol, 1.1 eq) of 1-iodobutane in 2 ml of dimethylformamide in the presence of 170 µL (10.5 mmol, 2.1 eq) of diisopropylethylamine is heated at 80° C. for 16 hours. The reaction medium is hydrolyzed with water and then extracted with ethyl acetate. The organic phases are combined, washed with saturated sodium chloride solution and dried over sodium sulfate.

The solvent is evaporated off and the residue is chromatographed on silica gel (70/30 heptane/ethyl acetate). 114.8 mg of methyl 3-[2-butylamino-3'-(1-methyl-3-pentylureido)biphenyl-4-yl]propanoate are obtained in the form of a yellow oil. Yield=51% b. Synthesis of 3-[2-butylamino-3'-(1-methyl-3-pentylureido)biphenyl-4-yl]propanoic acid hydrochloride In a manner similar to that of Example (52d), by reaction of 114.8 mg (0.25 mmol, 1 eq) of methyl 3-[2-butylamino-3'-(1-methyl-3-pentylureido)biphenyl-4-yl]propanoate and 500 μL (0.50 mmol, 2 eq) of 1N lithium hydroxide solution in 2 ml of tetrahydrofuran, the product is obtained and is precipitated in hydrochloride form by addition of a solution of hydrogen chloride in ethyl acetate. The solid obtained is recrystallized from acetonitrile and 44 mg of 3-[2-butylamino-3'-(1-methyl-3-pentylureido)biphenyl-4-yl]propanoic acid hydrochloride are obtained in the form of a white powder (m.p.=163.9° C.). Yield=37%

$^1$H NMR (CDCl$_3$, 400 MHz): 0.79 (t, 3H); 0.82 (t, 3H); 1.18-1.28 (m, 6H); 1.41-1.49 (m, 2H); 1.63-1.69 (m, 2H); 2.70 (t, 2H); 3.02 (t, 2H); 3.08-3.16 (m, 4H); 3.29 (s, 3H); 5.35 (m, 1H); 7.24-7.36 (m, 5H); 7.50 (t, 1H); 7.72 (s, 1H).

Example 54

Synthesis of 3-[2-benzylamino-3'-(1-methyl-3-pentylureido)biphenyl-4-yl]propanoic acid hydrochloride

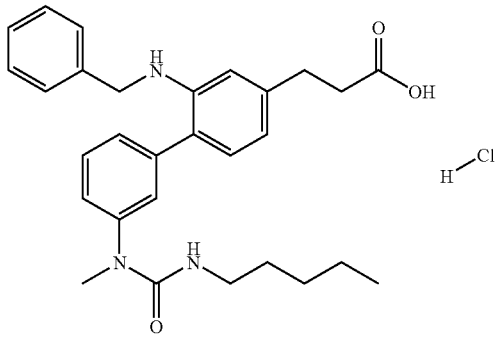

a. Preparation of methyl 3-[2-benzylamino-3'-(1-methyl-3-pentylureido)biphenyl-4-yl]propanoate A solution of 200 mg (0.5 mmol, 1 eq) of methyl 3-[2-amino-3'-(1-methyl-3-pentylureido)biphenyl-4-yl]propanoate (prepared in Example 52c) and 72 μL (0.70 mmol, 1.4 eq) of benzaldehyde in 4 ml of methanol in the presence of 63 mg (1.0 mmol, 2 eq) of sodium cyanoborohydride is stirred at room temperature for 16 hours. The reaction medium is hydrolyzed with ammonium chloride solution and then extracted with ethyl acetate. The organic phases are combined, washed with saturated sodium chloride solution and dried over sodium sulfate. The solvent is evaporated off and the residue is chromatographed on silica gel (70/30 heptane/ethyl acetate). 144 mg of methyl 3-[2-benzylamino-3'-(1-methyl-3-pentylureido)biphenyl-4-yl]propanoate are obtained in the form of a colorless oil. Yield=59% b. Synthesis of 3-[2-benzylamino-3'-(1-methyl-3-pentylureido)biphenyl-4-yl]propanoic acid hydrochloride In a manner similar to that of Example (52d), by reaction of 144 mg (0.30 mmol, 1 eq) of methyl 3-[2-benzylamino-3'-(1-methyl-3-pentylureido)biphenyl-4-yl]propanoate and 590 μL (0.60 mmol, 2 eq) of 1N lithium hydroxide solution in 2 ml of tetrahydrofuran, 42 mg of 3-[2-benzylamino-3'-(1-methyl-3-pentylureido)biphenyl-4-yl]propanoic acid hydrochloride are obtained in the form of a white powder (m.p.=105° C.). Yield=28%

$^1$H NMR (CDCl$_3$, 400 MHz): 0.84 (t, 3H); 1.20-1.30 (m, 8H); 1.41-1.49 (m, 2H); 2.65 (t, 2H); 2.95 (t, 2H); 3.17 (m, 2H); 3.22 (s, 3H); 4.32 (s, 2H); 4.95 (m, 1H); 6.98 (m, 2H); 7.07 (d, 2H); 7.20-7.28 (m, 7H); 7.39 (t, 1H).

Example 55

Synthesis of 3-[2-diethylamino-3'-(1-methyl-3-pentylureido)biphenyl-4-yl]propanoic acid hydrochloride

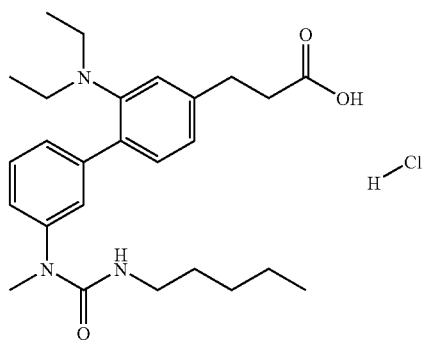

a. Preparation of methyl 3-[2-diethylamino-3'-(1-methyl-3-pentylureido)biphenyl-4-yl]propanoate In a manner similar to that of Example (54a), by reaction of 300 mg (0.75 mmol, 1 eq) of methyl 3-[2-amino-3'-(1-methyl-3-pentylureido)biphenyl-4-yl]propanoate (prepared in Example 52c) and 100 μL (1.70 mmol, 2.4 eq) of acetaldehyde in 6 ml of methanol in the presence of 95 mg (1.5 mmol, 2 eq) of sodium cyanoborohydride, 279.3 mg of methyl 3-[2-diethylamino-3'-(1-methyl-3-pentylureido)biphenyl-4-yl]propanoate are obtained in the form of a colorless oil. Yield=82% b. Synthesis of 3-[2-diethylamino-3'-(1-methyl-3-pentylureido)biphenyl-4-yl]propanoic acid hydrochloride In a manner similar to that of Example (52d), by reaction of 279 mg (0.62 mmol, 1 eq) of methyl 3-[2-diethylamino-3'-(1-methyl-3-pentylureido)biphenyl-4-yl]propanoate and 1.23 mL (1.24 mmol, 2 eq) of 1N lithium hydroxide solution in 3 ml of tetrahydrofuran, 214 mg of 3-[2-diethylamino-3'-(1-methyl-3-pentylureido)biphenyl-4-yl]propanoic acid hydrochloride are obtained in the form of a white powder (m.p.=183.2° C.) Yield=73%

$^1$H NMR (CDCl$_3$, 400 MHz): 0.84 (t, 3H); 1.15 (t, 6H); 1.22-1.31 (m, 4H); 1.49-1.54 (m, 2H); 2.70 (t, 2H); 3.07 (t,

2H); 3.14 (m, 2H); 3.25 (s, 3H); 3.77 (m, 2H); 6.65 (m, 1H); 7.03 (s, 1H); 7.07 (d, 1H); 7.30 (d, 2H); 7.38 (d, 2H); 7.52 (t, 1H); 11.2 (m, 1H).

Example 56

Synthesis of 3-[3'-(1-methyl-3-pentylureido)-2-propylaminobiphenyl-4-yl]propanoic acid hydrochloride

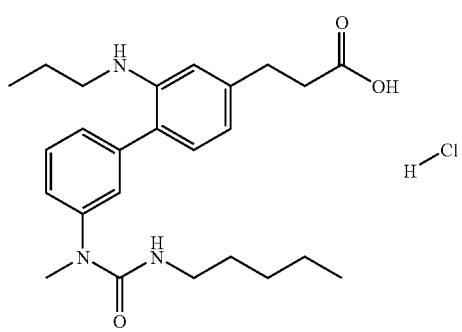

a. Preparation of methyl 3-[3'-(1-methyl-3-pentylureido)-2-propylaminobiphenyl-4-yl]propanoate In a manner similar to that of Example (54a), by reaction of 300 mg (0.75 mmol, 1 eq) of methyl 3-[2-amino-3'-(1-methyl-3-pentylureido)biphenyl-4-yl]propanoate (prepared in Example 52c) and 77 µL (1.70 mmol, 1.4 eq) of propionaldehyde in 6 ml of methanol in the presence of 95 mg (1.5 mmol, 2 eq) of sodium cyanoborohydride, 207.3 mg of methyl 3-[3'-(1-methyl-3-pentylureido)-2-propylaminobiphenyl-4-yl]propanoate are obtained in the form of a colorless oil. Yield=62% b. Synthesis of 3-[3'-(1-methyl-3-pentylureido)-2-propylaminobiphenyl-4-yl]propanoic acid hydrochloride In a manner similar to that of Example (52d), by reaction of 207 mg (0.47 mmol, 1 eq) of methyl 3-[3'-(1-methyl-3-pentylureido)-2-propylaminobiphenyl-4-yl]propanoate and 0.94 mL (0.94 mmol, 2 eq) of 1N lithium hydroxide solution in 4 ml of tetrahydrofuran, 178.4 mg of 3-[3'-(1-methyl-3-pentylureido)-2-propylaminobiphenyl-4-yl]propanoic acid hydrochloride are obtained in the form of a white powder (m.p.=172.8° C.). Yield=82%

$^1$H NMR (CDCl$_3$, 400 MHz): 0.79-0.84 (2t, 6H); 1.18-1.28 (m, 8H); 1.41-1.47 (m, 2H); 1.67-1.73 (m, 2H); 2.69 (t, 2H); 3.02 (t, 2H); 3.06 (m, 2H); 3.14 (t, 2H); 3.29 (s, 3H); 5.45 (m, 1H); 7.24-7.34 (m, 5H); 7.50 (t, 1H); 7.68 (s, 1H).

Example 57

Synthesis of 3-[2-(4-fluorobenzylamino)-3'-(1-methyl-3-pentylureido)biphenyl-4-yl]propanoic acid hydrochloride

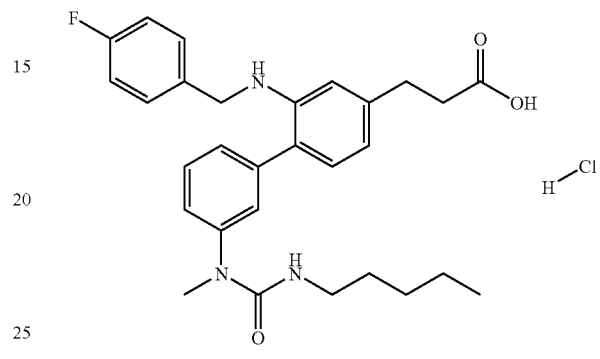

a. Preparation of methyl 3-[2-(4-Fluorobenzylamino)-3'-(1-methyl-3-pentylureido)biphenyl-4-yl]propanoate In a manner similar to that of Example (54a), by reaction of 200 mg (0.5 mmol, 1 eq) of methyl 3-[2-amino-3'-(1-methyl-3-pentylureido)biphenyl-4-yl]propanoate (prepared in Example 52c) and 76 µL (0.70 mmol, 1.4 eq) of 4-fluorobenzaldehyde in 4 ml of methanol in the presence of 63 mg (1.0 mmol, 2 eq) of sodium cyanoborohydride, 220.3 mg of methyl 3-[2-(4-fluorobenzylamino)-3'-(1-methyl-3-pentylureido)biphenyl-4-yl]propanoate are obtained in the form of a colorless oil. Yield=87% b. Synthesis of 3-[2-(4-fluorobenzylamino)-3'-(1-methyl-3-pentylureido)biphenyl-4-yl]propanoic acid hydrochloride In a manner similar to that of Example (52d), by reaction of 220 mg (0.47 mmol, 1 eq) of methyl 3-[2-(4-fluorobenzylamino)-3'-(1-methyl-3-pentylureido)biphenyl-4-yl]propanoate and 0.87 mL (0.87 mmol, 2 eq) of 1N lithium hydroxide solution in 4 ml of tetrahydrofuran, 98 mg of 3-[2-(4-fluorobenzylamino)-3'-(1-methyl-3-pentylureido)biphenyl-4-yl]propanoic acid hydrochloride are obtained in the form of a white powder (m.p.=169.6° C.). Yield=43%

$^1$H NMR (CD$_3$OD, 400 MHz): 0.88 (t, 3H); 1.29-1.33 (m, 4H); 1.49-1.54 (m, 2H); 2.68 (m, 2H); 3.01 (m, 2H); 3.18 (m, 2H); 3.25 (s, 3H); 4.49 (s, 2H); 6.84 (s, 1H); 7.01-7.07 (m, 3H); 7.15 (m, 2H); 7.16 (d, 1H); 7.33-7.37 (m, 3H); 7.50 (m, 1H).

Example 58

Synthesis of 3-[2-butylamino-3'-(3-heptyl-1-methylureido)biphenyl-4-yl]propanoic acid hydrochloride

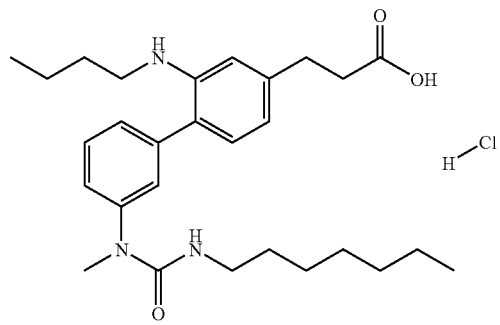

a. Preparation of 1-(3-bromophenyl)-3-heptyl-1-methylurea

In a manner similar to that of Example (46a), by reaction of 50.0 g (0.354 mol, 1 eq) of heptyl isocyanate and 65.9 g (0.354 mol, 1 eq) of (3-bromophenyl)methylamine (prepared in Example 7c) in 300 mL of dichloromethane in the presence of 20 mL (0.143 mol, 0.4 eq) of triethylamine, 113 g of 1-(3-bromophenyl)-3-heptyl-1-methylurea are obtained. Yield=97% b. Preparation of 3-(3-heptyl-1-methylureido)phenylboronic acid

In a manner similar to that of Example (18a), by reaction of 113 g (0.345 mol, 1 eq) of 1-(3-bromophenyl)-3-heptyl-1-methylurea in 1.13 L of tetrahydrofuran, 127 mL (0.38 mol, 1.1 eq) of methyllithium, 530 mL (0.76 mol, 2.2 eq) of a 1.7M solution of tert-butyllithium in pentane and 97 mL (0.904 mol, 2.2 eq) of trimethyl borate, and after purification by chromatography on silica gel (50/50 heptane/ethyl acetate) and crystallization from ethyl acetate/heptane, 36.0 g of 3-(3-heptyl-1-methylureido)phenylboronic acid are obtained in the form of a pinkish powder. Yield=36% c. Preparation of methyl (E)-3-[3'-(3-heptyl-1-methylureido)-2-nitrobiphenyl-4-yl]acrylate In a manner similar to that of Example (18d), by reaction of 56 mg (2 mol %) of palladium acetate, 174 mg (4 mol %) of dicyclohexylbiphenylphosphine, 3.0 g (12.0 mmol, 1.0 eq) of methyl (E)-3-(4-chloro-3-nitrophenyl)acrylate (prepared in Example 52a) and 4.4 g (15.0 mmol, 1.2 eq) of 3-(3-heptyl-1-methylureido)phenylboronic acid in 48 mL of a mixture of dimethylformamide/2M potassium phosphate solution (5/1), 4.06 g of methyl (E)-3-[3'-(3-heptyl-1-methylureido)-2-nitrobiphenyl-4-yl]acrylate are obtained in the form of a pale yellow powder. Yield=72% d. Preparation of methyl 3-[2-amino-3'-(3-heptyl-1-methylureido)biphenyl-4-yl]propanoate In a manner similar to that of Example (18e), by reaction of 400 mg (10% by mass) of 10% palladium-on-charcoal and 4.0 g (8.8 mmol, 1 eq) of methyl (E)-3-[3'-(3-heptyl-1-methylureido)-2-nitrobiphenyl-4-yl]acrylate in 80 ml of methanol, and after purification by chromatography on silica gel (50/50 heptane/ethyl acetate), 3.81 g of methyl 3-[2-amino-3'-(3-heptyl-1-methylureido)biphenyl-4-yl]propanoate are obtained in the form of a colorless oil. Yield=100% e. Preparation of methyl 3-[2-butylamino-3'-(3-heptyl-1-methylureido)biphenyl-4-yl]propanoate In a manner similar to that of Example (54a), by reaction of 400 mg (0.94 mmol, 1 eq) of methyl 3-[2-amino-3'-(3-heptyl-1-methylureido)biphenyl-4-yl]propanoate and 120 μL (1.30 mmol, 1.4 eq) of butyraldehyde in 8 ml of methanol in the presence of 120 mg (1.9 mmol, 2 eq) of sodium cyanoborohydride, 335.5 mg of methyl 3-[2-butylamino-3'-(3-heptyl-1-methylureido)biphenyl-4-yl]propanoate are obtained in the form of a colorless oil. Yield=74% f. Synthesis of 3-[2-butylamino-3'-(3-heptyl-1-methylureido)biphenyl-4-yl]propanoic acid hydrochloride In a manner similar to that of Example (52d), by reaction of 155 mg (0.32 mmol, 1 eq) of methyl 3-[2-butylamino-3'-(3-heptyl-1-methylureido)biphenyl-4-yl]propanoate and 0.64 mL (0.64 mmol, 2 eq) of 1N lithium hydroxide solution in 2 ml of tetrahydrofuran, 67 mg of 3-[2-butylamino-3'-(3-heptyl-1-methylureido)biphenyl-4-yl]propanoic acid hydrochloride are obtained in the form of a white powder (m.p.=132.4° C.) Yield=42%

$^1$H NMR (CDCl$_3$, 400 MHz): 0.79 (t, 3H); 0.83 (t, 3H); 1.16-1.28 (m, 10H); 1.45 (m, 2H); 1.63-1.70 (m, 2H); 2.70 (t, 2H); 3.02-3.10 (m, 4H); 3.10 (t, 2H); 3.30 (s, 3H); 5.25 (m, 1H); 7.23-7.34 (m, 4H); 7.38 (d, 1H); 7.51 (t, 1H); 7.75 (s, 1H).

Example 59

Synthesis of 3-[2-benzylamino-3'-(3-heptyl-1-methylureido)biphenyl-4-yl]propanoic acid hydrochloride

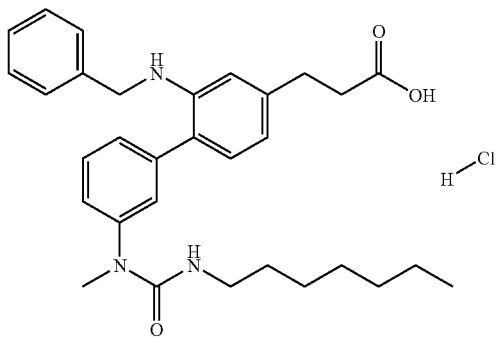

a. Preparation of methyl 3-[2-benzylamino-3'-(3-heptyl-1-methylureido)biphenyl-4-yl]propanoate In a manner similar to that of Example (54a), by reaction of 200 mg (0.5 mmol, 1 eq) of methyl 3-[2-amino-3'-(3-heptyl-1-methylureido)biphenyl-4-yl]propanoate (prepared in Example 58d) and 67 μL (0.66 mmol, 1.4 eq) of benzaldehyde in 4 ml of methanol in the presence of 59 mg (0.94 mmol, 2 eq) of sodium cyanoborohydride, 126.8 mg of methyl 3-[2- benzylamino-3'-(3-heptyl-1-methylureido)biphenyl-4-yl] propanoate are obtained in the form of a colorless oil. Yield=52% b. Synthesis of 3-[2-benzylamino-3'-(3-heptyl-1-methylureido)biphenyl-4-yl]propanoic acid hydrochloride In a manner similar to that of Example (52d), by reaction of 126 mg (0.25 mmol, 1 eq) of methyl 3-[2-benzylamino-3'-(3-heptyl-1-methylureido)biphenyl-4-yl]propanoate and 0.98 mL (0.98 mmol, 2 eq) of 1N lithium hydroxide solution in 2 ml of tetrahydrofuran, 57 mg of 3-[2-benzylamino-3'-(3-heptyl-1-methylureido)biphenyl-4-yl]propanoic acid hydrochloride are obtained in the form of a white powder (m.p.=145.3° C.). Yield=43%

$^1$H NMR (CDCl$_3$, 400 MHz): 0.84 (t, 3H); 1.24-1.27 (m, 8H); 1.49 (m, 2H); 2.63 (t, 2H); 2.97 (t, 2H); 3.18 (m, 2H); 3.20 (s, 3H); 4.32 (s, 2H); 5.5 (m, 1H); 6.70 (s, 1H); 6.80 (d, 1H); 7.09-7.36 (m, 9H); 7.42 (s, 1H).

Example 60

Synthesis of 3-[2-diethylamino-3'-(3-heptyl-1-methylureido)biphenyl-4-yl]propanoic acid hydrochloride

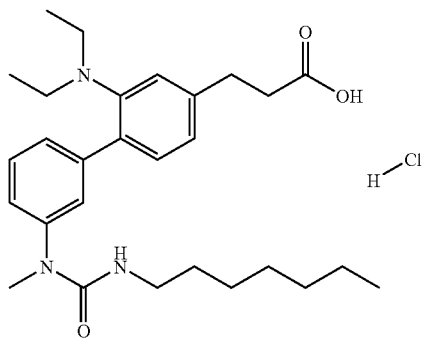

a. Preparation of methyl 3-[2-diethylamino-3'-(3-heptyl-1-methylureido)biphenyl-4-yl]propanoate In a manner similar to that of Example (54a), by reaction of 300 mg (0.7 mmol, 1 eq) of methyl 3-[2-amino-3'-(3-heptyl-1-methylureido)biphenyl-4-yl]propanoate (prepared in Example 58d) and 60 µL (1.06 mmol, 1.5 eq) of acetaldehyde in 6 ml of methanol in the presence of 89 mg (1.4 mmol, 2 eq) of sodium cyanoborohydride, 210 mg of methyl 3-[2-diethylamino-3'-(3-heptyl-1-methylureido)biphenyl-4-yl]propanoate are obtained in the form of a colorless oil. Yield=62% b. Synthesis of 3-[2-diethylamino-3'-(3-heptyl-1-methylureido)biphenyl-4-yl]propanoic acid hydrochloride In a manner similar to that of Example (52d), by reaction of 210 mg (0.44 mmol, 1 eq) of methyl 3-[2-diethylamino-3'-(3-heptyl-1-methylureido)biphenyl-4-yl]propanoate and 0.87 mL (0.87 mmol, 2 eq) of 1N lithium hydroxide solution in 4 ml of tetrahydrofuran, 132 mg of 3-[2-diethylamino-3'-(3-heptyl-1-methylureido)biphenyl-4-yl]propanoic acid hydrochloride are obtained in the form of a white powder (m.p.=178.6° C.). Yield=60%

$^1$H NMR (CDCl$_3$, 400 MHz): 0.84 (t, 3H); 1.13 (t, 3H); 1.23-1.28 (m, 8H); 1.50 (m, 2H); 2.74 (t, 2H); 3.08 (t, 2H); 3.23 (s, 3H); 3.27 (m, 2H); 3.75 (m, 2H); 6.7 (m, 1H); 7.00 (s, 1H); 7.08 (d, 1H); 7.28 (d, 2H); 7.37 (d, 2H); 7.51 (t, 1H).

Example 61

Synthesis of 3-[3'-(3-heptyl-1-methylureido)-2-propylaminobiphenyl-4-yl]propanoic acid hydrochloride

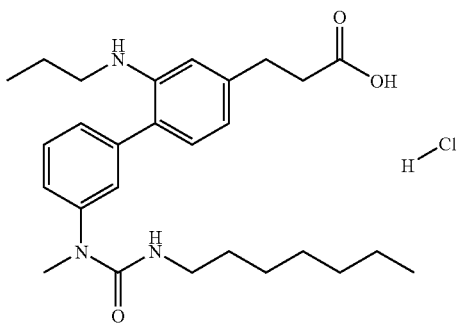

a. Preparation of methyl 3-[3'-(3-heptyl-1-methylureido)-2-propylaminobiphenyl-4-yl]propanoate In a manner similar to that of Example (54a), by reaction of 300 mg (0.7 mmol, 1 eq) of methyl 3-[2-amino-3'-(3-heptyl-1-methylureido)biphenyl-4-yl]propanoate (prepared in Example 58d) and 72 µL (0.99 mmol, 1.4 eq) of propionaldehyde in 6 ml of methanol in the presence of 89 mg (1.4 mmol, 2 eq) of sodium cyanoborohydride, 131.6 mg of methyl 3-[3'-(3-heptyl-1-methylureido)-2-propylaminobiphenyl-4-yl]propanoate are obtained in the form of a colorless oil. Yield=40% b. Synthesis of 3-[3'-(3-heptyl-1-methylureido)-2-propylaminobiphenyl-4-yl]propanoic acid hydrochloride In a manner similar to that of Example (52d), by reaction of 131 mg (0.44 mmol, 1 eq) of methyl 3-[3'-(3-heptyl-1-methylureido)-2-propylaminobiphenyl-4-yl]propanoate and 0.56 mL (0.56 mmol, 2 eq) of 1N lithium hydroxide solution in 2 ml of tetrahydrofuran, 102 mg of 3-[3'-(3-heptyl-1-methylureido)-2-propylaminobiphenyl-4-yl]propanoic acid hydrochloride are obtained in the form of a white powder (m.p.=140.8° C.). Yield=74%

$^1$H NMR (CDCl$_3$, 400 MHz): 0.79-0.86 (2t, 6H); 1.25 (m, 8H); 1.45 (m, 2H); 1.67-1.72 (m, 2H); 2.70 (t, 2H); 3.02 (t, 2H); 3.05 (m, 2H); 3.15 (m, 2H); 3.29 (s, 3H); 5.35 (m, 1H); 7.23-7.34 (m, 5H); 7.50 (t, 1H); 7.67 (s, 1H).

Example 62

Synthesis of 3-[2-(4-fluorobenzylamino)-3'-(3-heptyl-1-methylureido)biphenyl-4-yl]propanoic acid hydrochloride

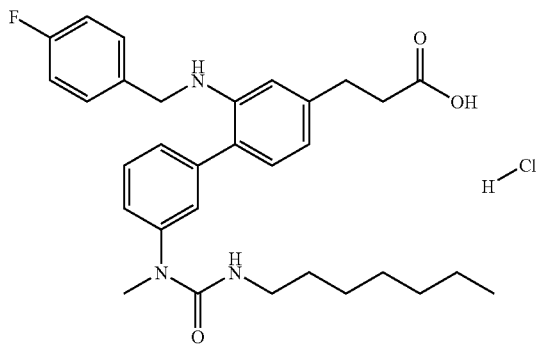

a. Preparation of methyl 3-[2-(4-fluorobenzylamino)-3'-(3-heptyl-1-methylureido)biphenyl-4-yl]propanoate In a manner similar to that of Example (54a), by reaction of 200 mg (0.47 mmol, 1 eq) of methyl 3-[2-amino-3'-(3-heptyl-1-methylureido)biphenyl-4-yl]propanoate (prepared in Example 58d) and 71 µL (0.99 mmol, 1.4 eq) of 4-fluorobenzaldehyde in 4 ml of methanol in the presence of 59 mg (1.4 mmol, 2 eq) of sodium cyanoborohydride, 207.1 mg of methyl 3-[2-(4-fluorobenzylamino)-3'-(3-heptyl-1-methylureido)biphenyl-4-yl]propanoate are obtained in the form of a colorless oil. Yield=83% b. Synthesis of 3-[2-(4-fluorobenzylamino)-3'-(3-heptyl-1-methylureido)biphenyl-4-yl]propanoic acid hydrochloride In a manner similar to that of Example (52d), by reaction of 207 mg (0.38 mmol, 1 eq) of methyl 3-[2-(4-fluorobenzylamino)-3'-(3-heptyl-1-methylureido)biphenyl-4-yl]propanoate and 0.78 mL (0.78 mmol, 2 eq) of 1N lithium hydroxide solution in 4 ml of tetrahydrofuran, 154 mg of 3-[2-(4-fluorobenzylamino)-3'-(3-heptyl-1-methylureido)biphenyl-4-yl]propanoic acid hydrochloride are obtained in the form of a white powder. Crude yield=73%

$^1$H NMR (CD$_3$OD, 400 MHz): 0.80 (t, 3H); 1.14-1.20 (m, 8H); 1.39 (m, 2H); 2.59 (m, 2H); 3.02 (m, 2H); 3.06 (m, 2H); 3.20 (s, 3H); 4.24 (s, 2H); 6.91 (m, 1H); 7.18-7.29 (m, 8H); 7.41 (t, 1H); 7.46 (m, 1H).

Example 63

Cross-Curve Ppar Transactivation Tests

The activation of PPAR receptors with an agonist (activator) in HeLN cells leads to the expression of a reporter gene, luciferase, which, in the presence of a substrate, generates light. The modulation of the PPAR receptors is measured by quantifying the luminescence produced after incubating the cells in the presence of a reference agonist. The ligands displace the agonist from its site. The measurement of the activity is performed by quantifying the light produced. This measurement makes it possible to determine the modulatory activity of the compounds according to the invention by determining the constant that is the affinity of the molecule for the PPAR receptor. Since this value can fluctuate depending on the basal activity and the expression of the receptor, it is referred to as Kd apparent (KdApp in nM).

To determine this constant, "cross curves" of the test product against a reference agonist are produced in a 96-well plate: 10 concentrations of the test product plus a concentration 0 are arranged in a line, and 7 concentrations of the agonist plus a concentration 0 are arranged in a column. This is 88 measurement points for 1 product and 1 receptor. The remaining 8 wells are used for repeatability controls.

In each well, the cells are in contact with a concentration of the test product and a concentration of the reference agonist, 2-(4-{2-[3-(2,4-difluorophenyl)-1-heptylureido]ethyl}phenylsulfanyl)-2-methylpropionic acid for PPARα, {2-methyl-4-[4-methyl-2-(4-trifluoromethylphenyl)thiazol-5-ylmethylsulfanyl]phenoxy}acetic acid for PPARδ and 5-{4-[2-(methylpyrid-2-ylamino)ethoxy]benzyl}thiazolidine-2,4-dione for PPARγ. Measurements are also taken for total agonist controls with the same products.

The HeLN cell lines used are stable transfectants containing the plasmids ERE-βGlob-Luc-SV-Neo (reporter gene) and PPAR (α, δ, γ) Gal-hPPAR. These cells are inoculated into 96-well plates at a rate of 10 000 cells per well in 100 µl of DMEM medium without phenol red and supplemented with 10% of defatted calf serum. The plates are then incubated at 37° C. and 7% CO$_2$ for 16 hours.

The various dilutions of the test products and of the reference ligand are added at a rate of 5 µl per well. The plates are then incubated for 18 hours at 37° C. and 7% CO$_2$. The culture medium is removed by turning over and 100 µl of a 1:1 PBS/luciferin mixture are added to each well. After 5 minutes, the plates are read by the luminescence detector.

These cross curves make it possible to determine the AC50 values (concentration at which 50% activation is observed) of the reference ligand at various concentrations of test product. These AC50 values are used to calculate the Schild regression by plotting a straight line corresponding to the Schild equation ("quantitation in receptor pharmacology" Terry P. Kenakin, Receptors and Channels, 2001, 7, 371-385), which allows the Kd app values (in nM) to be obtained.

Transactivation Results:

| Compounds | PPAR alpha Kd app (in nM) | PPARs delta Kd app (in nM) | PPAR gamma Kd app (in nM) |
|---|---|---|---|
| Reference 1: 2-(4-{2-[3-(2,4-Difluorophenyl)-1-heptylureido]-ethyl}phenylsulfanyl)-2-methylpropionic acid | 200 | n.a. | n.a |
| Reference 2: {2-Methyl-4-[4-methyl-2-(4-trifluoromethylphenylthiazol-5-ylmethysulfanyl]phenoxy}acetic acid | n.a. | 10 | n.a |
| Reference 3: 5-{4-[2-(Methyl-pyrid-2-ylamino)ethoxy]benzyl}-thiazolidine-2,4-dione | n.a | n.a | 30 |
| Example 2 | n.a. | 500 | 2 |
| Example 3 | 2000 | 2000 | 4 |
| Example 13 | 9999 | 2000 | 2 |
| Example 14 | 500 | 500 | 2 |
| Example 15 | 2000 | 2000 | 2 |
| Example 16 | 1000 | n.a. | 1 |

-continued

| Compounds | PPAR alpha Kd app (in nM) | PPARs delta Kd app (in nM) | PPAR gamma Kd app (in nM) |
|---|---|---|---|
| Example 17 | 500 | n.a. | 1 |
| Example 18 | 2000 | 250 | 4 |
| Example 24 | 500 | 2000 | 4 |
| Example 25 | 500 | 120 | 0.25 |
| Example 26 | 250 | 1000 | 0.25 |
| Example 33 | n.a. | 1000 | 4 |
| Example 34 | 500 | 8 | 2 |
| Example 35 | nd | 1000 | 1 |
| Example 37 | 250 | 2000 | 2 |
| Example 38 | 250 | n.a. | 1 |
| Example 40 | 8000 | n.a. | 1 |
| Example 41 | 60 | 2000 | 0.5 |
| Example 42 | 4000 | n.a. | 1 |
| Example 43 | 2000 | n.a. | 2 |
| Example 44 | 1000 | n.a. | 1 |
| Example 45 | 120 | 8000 | 0.25 |
| Example 46 | 30 | 8000 | 0.25 |
| Example 47 | 1000 | n.a. | 2 |
| Example 48 | 2000 | 8000 | 2 |
| Example 49 | 2000 | n.a. | 2 | n.a means not active;
nd means not determined

These results show the affinity of the compounds for the PPAR receptors and more particularly the specificity of the affinity of the compounds of the invention for the PPARγ subtype, compared with the affinity of the compounds for the PPARα subtype or for the PPARγ subtype.

Example 64

Rat Sebocyte Culture Tests

Sebocytes in culture obtained from rat preputial gland constitute a pertinent model for evaluating sebaceous function modulatory compounds as described by Rosenfield et al. (Mechanisms of androgen induction of sebocyte differentiation. Rosenfield R. L., Deplewski D., Kentsis A., Ciletti N., *Dermatology*, 1998; 196(1):43-6). This model has especially been used to characterize PPAR compounds with potential in dermatology (Rat preputial sebocyte differentiation involves peroxisome proliferator-activated receptors. Rosenfield R. L., Kentsis A., Deplewski D., Ciletti N., *J. Invest. Dermatol.*, 1999 February; 112(2):226-32). These sebocytes have functional similarities close to those of human skin sebocytes (response to androgens and to anti-androgens, accumulation of specific sebum lipids, expression of specific markers of the sebaceous gland). The data resulting from this test are considered as pertinent of potential activity on the human sebaceous gland.

Protocol for culturing sebocytes obtained from rat preputial glands

The preputial glands are obtained from 10-week-old male rats. They are extracted under anesthesia with isoflurane, before euthanizing the animals. The glands are then digested enzymatically with trypsin (0.25% trypsin+collagenase H 1.5 mg/ml/gland). The cells are cultured for 24 hours in 24-well plates (37° C., 5% $CO_2$) in DMEM culture medium supplemented with various factors, especially fetal calf serum (10%), glutamine (1%), a cocktail of antibiotics and antimycotic agents and insulin (5 µg/ml). The cells are then placed in Cellgro medium supplemented with various factors (Mediatech®) and the test compounds are then added in response doses (duplicate). After incubation for 5 days, 10 µl of radio labeled ($^{14}C$) acetate are added to the culture medium (0.2 µCi/µl, Amersham). The cells are incubated for 24 hours and then washed and recovered after digestion with trypsin. The radiolabelled lipids are then extracted using a methanol/dichloromethane mixture (1/2) and placed on a silica TLC plate (Merck®) using a loading robot. The lipids are then separated and quantified after revelation using a Phosphorimager (analysis by image analysis software). For each compound, the AC50 (concentration for which 50% of the effect of the compound is obtained) is determined. The results are expressed as nanomolar concentration for the following specific sebaceous gland lipids: Triglycerides and/or Cholesterol esters.

Results on sebocytes:

| Compounds | Triglycerides AC50 (nM) |
|---|---|
| Example 26 | 0.005 |
| Example 38 | 0.006 |
| Example 44 | 0.008 |
| Example 41 | 0.008 |
| Example 16 | 0.008 |

Example 65

Compositions

Various specific formulations based on the compounds according to the invention are illustrated in this example.

| ORAL ROUTE: | |
|---|---|
| (a) 0.2 g tablet: | |
| Compound of Example 1 | 0.001 g |
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |
| (b) Drinkable suspension in 5 ml ampules: | |
| Compound of Example 5 | 0.001 g |
| Glycerol | 0.500 g |
| 70% sorbitol | 0.500 g |
| Sodium saccharinate | 0.010 g |
| Methyl parahydroxybenzoate | 0.040 g |
| Flavoring | qs |
| Purified water | qs 5 ml |
| (c) 0.2 g tablet: | |
| Compound of Example 2 | 0.050 g |
| Lactose monohydrate | 0.132 g |
| Crosspovidone | 0.007 g |
| Povidone | 0.005 g |
| Aerosil 200 | 0.004 g |
| Magnesium stearate | 0.002 g |
| (d) Drinkable suspension in 10 ml ampules: | |
| Compound of Example 4 | 0.200 g |
| Glycerol | 1.000 g |
| 70% sorbitol | 1.000 g |
| Sodium saccharinate | 0.010 g |
| Methyl parahydroxybenzoate | 0.080 g |
| Flavoring | qs |
| Purified water | qs 10 ml |

-continued

B-TOPICAL ROUTE:

(a) Ointment:

| | |
|---|---|
| Compound of Example 6 | 0.020 g |
| Isopropyl myristate | 81.700 g |
| Fluid petroleum jelly oil | 9.100 g |
| Silica ("Aerosil 200" marketed by Degussa) | 9.180 g |

(b) Ointment:

| | |
|---|---|
| Compound of Example 2 | 0.300 g |
| White petroleum jelly codex | qs 100 g |

(c) Nonionic water-in-oil cream:

| | |
|---|---|
| Compound of Example 1 | 0.100 g |
| Mixture of emulsifying lanolin alcohols, waxes and oils ("Anhydrous Eucerin" marketed by BDF) | 39.900 g |
| Methyl parahydroxybenzoate | 0.075 g |
| Propyl parahydroxybenzoate | 0.075 g |
| Sterile demineralized water | qs 100 g |

(d) Lotion:

| | |
|---|---|
| Compound of Example 3 | 0.100 g |
| Polyethylene glycol (PEG 400) | 69.900 g |
| 95% ethanol | 30.000 g |

(e) Hydrophobic ointment:

| | |
|---|---|
| Compound of Example 5 | 0.300 g |
| Isopropyl myristate | 36.400 g |
| Silicone oil ("Rhodorsil 47 V 300" marketed by Rhône-Poulenc) | 36.400 g |
| Beeswax | 13.600 g |
| Silicone oil ("Abil 300.000 cSt" marketed by Goldschmidt) | qs 100 g |

(f) Nonionic oil-in-water cream:

| | |
|---|---|
| Compound of Example 2 | 1.000 g |
| Cetyl alcohol | 4.000 g |
| Glyceryl monostearate | 2.500 g |
| PEG 50 stearate | 2.500 g |
| Shea butter | 9.200 g |
| Propylene glycol | 2.000 g |
| Methyl parahydroxybenzoate | 0.075 g |
| Propyl parahydroxybenzoate | 0.075 g |
| Sterile demineralized water | qs 100 g |

Each patent, patent application, publication, text and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A biaromatic compound of the following general formula (I)

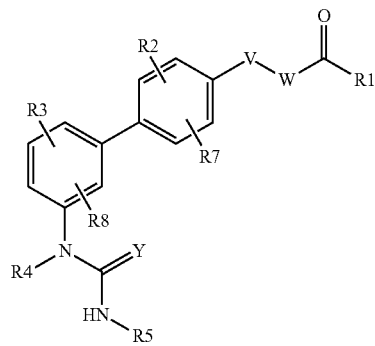

in which:
R1 is a hydroxyl radical, a radical —OR6 or a hydroxylamine radical;
R6 is as defined below;
R2 and R3, which may be identical or different, are each a hydrogen atom, a halogen atom, an alkyl radical having from 1 to 12 carbon atoms, a hydroxyl radical, an alkoxy radical, a polyether radical, an aralkyl radical, an aryl radical, an amino radical that may be substituted by one or two radicals, which may be identical or different, selected from among an alkyl radical having from 1 to 12 carbon atoms and an aralkyl radical;
R4 is a hydrogen atom or a lower alkyl radical having from 1 to 4 carbon atoms;
R5 is an alkyl radical having from 1 to 12 carbon atoms, an aryl radical, or an aralkyl radical;
R6 is an alkyl, aryl or aralkyl radical;
R7 and R8, which may be identical or different, are each a hydrogen atom, a halogen atom, an alkyl radical having from 1 to 12 carbon atoms, a hydroxyl radical, an alkoxy radical, a polyether radical, an aralkyl radical, an aryl radical, an amino radical that may be substituted by one or two radicals, which may be identical or different, selected from among an alkyl radical having from 1 to 12 carbon atoms or an aralkyl radical;
Y is an oxygen or sulfur atom; and
V—W is
CH$_2$—CH$_2$ or CH═CH;
and the salt, or a salt thereof.

2. The biaromatic compound of claim 1, wherein R1 is a hydroxyl radical.

3. The biaromatic compound of claim 1, wherein R1 is an —OR6 radical.

4. The biaromatic compound of claim 1, wherein R1 is a hydroxylamine radical.

5. The biaromatic compound of claim 1, wherein Y is an oxygen atom.

6. The biaromatic compound of claim 1, wherein Y is a sulfur atom.

7. The biaromatic compound of claim 1, wherein said biaromatic compound is a salt of an alkali metal or alkaline earth metal or a salt of an organic amine.

8. The biaromatic compound of claim 1, wherein said biaromatic compound comprises an amine functional group, and is a salt of an inorganic acid or a salt of an organic acid.

9. The biaromatic compound of claim 1, comprising at least one methyl, ethyl, propyl, isopropyl, butyl, tert-butyl, isoamyl, amyl, hexyl, heptyl, octyl, decyl, cyclohexyl, methylcyclohexyl, methylcyclobutyl, methylcyclopentyl or methylcyclohexyl radical substituent.

10. The biaromatic compound of claim 1, comprising at least one phenyl, biphenyl, cinnamyl or naphthyl radical substituent optionally substituted by a halogen atom, a $CF_3$ radical, an alkyl radical having from 1 to 12 carbon atoms, an alkoxy radical, a nitro functional group, a polyether radical, an aryl radical, a benzoyl radical, an alkyl ester group, a carboxylic acid, a hydroxyl radical optionally protected by an acetyl or benzoyl group or an amino radical optionally protected by an acetyl or benzoyl group or optionally substituted by at least one alkyl radical having from 1 to 12 carbon atoms, an aralkoxy radical, a phenoxy radical or an amide radical $H_2NCO$.

11. The biaromatic compound of claim 1, comprising at least one alkyl radical substituent having from 1 to 12 carbon atoms and substituted by an aryl radical.

12. The biaromatic compound of claim 1, comprising at least one fluorine, chlorine, bromine or iodine atom substituent.

13. The biaromatic compound of claim 1, comprising at least one methoxy, ethoxy, isopropyloxy, n-propyloxy, tert-butoxy, n-butoxy, n-pentyloxy, n-hexyloxy, cyclopropylmethoxy, cyclobutylmethoxy, cyclopentylmethoxy or cyclohexylmethoxy radical substituent.

14. The biaromatic compound of claim 1, comprising at least one polyether radical substituent comprising from 1 to 7 carbon atoms and interrupted by at least one oxygen atom.

15. The biaromatic compound of claim 1, selected from the group consisting of:

1. (E)-3-[3'-(3-heptyl-1-methylureido)biphenyl-4-yl]acrylic acid,
2. 3-[3'-(3-heptyl-1-methylureido)biphenyl-4-yl]propanoic acid,
3. 3-[3-fluoro-3'-(3-heptyl-1-methylureido)biphenyl-4-yl]propanoic acid,
4. 3-(3'-{3-[2-(4-fluorophenyl)ethyl]-1-methylureido}biphenyl-4-yl)propanoic acid,
5. 3-[3'-(1-methyl-3-pentylureido)biphenyl-4-yl]propanoic acid,
6. 3-[3'-(3-heptyl-1-methylureido)biphenyl-4-yl]-N-hydroxypropionamide,
7. 3-[3'-(1-methyl-3-naphthalen-2-ylureido)biphenyl-4-yl]propanoic acid,
8. 3-[3'-(3-heptyl-1-methylthioureido)biphenyl-4-yl]propanoic acid,
9. (E)-3-[2-fluoro-3'-(3-heptyl-1-methylureido)biphenyl-4-yl]acrylic acid,
10. 3-[2-fluoro-3'-(3-heptyl-1-methylureido)biphenyl-4-yl]propanoic acid,
11. 3-[3'-(3-hexyl-1-methylureido)biphenyl-4-yl]propanoic acid,
12. 3-[3'-(3-octyl-1-methylureido)biphenyl-4-yl]propanoic acid,
13. 3-{3'-[3-(4-benzyloxyphenyl)-1-methylureido]biphenyl-4-yl}propanoic acid,
14. 3-{3'-[3-(4-butylphenyl)-1-methylureido]biphenyl-4-yl}propanoic acid,
15. 3-[3'-(3-heptyl-1-methylureido)-2-(2-methoxyethoxy)biphenyl-4-yl]propanoic acid,
16. 3-[3'-(3-heptyl-1-methylureido)-2-(3-methylbutoxy)biphenyl-4-yl]propanoic acid,
17. 3-[2-(3-chloropropoxy)-3'-(3-heptyl-1-methylureido)biphenyl-4-yl]propanoic acid,
18. 3-[3'-(3-heptyl-1-methylureido)-2-methoxybiphenyl-4-yl]propanoic acid,
19. 3-[3'-(3-heptyl-1-methylureido)-2-methylbiphenyl-4-yl]propanoic acid,
20. 3-[3'-[1-methyl-3-(3-phenylpropyl)ureido]biphenyl-4-yl]propanoic acid,
21. (E)-3-[5'-(3-heptyl-1-methylureido)-2'-methylbiphenyl-4-yl]acrylic acid,
22. 3-[5'-(3-heptyl-1-methylureido)-2'-methylbiphenyl-4-yl]propanoic acid,
23. (E)-3-[3-fluoro-3'-(3-heptyl-1-methylureido)biphenyl-4-yl]acrylic acid,
24. (E)-3-[2-benzyloxy-3'-(3-heptyl-1-methylureido)biphenyl-4-yl]acrylic acid,
25. 3-[3'-(3-heptyl-1-methylureido)-2-propoxybiphenyl-4-yl]propanoic acid,
26. 3-[2-butoxy-3'-(3-heptyl-1-methylureido)biphenyl-4-yl]propanoic acid,
27. (E)-3-[3'-(1-ethyl-3-heptylureido)biphenyl-4-yl]acrylic acid,
28. (E)-3-[3'-(3-heptyl-1-propylureido)biphenyl-4-yl]acrylic acid,
29. (E)-3-[3,5-difluoro-3'-(3-heptyl-1-methylureido)biphenyl-4-yl]acrylic acid,
30. 3-[3'-(1-ethyl-3-heptylureido)biphenyl-4-yl]propanoic acid,
31. 3-[3'-(3-heptyl-1-propylureido)biphenyl-4-yl]propanoic acid,
32. 3-[3,5-difluoro-3'-(3-heptyl-1-methylureido)biphenyl-4-yl]propanoic acid,
33. 3-{3'-[3-(4-butoxyphenyl)-1-methylureido]biphenyl-4-yl}propanoic acid,
34. 3-{3'-[3-(4-butoxyphenyl)-1-ethylureido]biphenyl-4-yl}propanoic acid,
35. 3-[2-cyclopropylmethoxy-3'-(3-heptyl-1-methylureido)biphenyl-4-yl]propanoic acid,
36. 3-[2-ethoxy-3'-(3-heptyl-1-methylureido)biphenyl-4-yl]propanoic acid,
37. 3-[3'-3-heptyl-1-methylureido)-2-(3,3,3-trifluoropropoxy)biphenyl-4-yl]propanoic acid,
38. 3-[3'-(3-heptyl-1-methylureido)-2-(4,4,4-trifluorobutoxy)biphenyl-4-yl]propanoic acid,
39. 3-[3'-(3-heptyl-1-methylureido)-2-(3-hydroxypropoxy)biphenyl-4-yl]propanoic acid,
40. 3-[3'-(3-heptyl-1-methylureido)-2-(4-hydroxybutoxy)biphenyl-4-yl]propanoic acid,
41. 3-[2-butoxy-3'-(1-methyl-3-pentylureido)biphenyl-4-yl]propanoic acid,
42. 3-[2-benzyloxy-3'-(3-heptyl-1-methylureido)biphenyl-4-yl]propanoic acid,
43. 3-[2-(3-fluorobenzyloxy)-3'-(3-heptyl-1-methylureido)biphenyl-4-yl]propanoic acid,
44. 3-[2-(4-fluorobenzyloxy)-3'-(3-heptyl-1-methylureido)biphenyl-4-yl]propanoic acid,
45. 3-[3'-(3-heptyl-1-methylureido)-2-pentyloxybiphenyl-4-yl]propanoic acid,
46. 3-[3'-(1-methyl-3-pentylureido)-2-pentyloxybiphenyl-4-yl]propanoic acid,
47. 3-[2-(2-ethoxyethoxy)-3'-(3-heptyl-1-methylureido)biphenyl-4-yl]propanoic acid,
48. 3-[2-butoxy-3'-(1-methyl-3-phenylureido)biphenyl-4-yl]propanoic acid,
49. 3-[2-(2-ethoxyethoxy)-3'-(1-methyl-3-pentylureido)biphenyl-4-yl]propanoic acid
50. 3-[2-(2-diethylaminoethoxy)-3'-(3-heptyl-1-methylureido)biphenyl-4-yl]propanoic acid hydrochloride,
52. 3-[2-amino-3'-(1-methyl-3-pentylureido)biphenyl-4-yl]propanoic acid, 53. 3-[2-butylamino-3'-(1-methyl-3-pentylureido)biphenyl-4-yl]propanoic acid hydrochloride,
54. 3-[2-benzylamino-3'-(1-methyl-3-pentylureido)biphenyl-4-yl]propanoic acid hydrochloride,
55. 3-[2-diethylamino-3'-(1-methyl-3-pentylureido)biphenyl-4-yl]propanoic acid hydrochloride,
56. 3-[3'-(1-methyl-3-pentylureido)-2-propylaminobiphenyl-4-yl]propanoic acid hydrochloride,
57. 3-[2-(4-fluorobenzylamino)-3'-(1-methyl-3-pentylureido)biphenyl-4-yl]propanoic acid hydrochloride,
58. 3-[2-butylamino-3'-(3-heptyl-1-methylureido)biphenyl-4-yl]propanoic acid hydrochloride,
59. 3-[2-benzylamino-3'-(3-heptyl-1-methylureido)biphenyl-4-yl]propanoic acid hydrochloride,
60. 3-[2-diethylamino-3'-(3-heptyl-1-methylureido)biphenyl-4-yl]propanoic acid hydrochloride,
61. 3-[3'-(3-heptyl-1-methylureido)-2-propylaminobiphenyl-4-yl]propanoic acid hydrochloride,
62. 3-[2-(4-fluorobenzylamino)-3'-(3-heptyl-1-methylureido)biphenyl-4-yl]propanoic acid hydrochloride,
63. 3-[3'-(1-methyl-3-pentylureido)biphenyl-4-yl]acrylic acid,
64. 3-[3'-(3-pentyl-1-propylureido)biphenyl-4-yl]acrylic acid,
65. 3-[4'-fluoro-3'-(1-methyl-3-pentylureido)biphenyl-4-yl]propanoic acid,
66. ethyl 3-[3'-(1-Methyl-3-pentylureido)biphenyl-4-yl]acrylate,
67. 3-[3'-(1-methyl-3-naphthalen-2-ylureido)biphenyl-4-yl]acrylic acid,
68. 3-{3'-[3-(4-fluorophenyl)-1-methylureido]biphenyl-4-yl}acrylic acid,
69. 3-(3'-{3-[2-(4-fluorophenyl)ethyl]-1-methylureido}biphenyl-4-yl)acrylic acid,
70. 3-[3'-(3-benzyl-1-methylureido)biphenyl-4-yl]propanoic acid,
71. 3-[3'-(3-cyclopropylmethyl-1-methylureido)biphenyl-4-yl]propanoic acid,
72. 3-[3'-(3-cyclohexyl-1-methylureido)biphenyl-4-yl]propanoic acid,
73. 3-[3'-(3-cyclohexyl-1-methylureido)biphenyl-4-yl]acrylic acid,
74. 3-[3'-(3-cyclopropylmethyl-1-methylureido)biphenyl-4-yl]acrylic acid,
79. 3-[3'-(1-methyl-3-propylureido)biphenyl-4-yl]acrylic acid,
80. 3-[3'-(3-hexyl-1-methylthioureido)biphenyl-4-yl]propanoic acid,
81. 3-[3'-(3-hexyl-1-methylthioureido)biphenyl-4-yl]acrylic acid,
82. methyl 3-[3'-(3-Heptyl-1-methylthioureido)biphenyl-4-yl]acrylate,
83. 3-[2-methyl-3'-(1-methyl-3-pentylureido)biphenyl-4-yl]propanoic acid,
84. 3-[3-hydroxy-3'-(1-methyl-3-pentylureido)biphenyl-4-yl]propanoic acid,
85. 3-[3-methoxymethoxy-3'-(1-methyl-3-pentylureido)biphenyl-4-yl]propanoic acid,
86. 3-[3'-(1-methyl-3-pentylureido)-2-trifluoromethylbiphenyl-4-yl]propanoic acid,
87. 3-[3'-(3-heptyl-1-methylureido)-3-methoxybiphenyl-4-yl]propanoic acid,
88. 3-{3'-[1-methyl-3-(4-propylphenyl)ureido]biphenyl-4-yl}propanoic acid,
89. 3-{3'-[1-methyl-3-(4-propylphenyl)ureido]biphenyl-4-yl}acrylic acid,
90. phenyl 3-{3'-[1-methyl-3-(4-propylphenyl)ureido]biphenyl-4-yl}acrylate,
91. benzyl 3-{3'-[1-methyl-3-(4-propylphenyl)ureido]biphenyl-4-yl}acrylate,
92. 3-[3'-(3-pentylureido)biphenyl-4-yl]acrylic acid,
93. N-hydroxy-3-{3'-[1-methyl-3-(3-phenylpropyl)ureido]biphenyl-4-yl}propionamide,
94. 3-[3'-(3-heptyl-1-methylureido)-2-hydroxybiphenyl-4-yl]propanoic acid,
95. 3-[2-cyclohexylmethoxy-3'-(3-heptyl-1-methylureido)biphenyl-4-yl]propionic acid,
96. 3-[2-cyclopentylmethoxy-3'-(3-heptyl-1-methylureido)biphenyl-4-yl]propionic acid,
97. 3-[2-cyclobutylmethoxy-3'-(3-heptyl-1-methylureido)biphenyl-4-yl]-N-hydroxypropionamide,
98. 3-[3'-(3-heptyl-1-methylureido)-2-(3-trifluoromethylbenzyloxy)biphenyl-4-yl]propanoic acid,
99. 3-[3'-(3-heptyl-1-methylureido)-2-(4-trifluoromethylbenzyloxy)biphenyl-4-yl]propanoic acid,
100. 3-[2-(3-carbamoylbenzyloxy)-3'-(3-heptyl-1-methylureido)biphenyl-4-yl]propanoic acid,
103. 3-(2-(3-methoxybenzyloxy)-3'-{3-[2-(3-methoxyphenyl)ethyl]-1-methylureido}biphenyl-4-yl)propanoic acid,
104. 3-(2-(4-tert-butylbenzyloxy)-3'-{1-methyl-3-[2-(3-phenoxyphenyl)ethyl]-ureido}biphenyl-4-yl)propanoic acid,
105. 3-{2-(3,5-dimethoxybenzyloxy)-3'-[1-methyl-3-(3-phenoxyphenyl)ureido]biphenyl-4-yl}propanoic acid,
106. 3-[3'-[1-methyl-3-(4-phenoxyphenyl)ureido]-2-(3-trifluoromethylbenzyloxy)biphenyl-4-yl]propanoic acid,
107. 3-(2-(3-isopropoxybenzyloxy)-3'-{3-[2-(4-methoxyphenyl)ethyl]-1-methylureido}biphenyl-4-yl)propanoic acid,
108. 3-(2'-(3-methoxybenzyloxy)-5'-{3-[2-(3-methoxyphenyl)ethyl]-1-methylureido}biphenyl-4-yl)propanoic acid,
109. 3-[2'-cyclohexylmethoxy-5'-(1-methyl-3-pentylureido)biphenyl-4-yl]propanoic acid,
110. 3-[4'-ethoxy-3'-(1-methyl-3-pentylureido)-2-propoxybiphenyl-4-yl]propanoic acid,
111. 3-[3,5-dimethoxy-3'-(1-methyl-3-pentylureido)biphenyl-4-yl]propanoic acid,
112. 3-(3,5-diethoxy-3'-{3-[2-(3-methoxyphenyl)ethyl]-1-methylureido}biphenyl-4-yl)propanoic acid,
113. 3-(3'-{3-[2-(4-methoxyphenyl)ethyl]-1-methylureido}-3-propoxybiphenyl-4-yl)propanoic acid,
114. 3-[3-cyclopropylmethoxy-3'-(1-methyl-3-pentylureido)biphenyl-4-yl]propanoic acid,
115. 3-[3-ethoxy-4'-fluoro-3'-(1-methyl-3-pentylureido)biphenyl-4-yl]propanoic acid,
116. 3-[3'-(1-methyl-3-pentylureido)-3-(4,4,4-trifluorobutoxy)biphenyl-4-yl]propanoic acid,
117. 3-[3-benzyloxy-3'-(1-methyl-3-pentylureido)biphenyl-4-yl]propanoic acid,
118. 3-[3'-{3-[2-(4-methoxyphenyl)ethyl]-1-methylureido}-3-(3-trifluoromethylbenzyloxy)biphenyl-4-yl]propanoic acid,
119. 3-(3'-{3-[2-(3-methoxyphenyl)ethyl]-1-methylureido}-3,5-dipropylbiphenyl-4-yl)propanoic acid,
120. 3-[3-(2,2-dimethylpropyl)-3'-(1-methyl-3-pentylureido)biphenyl-4-yl]propanoic acid,
121. 3-[3,5-dimethyl-3'-(1-methyl-3-pentylureido)biphenyl-4-yl]propanoic acid,
122. 3-[4"-methoxy-3-(1-methyl-3-pentylureido)[1,1';3',1"]terphenyl-4'-yl]propanoic acid, 123. 3-[3"-methoxy-3-(1-methyl-3-pentylureido)[1,1';2',1"]terphenyl-4'-yl]propanoic acid,
124. 3-(3-{3-[2-(3-methoxyphenyl)ethyl]-1-methylureido}-3"-trifluoromethyl[1,1';2',1"]terphenyl-4'-yl)propanoic acid,
125. 3-{3'-(3-butyl-1-methylureido)-2-[2-(3-isopropoxyphenyl)ethyl]biphenyl-4-yl}propanoic acid,
127. 3-[3-(2-methoxyethylamino)-3'-(1-methyl-3-pentylureido)biphenyl-4-yl]propanoic acid,
128. methyl 3-[3,5-diethyl-3'-(1-methyl-3-pentylureido)biphenyl-4-yl]propanoate,
129. methyl 3-[3'-[1-methyl-3-(3-phenoxyphenyl)ureido]-2-(3-trifluoromethylbenzyloxy)biphenyl-4-yl]propanoate,
130. methyl 3-[3'-[3-(2-biphenyl-4-ylethyl)-1-methylureido]-2-(3-methoxybenzyloxy)biphenyl-4-yl]propanoate,
131. ethyl 3-[3'-{3-[2-(3-methoxyphenyl)ethyl]-1-methylureido}-2-(4,4,4-trifluorobutoxy)biphenyl-4-yl]propanoate, and mixtures thereof.

16. The biaromatic compound of claim 1, wherein at least one of the following conditions is satisfied:
R1 is a hydroxyl or hydroxylamine radical;
R2 and R7 are each an alkoxy or aryloxy radical, an alkylamino radical or a polyether radical;
R3 and R8 are each a hydrogen atom;
R4 is a lower alkyl radical comprising from 1 to 4 carbon atoms;
R5 is an alkyl radical comprising from 3 to 8 carbon atoms or an aryl radical;
Y is an oxygen atom.

17. The biaromatic compound of claim 1, wherein all of the following conditions are satisfied:
R1 is a hydroxyl or hydroxylamine radical;
R2 and R7 are each an alkoxy or aryloxy radical, an alkylamino radical or a polyether radical;
R3 and R8 are each a hydrogen atom;
R4 is a lower alkyl radical comprising from 1 to 4 carbon atoms;
R5 is an alkyl radical comprising from 3 to 8 carbon atoms or an aryl radical; and
Y is an oxygen atom 18. A cosmetic composition comprising a cosmetically effective amount of at least one biaromatic compound of claim 1, formulated into a cosmetically and physiologically acceptable vehicle therefor.

19. The cosmetic composition of claim 18, comprising from 0.001% to 3% by weight of said at least one biaromatic compound.

20. The cosmetic composition of claim 18, formulated for body or hair hygiene.

21. A pharmaceutical composition comprising a pharmaceutically effective amount of at least one biaromatic compound of claim 1, formulated into a pharmaceutically and physiologically acceptable vehicle therefor.

22. The pharmaceutical composition of claim 21, comprising from 0.001% to 10% by weight of said at least one biaromatic compound.

23. A regime or regimen for regulating and/or restoring the metabolism of skin lipids, comprising administering to an individual in need of such treatment, a thus effective amount of the pharmaceutical composition of claim 21.

24. The biaromatic compound of claim 1, in solid form.

* * * * *